US007960511B2

(12) United States Patent
Muramoto et al.

(10) Patent No.: US 7,960,511 B2
(45) Date of Patent: Jun. 14, 2011

(54) ACID-RESISTANCE ENDOGLUCANASE AND THE USE OF THEREOF

(75) Inventors: Nobuhiko Muramoto, Ichinomiya (JP); Chie Imamura, Nagoya (JP); Kenro Tokuhiro, Aichi-gun (JP); Haruo Takahashi, Ogaki (JP)

(73) Assignee: Kabushiki Kaisha Toyota Chuo Kenkyusho, Aichi (JP)

( * ) Notice: Subject to any disclaimer, the term of this patent is extended or adjusted under 35 U.S.C. 154(b) by 0 days.

(21) Appl. No.: 12/385,505

(22) Filed: Apr. 9, 2009

(65) Prior Publication Data
US 2009/0298145 A1 Dec. 3, 2009

(51) Int. Cl.
*C07K 1/00* (2006.01)
(52) U.S. Cl. ........ 530/350; 530/300; 435/252; 435/325; 435/7.1
(58) Field of Classification Search .................. None
See application file for complete search history.

(56) References Cited

U.S. PATENT DOCUMENTS

| | | | |
|---|---|---|---|
| 4,935,366 | A | 6/1990 | Eriksson et al. |
| 6,001,639 | A | 12/1999 | Schulein et al. |
| 6,187,732 | B1 | 2/2001 | Fowler et al. |
| 6,268,328 | B1 | 7/2001 | Mitchinson et al. |
| 6,387,690 | B1 | 5/2002 | Schulein et al. |
| 6,407,046 | B1 | 6/2002 | Fowler et al. |
| 6,500,211 | B2 | 12/2002 | Fowler et al. |
| 6,579,841 | B1 | 6/2003 | Day et al. |
| 6,582,750 | B2 | 6/2003 | Fowler et al. |
| 6,623,949 | B1 | 9/2003 | Gualfetti et al. |
| 6,635,465 | B1 | 10/2003 | Gualfetti et al. |
| 6,855,531 | B2 | 2/2005 | Shulein et al. |
| 7,094,588 | B2 | 8/2006 | Gualfetti et al. |
| 7,226,773 | B2 | 6/2007 | Schulein et al. |
| 2008/0145912 | A1 | 6/2008 | Schulein et al. |

FOREIGN PATENT DOCUMENTS

| | | |
|---|---|---|
| JP | A-11-502701 | 3/1999 |
| JP | A-2003-235579 | 8/2003 |
| JP | A-2003-259878 | 9/2003 |
| JP | A-2003-527065 | 9/2003 |
| JP | A-2004-505629 | 2/2004 |
| JP | A-2004-505630 | 2/2004 |
| JP | A-2004-512827 | 4/2004 |
| JP | A-2004-518406 | 6/2004 |
| JP | A-2004-187643 | 7/2004 |
| JP | A-2005-137306 | 6/2005 |
| JP | A-2006-20602 | 1/2006 |
| JP | A-2006-28318 | 2/2006 |
| JP | A-2006-42719 | 2/2006 |
| JP | A-2006-136233 | 6/2006 |
| JP | A-2006-296377 | 11/2006 |
| JP | A-2007-89466 | 4/2007 |
| JP | A-2007-175029 | 7/2007 |
| WO | WO 99/31255 | 6/1999 |
| WO | WO 01/79483 | 10/2001 |
| WO | WO 02/42483 A1 | 5/2002 |
| WO | WO 03/016525 | 2/2003 |

OTHER PUBLICATIONS

Wymelenberg et al. (J. Biotechnology, vol. 118, pp. 17-34, 2005).*
Wells ( Biochemistry, vol. 29, pp. 8509-8517, 1990).*
Seffernick et al. (J. Bacteriology, vol. 183, pp. 2405-2410, 2001).*
Mats Sandgren et al; Comparison of family 12 glycoside hydrolases and recruited substitutions important for thermal stability, Protein Science (2003), 12:848-860.
Jim E. Pitts et al; Expression and characterization of chymosin pH optima mutants produced in *Trichoderma reesei*; Journal of Biotechnology, 28 (1993) pp. 69-83.
Manish D. Joshi et al; Hydrogen Bonding and Catalysis: A Novel Explanation for How a Single Amino Acid Substitution Can Change the pH Optimum of a Glycosidase; J. Mol. Biol. (2000) 299, pp. 255-279.
Phanerochaete chrysosporium endoglucanase (cell2A) mRNA, complete cdsl (online), NCBI, Jul. 18, 2005, Accession: AY682744, Apr. 2, 2010.
Notification of Reasons for Rejection for Application No. 2008-102744; mailed Apr. 13, 2010 (with translation).
Gunnar Henriksson et al; Endoglucanase 28 (Cell2A), a new *Phanerochaete chrysoporium* cellulose, in Eur. J. Biochem. 259, pp. 88-95 (1999) FEBS 1999.
Johan Karlsson et al; Enzymatic properties of the low molecular mass endoglucanases Cell 2A (EG III) and Cel45A (EG V) of *Trichoderma reesei*, in Journal of Biotechnology 99 (2002) pp. 63-78.
Amber Vanden Wymelenberg et al; The phanerochaete chrysoporium secretome: Database predictions and initial-mass spectrometry peptide identifications in cellulose-grown medium; in Journal of Biotechnology 118 (2005) pp. 17-34.
Tomoko Shimokawa et al; Purification, Molecular Cloning, and Enzymatic Properties of a Family 12 Endoglucanase (EG-II) from *Fomitopsis palustris*: Role of EG-II in Larch Holocellulose Hydrolysis, in Applied and Environmental Microbiology, Sep. 2008, pp. 5857-5861, vol. 74, No. 18. Ute Krengel et al; Three-dimensional Structure of Endo-1, 4-xylanase I from *Aspergillus niger*: Molecular Basis for its Low pH Optimum; in J. Mol. Biol. (1996) 263, pp. 70-78.
Jeong-Jun Yoon et al; Degradation of Crystalline Cellulose by the Brown-rot Basidiomycete *Fomitopsis palustris*; The Journal of Mircrobiology, Dec. 2005, pp. 487-492, The Microbiological Society of Korea; vol. 43, No. 6.
Harry Boer et al; The relationship between thermal stability and pH optimum studied with wild-type and mutant *Trichoderma reesei* cellobiohydrolase Cel7A; Eur. J. Biochem. 270, pp. 841-848 (2003) FEBS 2003.
Dieter Becker et al; Engineering of a glycosidase Family 7 cellobiohydrolase to more alkaline pH optimum: the pH behaviour of *Trichoderma reesei* Cel7A and its E223S/A224H/L225V/T226A/D262g mutant, Biochem J. (2001) 356, pp. 19-30.

(Continued)

Primary Examiner — Hope A Robinson
(74) Attorney, Agent, or Firm — Oliff & Berridge, PLC

(57) ABSTRACT

The present teachings relate to an acid-resistant endoglucanase, which is a protein exhibiting excellent endoglucanase activity under acidic conditions. The present teachings provide a protein having the amino acid sequence set forth in SEQ ID NO: 2, a protein having an amino acid sequence with one or more amino acid modifications in the amino acid sequence set forth in SEQ ID NO: 2 and having endoglucanase activity, or a protein having an amino acid sequence with at least 75% homology to the amino acid sequence set forth in SEQ ID NO: 2 and having endoglucanase activity.

13 Claims, 16 Drawing Sheets

OTHER PUBLICATIONS

Ting Wang et al; Directed evolution for engineering pH profile of endoglucanase III from *Trichoderma reesei*; Biomolecular Engineering 22 (2005) pp. 89-94.

Hirofumi Okada et al; Molecular Characterization and Heterologous Expression of the Gene Encoding a Low-Molecular-Mass Endoglucanase from *Trichoderma reesei* QM9414, vol. 64, No. 2.

Okada et al., "Molecular Characterization and Heterologous Expression of the Gene Encoding a Low-Molecular-Mass Endoglucanase from *Trichoderma reesei* QM9414", Applied and Environmental Microbiology, vol. 64, No. 2, pp. 555-563, Feb. 1998.

Japanese Decision of Rejection issued in Japanese Patent Application No. 2008-102744 mailed on Aug. 17, 2010 with English-language translation of Decision of Rejection.

* cited by examiner

|  |  | SECRETION SIGNAL |  |  |
|---|---|---|---|---|
| Pc-cel12A AY682744 (EG) aa. seq | 1: | MFKALLAVCFAIALTFASAAQTITCQYDCIPAGAYTLCQNLWGEYAGVGSQNSTLISTNG | 60 | (SEQ ID NO: 31) |
| Pc-cel12A ATCC64314 aa. seq | 1: | ------------------------------------------------------------ | 38 | |

\*\*\*\*\*\*\*\*\*\*\*\*\*\*\*\*\*\*\*\*\*\*\*\*\*\*\*\*\*\*\*\*\*\*\*\*\*\*\*\*\*\*\*\*

| Pc-cel12A AY682744 (EG) aa. seq | 61: | NAVTWQTNWTWANNPNTVKS----------CASHSFPIASSAPTANNWTYVTESGGIRADVS | 112 | (SEQ ID NO: 32) |
|---|---|---|---|---|
| Pc-cel12A ATCC64314 aa. seq | 39: | .....................YANLEHNTAKGMQLGTIT....................... | 98 | (SEQ ID NO: 33) |

\*\*\*\*\*\*\*\*\*\*\*\*\*\*\*\*\*\*\*\* INSERTED/SUBSTITUTED SEQUENCE \*\*\*

| Pc-cel12A AY682744 (EG) aa. seq | 113: | YDINFGKAQSGNPATSASSYEIMIWLSGLGGIGPVGHQILSGLNIAGHTWNLWSGPNSNA | 172 | (SEQ ID NO: 34) |
|---|---|---|---|---|
| Pc-cel12A ATCC64314 aa. seq | 99: | ............................................................ | 158 | |

\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*

| Pc-cel12A AY682744 (EG) aa. seq | 173: | QYFSFVISSGEVRNFSADLNEFFQYLIQSQGVASTQYLQAIQVGTEPFVGSASLLTESFA | 232 | (SEQ ID NO: 35) |
|---|---|---|---|---|
| Pc-cel12A ATCC64314 aa. seq | 159: | ............................................................ | 218 | |

\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*

| Pc-cel12A AY682744 (EG) aa. seq | 233: | VAVNV--- | 237 | (SEQ ID NO: 36) |
|---|---|---|---|---|
| Pc-cel12A ATCC64314 aa. seq | 219: | ......GS | 225 | |

```
ATCTCGATCCCGCGAAATTAATACGACTCACTATAGGGAGACCACAACGGTTTCCCTCTA
           70        80        90       100       110       120
GAAATAATTTTGTTTAACTTTAAGAAGGAGATATACATATGGCACAGACTATCACAGGAC
                                         M  A  Q  T  I  T  G  Q 130       140       150       160       170       180
AGTACGACTGCATTCCTGCGGGAGCGTACACGCTTTGTCAAAACCTCTGGGGCGAATACG
 Y  D  C  I  P  A  G  A  Y  T  L  C  Q  N  L  W  G  E  Y  A 190       200       210       220       230       240
CTGGAGTTGGCTCGCAGAACTCGACTCTGATCAGTACAAATGGCAACGCCGTGACTTGGC
 G  V  G  S  Q  N  S  T  L  I  S  T  N  G  N  A  V  T  W  Q 250       260       270       280       290       300
AGACCAACTGGACATGGGCCAACAATCCCAACACCGTAAAGAGCTACGCGAACCTAGAGC
 T  N  W  T  W  A  N  N  P  N  T  V  K  S  Y  A  N  L  E  H 310       320       330       340       350       360
ACAACACCGCGAAGGGCATGCAGCTCGGGACCATCACGAGCGCGCCGACCGCGTGGAACT
 N  T  A  K  G  M  Q  L  G  T  I  T  S  A  P  T  A  W  N  W 370       380       390       400       410       420
GGACCTACGTTACCGAATCTCAGGGCATCCGCGCCGACGTCTCCTATGACATCTGGTTCG
 T  Y  V  T  E  S  Q  G  I  R  A  D  V  S  Y  D  I  W  F  G 430       440       450       460       470       480
GCAAGGCCCAGTCCGGCAACCCAGCGACGTCTGCCTCTTCCTATGAGATCATGATCTGGC
 K  A  Q  S  G  N  P  A  T  S  A  S  S  Y  E  I  M  I  W  L 490       500       510       520       530       540
TGTCCGGCCTCGGCGGTATCCAGCCTGTCGGCCACCAGATTCTCAGCGGCCTCAACATCG
 S  G  L  G  G  I  Q  P  V  G  H  Q  I  L  S  G  L  N  I  A 550       560       570       580       590       600
CTGGACACACCTGGAACCTCTGGAGCGGCCCGAACTCAAACTGGCAGGTCTTCTCGTTCG
 G  H  T  W  N  L  W  S  G  P  N  S  N  W  Q  V  F  S  F  V 610       620       630       640       650       660
TCATCTCCTCCGGCGAAGTGAGGAACTTCAGCGCGGACCTTAACGAGTTCTTCCAGTATC
 I  S  S  G  E  V  R  N  F  S  A  D  L  N  E  F  F  Q  Y  L 670       680       690       700       710       720
TCATCCAGAGCCAGGGCGTGGCCTCGACCCAGTACCTCCAAGCTATTCAAGTCGGCACCG
 I  Q  S  Q  G  V  A  S  T  Q  Y  L  Q  A  I  Q  V  G  T  E 730       740       750       760       770       780
AACCATTCGTCGGCTCTGCAAGCCTGCTGACAGAGAGTTTCGCAGTCGCAGTCAACGTTT
 P  F  V  G  S  A  S  L  L  T  E  S  F  A  V  A  V  N  V  *

790       800       810       820       830       840
GACTCGAGATCCGGCTGCTAACAAAGCCCGAAAGGAAGCTGAGTTGGCTGCTGCCACCGC 850       860       870       880       890       900
TGAGCAATAACTAGCATAACCCCTTGGGGCCTCTAAACGGGTCTTGAGGGGTTTTTTGCT 910       920       930
GAAAGGAGGAACTATATCCGGA
```

(SEQ ID NO: 23)

Fig.4

```
        10         20         30         40         50         60
ATCTCGATCCCGCGGAAATTAATACGACTCACTATAGGGAGACCACAACGGTTTCCCTCTA 70         80         90        100        110        120
GAAATAATTTTGTTTAACTTTAAGAAGGAGATATACATATGGAGCAGACTGTCTCTGGGGCC
                                      M  Q  Q  T  V  W  G  Q 130        140        150        160        170        180
AGTGTGGAGGGTATTGGTGGAGGGACCTACGAATTGTCTCCTGGCTCAGCTTGTTCGA
 C  G  G  I  G  W  S  G  P  T  N  C  A  P  G  S  A  C  S  T 190        200        210        220        230        240
CCCTCAATCCTTATTATGCGGCAATGTATTCCGGAGGCCACTACTATCACCACTTGAGCC
 L  N  P  Y  Y  A  Q  C  I  P  G  A  T  T  T  T  S  T  R 250        260        270        280        290        300
GGCCACCATCCGGTCCAACCACCACCAGGGCTACCTCAACAAGGTCATCAACTCCAC
 P  P  S  G  P  T  T  T  T  R  A  T  S  T  S  S  S  T  P  P 310        320        330        340        350        360
TCCGGAGCTCTGGGGTCCGATTTGCCGGCGGTTAACATGCGGAGGTTTTGACTTTGGCTGTA
 T  S  S  G  V  R  F  A  G  V  N  I  A  G  F  D  F  G  C  T 370        380        390        400        410        420
CCACGAGATGGCACTTGCGTTACCTGAAGGTTATCCCGTTGAAGAACTTCACGGCT
 T  D  G  T  C  V  T  S  K  V  Y  P  P  L  K  N  F  T  G  S 430        440        450        460        470        480
CCACAGAACTACCCCGATGGCATCGGCCAGATGCAGCACTTCGTCAACGACGACGGGATGA
 T  T  N  Y  P  D  D  G  I  G  Q  M  Q  H  F  V  N  D  D  G  M  T 490        500        510        520        530        540
CAAACAACTACCCCGATGGCATCGGCCAGATGCAGCACTTCGTCAACGACAATTTGGGGGCAATC
 N  N  Y  P  D  D  G  I  G  Q  M  Q  H  F  V  N  N  L  G  G  N  L 550        560        570        580        590        600
CTATTTCCGCCTTACCTGTCGATGGCAGTACCTCGTCAACAACTTGTTCAGGGGCCTGTCGTCTGGGCG
 I  F  R  L  P  V  G  W  Q  Y  L  V  N  N  L  G  G  N  L 610        620        630        640        650        660
TTGATTCACGAGCATCTTCCAAGTATGATCAGCCTTCGGGGGGCCTTGTCGTCTGGGCG
 D  S  T  S  I  S  K  Y  D  Q  L  V  Q  G  C  L  S  L  G  A 670        680        690        700        710        720
CATACTGCATCGTCGACAATCGTCAATTCACGAGCCCTTTGGTCGCAGTGGCATCAAAGTACGGCAT
 Y  C  I  V  D  I  H  N  Y  A  R  W  N  G  G  I  I  G  Q  Q
GCGGCCCTACTAATGCTCAATTCACGAGCCCTTTGGTCGCAGTGGCATCAAAGTACGCAT
 G  P  T  N  A  Q  F  T  S  L  W  S  Q  L  A  S  K  Y  A  S 730        740        750        760        770        780
CTCAGTCGAGGGTGTGGTTCGGTCATGAATGAGCCCCACGACGTGAACATCAACACCT
 Q  S  R  V  V  W  F  G  I  M  N  E  P  H  D  V  N  I  N  T  W 790        800        810        820        830        840
GGGCTGCCAGGTCCAAGAGGTTGTAACCGCAATCGGCAACGCTGGTGCTACGTCGGCAAT
 A  A  T  V  Q  E  V  V  T  A  I  R  N  A  G  A  T  S  Q  F 850        860        870        880        890        900
TCATCTCTTTGCCTGGAAATGATTGGCAATCGCTGGGGCTTTCATATCCGATGGCAGTG
 I  S  L  P  G  N  D  W  Q  S  A  G  A  F  I  S  D  G  S  A 910        920        930        940        950        960
CAGCCGCCCTGTCTCAAGTCAAGGACTTCAGGACTCGGTACTCGGCGGATGGCACTCGATTTTGACG
 A  A  L  S  Q  V  T  N  P  D  G  S  T  T  N  L  I  F  D  V 970        980        990       1000       1010       1020
TGCACAAATACTTGGACTTAGACAACTCCGGTACTCACGCCGAATGTACTACAAATAACA
 H  K  Y  L  D  L  D  N  S  G  T  H  A  E  C  T  T  N  N  I 1030       1040       1050       1060       1070       1080
TTGACGGCGCCTTTTCTCCGCTTGCCAGTTGGCTCCGACAGAACAATCGCCAGGCTATCC
 D  G  A  F  S  P  L  A  T  W  L  R  Q  N  N  R  Q  A  I  L 1090       1100       1110       1120       1130       1140
TGACAGAAACCGGTGGTGGGGAACGTTCAGTCTGCATAGAAGACATGTGCCAGCAAATCC
 T  E  T  G  G  G  N  V  Q  S  C  I  Q  D  M  C  Q  Q  I  Q 1150       1160       1170       1180       1190       1200
AATATCTCAACCAGAACTCAGATGTCTATCTTGGCTATCTTGGTTGGGGTGCCGGAAGCT
 Y  L  N  Q  N  S  D  V  Y  L  G  Y  Y  V  G  W  G  A  G  S  F 1210       1220       1230       1240       1250       1260
TTGATAGCACGTATGTCCTGACGGAAACACCGACTGGCAGTGGTAACTCATGGACGGACA
 D  S  T  Y  V  L  T  E  T  P  T  G  S  G  N  S  W  T  D  T 1270       1280       1290       1300       1310       1320
CATCCTTGGTCAGCTCGTGTCTCGCCGAAGAAAGTAGCTCGAGATCCGGCTGCTAACAAAGC
 S  L  V  S  S  C  L  A  R  K  *

1330       1340       1350       1360       1370       1380
CCGAAAGGAAGCTGAGTTGGCTGCTGCCACCGCTGAGCAATAACTAGCAATAACCCCTTGG 1390       1400       1410       1420       1430       1440
GGCCTCTAAACGGGTCTTGAGGGGTTTTTTGCTGAAAGGAGGAACTATATCCGGA

Fig.5

(SEQ ID NO: 25)
```

```
         10        20        30        40        50        60
ATCTCGATCCCGCGAAATTAATACGACTCACTATAGGGAGACCACAACGGTTTCCCTCTA 70        80        90       100       110       120
GAAATAATTTTGTTTAACTTTAAGAAGGAGATATACATATGCAAACCAGCTGTGACCAGT
                                       M  Q  T  S  C  D  Q  W 130       140       150       160       170       180
GGGCAACCTTCACTGGCAACGGCTACACAGTCAGCAACAACCTTTGGGGAGCATCAGCCG
 A  T  F  T  G  N  G  Y  T  V  S  N  N  L  W  G  A  S  A  G 190       200       210       220       230       240
GCTCTGGATTTGGCTGCGTGACGGCGGTATCGCTCAGCGGCGGGGCCTCCTGGCACGCAG
 S  G  F  G  C  V  T  A  V  S  L  G  G  A  S  W  H  A  D 250       260       270       280       290       300
ACTGGCAGTGGTCCGGCGGCCAGAACAACGTCAAGTCGTACCAGAACTCTCAGATTGCCA
 W  Q  W  S  G  G  Q  N  N  V  K  S  Y  Q  N  S  Q  I  A  I 310       320       330       340       350       360
TTCCCCAGAAGAGGACCGTCAACAGCATCAGCAGCATGCCCACCACTGCCAGCTGGAGCT
 P  Q  K  R  T  V  N  S  I  S  S  M  P  T  T  A  S  W  S  Y 370       380       390       400       410       420
ACAGCGGGAGCAACATCCGCGCTAATGTTGCGTATGACTTGTTCACCGCAGCCAACCCGA
 S  G  S  N  I  R  A  N  V  A  Y  D  L  F  T  A  A  N  P  N 430       440       450       460       470       480
ATCATGTCACGTACTCGGGAGACTACGAACTCATGATCTGGCTTGGCAAATACGGCGATA
 H  V  T  Y  S  G  D  Y  E  L  M  I  W  L  G  K  Y  G  D  I 490       500       510       520       530       540
TTGGGCCGATTGGGTCCTCACAGGGAACAGTCAACGTCGGTGGCCAGAGCTGGACGCTCT
 G  P  I  G  S  S  Q  G  T  V  N  V  G  G  Q  S  W  T  L  Y 550       560       570       580       590       600
ACTATGGCTACAACGGAGCCATGCAAGTCTATTCCTTTGTGGCCCAGACCAACACTACCA
 Y  G  Y  N  G  A  M  Q  V  Y  S  F  V  A  Q  T  N  T  T  N 610       620       630       640       650       660
ACTACAGCGGAGATGTCAAGAACTTCTTCAATTATCTCCGAGACAATAAAGGATACAACG
 Y  S  G  D  V  K  N  F  F  N  Y  L  R  D  N  K  G  Y  N  A 670       680       690       700       710       720
CTGCAGGCCAATATGTTCTTAGCTACCAATTTGGTACCGAGCCCTTCACGGGCAGTGGAA
 A  G  Q  Y  V  L  S  Y  Q  F  G  T  E  P  F  T  G  S  G  T 730       740       750       760       770       780
CTCTGAACGTCGCATCCTGGACCGCATCTATCAACTAACTCGAGATCCGGCTGCTAACAA
 L  N  V  A  S  W  T  A  S  I  N  *

790       800       810       820       830       840
AGCCCGAAAGGAAGCTGAGTTGGCTGCTGCCACCGCTGAGCAATAACTAGCATAACCCCT 850       860       870       880       890       900
TGGGGCCTCTAAACGGGTCTTGAGGGGTTTTTTGCTGAAAGGAGGAACTATATCCGGA
```

(SEQ ID NO: 27)

Fig.6

Molecule sequenced :
Gene name         :
Sequence length   : 898 base pairs

```
atctcgatcc cgcgaaatta atacgactca ctataggag accacaacgg tttccctcta                    60
gaaataattt tgtttaactt taagaaggag atatacat atg gca cag act atc aca                  116
                                          Met Ala Gln Thr Ile Thr
                                          1               5 gga cag tac gac tgc att cct gcg gga gcg tac acg ctt tgt caa aac                   164
Gly Gln Tyr Asp Cys Ile Pro Ala Gly Ala Tyr Thr Leu Cys Gln Asn
            10                  15                  20 ctc tgg ggc gaa tac gct gga gtt ggc tcg cag aac tcg act ctg atc                   212
Leu Trp Gly Glu Tyr Ala Gly Val Gly Ser Gln Asn Ser Thr Leu Ile
        25                  30                  35 agt aca aat ggc aac gcc gtg act tgg cag acc aac tgg aca tgg gcc                   260
Ser Thr Asn Gly Asn Ala Val Thr Trp Gln Thr Asn Trp Thr Trp Ala
    40                  45                  50 aac aat ccc aac acc gta aag agc tgt gcg tcg cac tcc ttc cct ata                   308
Asn Asn Pro Asn Thr Val Lys Ser Cys Ala Ser His Ser Phe Pro Ile
55                  60                  65                  70 gcg agc tcc gcg ccg acc gcg tgg aac tgg acc tac gtt acc gaa tct                   356
Ala Ser Ser Ala Pro Thr Ala Trp Asn Trp Thr Tyr Val Thr Glu Ser
                75                  80                  85 cag ggc atc cgc gcc gac gtc tcc tat gac atc tgg ttc ggc aag gcc                   404
Gln Gly Ile Arg Ala Asp Val Ser Tyr Asp Ile Trp Phe Gly Lys Ala
            90                  95                  100 cag tcc ggc aac cca gcg acg tct gcc tct tcc tat gag atc atg atc                   452
Gln Ser Gly Asn Pro Ala Thr Ser Ala Ser Ser Tyr Glu Ile Met Ile
        105                 110                 115 tgg ctg tcc ggc ctc ggc ggt atc cag cct gtc ggc cac cag att ctc                   500
Trp Leu Ser Gly Leu Gly Gly Ile Gln Pro Val Gly His Gln Ile Leu
    120                 125                 130
```

(SEQ ID NO: 29)

Fig.7A

```
agc ggc ctc aac atc gct gga cac acc tgg aac ctc tgg agc ggc ccg      548
Ser Gly Leu Asn Ile Ala Gly His Thr Trp Asn Leu Trp Ser Gly Pro
135             140             145             150 aac tca aac tgg cag gtc ttc tcg ttc gtc atc tcc tcc ggc gaa gtg      596
Asn Ser Asn Trp Gln Val Phe Ser Phe Val Ile Ser Ser Gly Glu Val
                155             160             165 agg aac ttc agc gcg gac ctt aac gag ttc ttc cag tat ctc atc cag      644
Arg Asn Phe Ser Ala Asp Leu Asn Glu Phe Phe Gln Tyr Leu Ile Gln
            170             175             180 agc cag ggc gtg gcc tcg acc cag tac ctc caa gct att caa gtc ggc      692
Ser Gln Gly Val Ala Ser Thr Gln Tyr Leu Gln Ala Ile Gln Val Gly
        185             190             195 acc gaa cca ttc gtc ggc tct gca agc ctg ctg aca gag agt ttc gca      740
Thr Glu Pro Phe Val Gly Ser Ala Ser Leu Leu Thr Glu Ser Phe Ala
    200             205             210 gtc gca gtc aac gtt tga ctcgagatcc ggctgctaac aaagcccgaa aggaagct   796
Val Ala Val Asn Val
215             220 gagttggctg ctgccaccgc tgagcaataa ctagcataac cccttggggc ctctaaacgg   856
gtcttgaggg gttttttgct gaaaggagga actatatccg ga                      898
```

(SEQ ID NO: 29 CONTINUED)

Fig.7B

| VARIANT | pH | | | | |
|---|---|---|---|---|---|
| | 2 | 2.5 | 3 | 4 | 5 |
| 11 | 4.4 | 2.0 | 2.0 | 1.5 | 1.1 |
| 12 | 2.9 | 1.0 | 0.5 | 0.5 | 0.3 |
| 14 | 2.4 | 1.0 | 1.2 | 1.0 | 0.4 |
| 19 | 1.6 | 1.4 | 0.5 | 1.0 | 0.7 |
| 93 | 2.2 | 1.6 | 1.1 | 0.9 | 0.7 |
| Pccel 12A | 1.0 | 1.0 | 1.0 | 1.0 | 1.0 |
| TrEGIII | 0.42 | 0.33 | 0.19 | 0.26 | 0.60 |
| TrEGII | 0.18 | 0.09 | 0.12 | 0.27 | 0.31 |

Fig.11

| VARIANT | POSITION IN AMINO ACID SEQUENCE SET FORTH IN SEQ ID NO:2 | | | | | | |
|---|---|---|---|---|---|---|---|
| | 105 | 107 | 126 | 152 | 171 | 192 | 201 |
| | K* | Q | G | S | R* | S | *V* |
| 11 | | *P* | S | | | | *A* |
| 12 | | | | G | | *L* | *A* |
| 14 | | | | | | *L* | |
| 19 | E** | | | | | | |
| 93 | | | | | *M* | | |

GOTHIC BOLD: HYDROPHILIC AMINO ACIDS
ITALICS: HYDROPHOBIC AMINO ACIDS
*: POSITIVELY CHARGED AMINO ACIDS
**: NEGATIVELY CHARGED AMINO ACIDS

ACID-RESISTANCE ENDOGLUCANASE AND THE USE OF THEREOF

CROSS-REFERENCE TO RELATED APPLICATION

This application claims priority from Japanese Patent Application No. 2008-102744, filed on Apr. 10, 2008, which is incorporated herein by reference.

BACKGROUND OF THE INVENTION

1. Field of the Invention

The present invention relates to an acid-resistant endoglucanase and its use.

2. Description of the Related Art

In recent years, biomass created by the photosynthetic action of plants has shown increasing promise as an alternative to finite petroleum resources. A range of endeavors to utilize biomass in energy and the production of various types of materials is in progress. In order for biomass to be effectively utilized as an energy source as well as a raw material for other applications, it is essential that the biomass be rendered by saccharification into a carbon source which is available for uses by animals and microorganisms.

To utilize cellulose, a typical component of biomass, it is regarded as desirable to convert cellulase to glucose (i.e. saccharification) by decomposing the cellulose with a cellulase such as endoglucanase. Various cellulases and modified cellulases capable of efficiently decomposing cellulose are being tested for this purpose. In particular, a number of investigations have been conducted on endoglucanases produced by filamentous fungi of e.g., the genus *Trichoderma* (Patent Document 1, 2 and 3). In addition, a process of inducing the display of cellulase at the surface of yeast cells, decomposing cellulose to glucose with the cellulase, and using the resulting glucose as a carbon source to produce ethanol is also being studied (Patent Document 4).

Prior Art Documents (Patent Documents)

Patent Document 1: U.S. Pat. No. 7,094,588 B2
Patent Document 2: U.S. Pat. No. 6,268,328 B1
Patent Document 3: U.S. Pat. No. 6,623,949 B1
Patent Document 4: International Disclosure WO 01/079483

SUMMARY OF THE INVENTION

One conceivable approach for using cellulose, a typical biomass material, for the fermentative production of organic acids such as lactic acid entails decomposing the cellulose to form glucose and at the same time using this glucose as the carbon source to carry out organic acid fermentation. However, in organic acid fermentation from cellulose, the culture medium tends to be acidified by the organic acid that is produced. Therefore, in the absence of a cellulase which is able to exhibit a high cellulose decomposing activity under acidic conditions, use of the cellulose is substantially impossible. Also, apart from instances where the medium becomes acidic as a result of the fermentation conditions, acidifying the medium provides the advantage of enabling the effective prevention of contamination by other microorganisms.

Pretreatment for biomass saccharification generally involves pretreatment with an acid, as a result of which the starting liquor from the pretreated biomass is often acidic. Therefore, in the absence of an enzyme which has a high cellulose decomposing activity under acidic conditions, the pretreatment liquid will have to be made neutral.

However, acid-resistant cellulases which function effectively under such acidic conditions, i.e., enzymes having a high cellulase activity under acidic conditions, are not currently available. Nor have endoglucanases derived from *Phanerochaete* spp. been particularly investigated.

It is therefore an object of the present teachings to provide an acid-resistant endoglucanase; that is, a protein which exhibits endoglucanase activity even under acidic conditions. Another object of the present teachings may be to provide effective uses for proteins which exhibit an endoglucanase activity even under acidic conditions.

The inventors, on searching for endoglucanases capable of satisfying the above objects, have discovered proteins with a high endoglucanase activity at low pH levels. By modifying this endoglucanase, they have also discovered variant proteins which exhibit even higher endoglucanase activities under acidic conditions. In addition, the inventors have found that when such endoglucanases are displayed at the surface of yeast cells, which are cells of a different species, the endoglucanase activity under acidic conditions can be stabilized. The inventors disclose the following techniques based on the discovery.

Accordingly, in one aspect of the present teachings, a protein selected from the group of: (a) a protein having the amino acid sequence set forth in SEQ ID NO:2; (b) a protein having an amino acid sequence with one or more amino acid modifications in the amino acid sequence set forth in SEQ ID NO:2, and having endoglucanase activity; and (c) a protein having an amino acid sequence with at least 75% homology to the amino acid sequence set forth in SEQ ID NO:2, and having endoglucanase activity is provided.

In another aspect of the present teachings, a method of screening for modified endoglucanases is provided, which method includes the steps of preparing a library of test proteins obtained by introducing one or more amino acid modifications into an endoglucanase from *Phanerochaete* spp., or into a variant thereof; and assaying the endoglucanase activities under acidic conditions of the test proteins in the library. Proteins having excellent endoglucanase activities under acidic conditions can be efficiently found with such a screening method.

In a further aspect of the present teachings, a DNA construct which includes DNA encoding one of the above proteins is provided. This DNA construct may be an expression vector. In a still further aspect of the present teachings, a transformant obtained through transformation by such a DNA construct is provided.

In an additional aspect of the present teachings, yeast which retains one of the above proteins having endoglucanase activity at a cell surface thereof is provided. In such yeast, the protein is stabilized, enabling a high endoglucanase activity to be exhibited under acidic conditions. The yeast may retain a cellulase other than an endoglucanase at a cell surface thereof, and may be used in particular for fermentation which includes a fermentation step at any pH from 2 to 4. The yeast of the present teachings may be used under culturing conditions at any pH from 2 to 4, and may be used for organic acid fermentation or for ethanol fermentation.

In another aspect of the present teachings, a method of producing a useful substance with yeast that displays an endoglucanase at a cell surface thereof, which method includes the step of producing the useful substance by fermentation using any such yeast in the presence of cellulose is provided. The useful substance may be ethanol. Alternatively, the yeast may be an organic acid-producing yeast, and the organic substance may be an organic acid.

In yet another aspect of the present teachings, a method of improving the acid resistance of a protein, or the activity of the protein under acidic conditions, by displaying the protein at a cell surface of the yeast is provided.

BRIEF DESCRIPTION OF THE DRAWINGS

FIG. 1 contrasts the amino acid sequence of cloned Pccel 12A with an amino acid sequence from *Phanerochaete chrysosporium* that is publicly disclosed in a database (GenBank Accession No. AY682744);

FIG. 4 shows the base sequence of the template DNA for Pccel 12A ATCC64314 used in a cell-free protein synthesis system;

FIG. 5 shows the base sequence of the template DNA for Tr EGII used in a cell-free protein synthesis system;

FIG. 6 shows the base sequence of the template DNA for Tr EGIII used in a cell-free protein synthesis system;

FIG. 7A shows the 5' side of the base sequence of the template DNA for Pc-cel 12A AY682744 used in a cell-free protein synthesis system;

FIG. 7B shows the 3' side of the base sequence of the template DNA for Pc-cel 12A AY682744 used in a cell-free protein synthesis system;

FIG. 11 is a table showing the results of secondary screening by halo assays on primary screened variants;

FIG. 12 shows modifications in the amino acid sequence set forth in SEQ ID NO:1 in primary screened variants;

DESCRIPTION OF THE PREFERRED EMBODIMENTS

Figure 2:
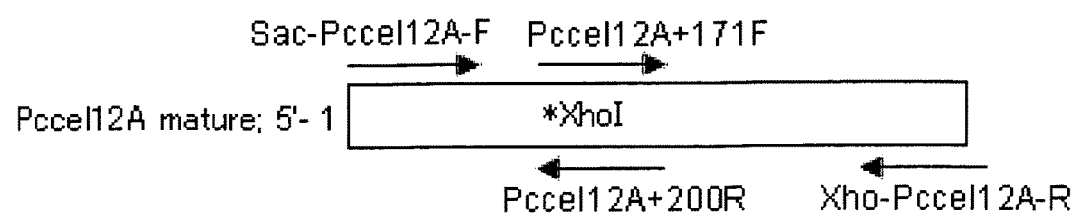
FIG. 2 shows a scheme for sequencing the Pccel 12A gene.

The present teachings relate to a novel protein having endoglucanase activity, variants thereof, a method of screening for endoglucanases, a DNA construct, a transformant, yeast which displays endoglucanase at cell surfaces thereof, and a method of producing useful substances with such yeasts. The novel protein of the present teachings and variants thereof are able to exhibit an endoglucanase activity which functions even under acidic conditions. As a result, for example, in the case of organic acid fermentation using cellulose as the carbon source, even when the pH within the culture medium decreases on account of the lactic acid produced, a decline in the ability to saccharify cellulose can be suppressed or avoided, enabling cellulose to be effectively saccharified and utilized in organic acid fermentation even under such acidic conditions. Moreover, because the cellulose can be decomposed under acidic conditions, the growth of other microorganisms in the cellulose decomposition liquor can be suppressed. Therefore, when carrying out fermentation using cellulose as the carbon source, it is possible to carry out fermentation while effectively suppressing the growth of other organisms. In addition, even in cases where cellulose-containing biomass that has been pretreated with acid is employed as the carbon source, a decrease in the saccharification rate due to residual acid can be suppressed or avoided, enabling the cellulose to be efficiently saccharified.

The present teachings relate to a protein having endoglucanase activity, particularly a protein which exhibits excellent endoglucanase activity under acidic conditions, and to uses thereof. Embodiments of the present teachings include proteins which exhibit endoglucanase activity, polynucleotides, DNA constructs and transformants, yeasts which display endoglucanase at cell surfaces thereof, and methods of screening for modified endoglucanases. Each of these embodiments is described in detail below.

Proteins Which Exhibit Endoglucanase Activity

The protein of the present teachings is a protein selected from one of the below:
(a) a protein having the amino acid sequence set forth in SEQ ID NO:2;
(b) a protein having an amino acid sequence with one or more amino acid modified in the amino acid sequence set forth in SEQ ID NO:2, and having endoglucanase activity; and
(c) a protein having an amino acid sequence with at least 70% homology to the amino acid sequence set forth in SEQ ID NO:2, and having endoglucanase activity.

Amino Acid Sequence

The amino acid sequence set forth in SEQ ID NO:2 is the amino acid sequence of a mature protein isolated from *Phanerochaete chrysosporium*. The inventors analyzed the base sequence of a cloned DNA fragment using the SignalP 3.0 server (http://www.cbs.dtu.dk/services/SignalP/PCR) which is able to predict mature protein regions. As a result thereof, they predicted the region of the polypeptide sequence encoded by this DNA fragment subsequent to the isoleucine at a specific position to be a mature protein. Because this protein was confirmed to have an endoglucanase activity, it was designated as the mature protein having the endoglucanase activity.

The protein having the amino acid sequence set forth in SEQ ID NO:2 is classified as belonging to glycoside hydrolase, family 12. At the pfam homepage (http://pfam.sanger.ac.uk/), it has a domain which aligns with pfam family Accession No.: pf01670. Also, based on alignment between the amino acid sequence in SEQ ID NO:2 and other endoglucanases, the motif region of the eighteen amino acid sequences from position 59 to position 76 (SEQ ID NO:3) of this amino acid sequence is lacking in the mature protein deposited under GenBank Accession No. AY682744 for *Phanerochaete chrysosporium*. Moreover, nothing has been reported on the activity of the mature protein deposited under Accession No. AY682744. It can be concluded from the above that protein having the amino acid sequence set forth in SEQ ID NO:2 is family 12-type endoglucanase which has been cloned for the first time from the genus *Phanerochaete*.

The inventive protein having the amino acid sequence set forth in SEQ ID NO:2 is endoglucanase from a genus *Phanerochaete* organism. Endoglucanases and other enzymes for saccharifying cellulase have previously been investigated not only in filamentous fungi such as organisms of the genera

*Trichoderma* (e.g., *Trichoderma reesei*), *Fusarium, Tremetes, Penicillium, Humicola, Acremonium* and *Aspergillus*, but also in bacteria such as organisms of the genera *Clostridium, Pseudomonas, Cellulomonas, Ruminococcus* and *Bacillus*, archaeons such as organisms of the genera *Sulfolobus*, and actinomycetes such as organisms of the genera *Streptomyces* and *Thermoactinomyces*. Studies are also being done on alkali-resistant endoglucanases with detergent applications in mind. However, most existing endoglucanases have a reaction pH that ranges from weakly acidic to alkaline, and none are known to exhibit a strong endoglucanase activity under acidic conditions. Nor have any detailed investigations been conducted whatsoever on the endoglucanase activities of endoglucanases of genus *Phanerochaete* organisms such as *Phanerochaele chrysosporium*.

The protein of the present teachings may be obtained or modified based on the amino acid sequence set forth in SEQ ID NO:2. That is, it may be a protein having the amino acid sequence of either (a) or (b) above and having endoglucanase activity.

The protein having the amino acid sequence set forth in SEQ ID NO:2 may be one which, aside from the amino acid sequence in SEQ ID NO:2, is obtained by, for example, the addition to the N-terminus of a methionine for protein synthesis, or the addition of an amino acid sequence such as a signal peptide to the N-terminus before becoming a mature protein.

The protein of the present teachings may include an amino acid sequence having at least 75% homology to the amino acid sequence in SEQ ID NO:2 (such a sequence is referred to below as "a homologous amino acid sequence"), or may consist of such a homologous amino acid sequence.

The homologous amino acid sequence preferably has at least 80% homology, more preferably at least 85% homology, even more preferably at least 90% homology, and most preferably at least 95% homology, to the amino acid sequence in SEQ ID NO:2.

In this specification, "homology" (also called "identity") or "similarity," as is commonly known in the technical field to which the present teachings relates, refers to the relationship between two or more proteins or two or more polynucleotides as determined by comparing the sequences thereof. In the art to which the present teachings relates, "identity" refers to the degree of sequence invariance between protein or polynucleotide sequences, as determined by the alignment between protein or polynucleotide sequences or, in some cases, by the alignment between a series of such sequences. "Similarity" refers to the degree of correlation between protein or polynucleotide sequences, as determined by the alignment between protein or polynucleotide sequences or, in some cases, by the alignment between a series of partial sequences. More specifically, these are determined by the identity and conservation (substitutions which maintain specific amino acids within a sequence or the physicochemical properties of the sequence) of the sequence. The similarity is indicated under the heading "Similarity" in the subsequently described BLAST sequence homology search results. The method for determining identity and similarity is preferably a method designed to give the longest alignment between the sequences being compared. Methods for determining identity and similarity are furnished as publicly available programs. For example, determinations can be made using the BLAST (Basic Local Alignment Search Tool) program provided by Altschul et al. (e.g., Altschul, S. F.; Gish, W.; Miller, W.; Myers, E. W.; Lipman, D. J.: *J. Mol. Biol.*, 215:403-410 (1990); Altschul, S. F., Madden, T. L.; Schaffer, A. A.; Zhang, J.; Miller, W.; Lipman, D. J.: *Nucleic Acids Res.* 25:3389-3402 (1997)).

The conditions when using software such as BLAST are not subject to any particular limitation, although using the default values is preferred.

The homologous amino acid sequence may, alternatively, be an amino acid sequence encoded by DNA that hybridizes under stringent conditions with, as the probe, all or some portion of a polynucleotide (e.g., the base sequence set forth in SEQ ID NO: 1) coding for the amino acid sequence set forth in SEQ ID NO:2. "Hybridizes under stringent conditions" herein refers to a DNA base sequence which is obtained by, for instance, colony hybridization, plaque hybridization or Southern hybridization using DNA as the probe. This is exemplified by DNA which, after carrying out hybridization at 65° C. and in the presence of 0.7 to 1.0 M NaCl using a filter on which DNA from a colony or plaque, or fragments of such DNA, has been immobilized, can be identified by washing the filter at 65° C. using a 0.1× to 2×SSC solution (a 1×SSC solution contains 150 mM sodium chloride and 15 mM sodium citrate) at 65° C. Hybridization may be carried out according to a method described in, for example, *Molecular Cloning: A Laboratory Manual*, $3^{rd}$ Ed., (Cold Spring Harbor Laboratory Press; Cold Spring Harbor, N.Y.; 1989) (referred to below as "*Molecular Cloning*, $3^{rd}$ Ed.") or *Current Protocols in Molecular Biology*, Supplements 1 to 38 (John Wiley & Sons, 1987-1997) (referred to below as "*Current Protocols in Molecular Biology*"). DNA hybridized under stringent conditions is exemplified by DNA having at least a given homology to the base sequence of the DNA used as the probe. Examples include DNA having a homology of at least 70%, preferably at least 80%, more preferably at least 90%, even more preferably at least 93%, yet more preferably at least 95%, and most preferably at least 98%.

The protein of the present teachings may include an amino acid sequence having, in the amino acid sequence set forth in SEQ ID NO:2 or a homologous amino acid sequence, one or more amino acid mutations, or may consist of such an amino acid sequence. The number of amino acid mutations is not subject to any particular limitation and may be, for example, from 1 to about 40, preferably from 1 to about 30, more preferably from 1 to about 20, even more preferably from 1 to about 10, still more preferably from 1 to about 5, and most preferably from 1 to about 3. The amino acid mutations may be in the form of amino acid substitutions, deletions or additions, or any combination of two or more of these types of modifications.

The amino acid mutation may take any form, provided the subsequently described endoglucanase activity is achieved. However, it is preferable for the amino acid mutation to take a form in which the protein has hydrophobic amino acid residues at positions 107, 171, 192 and 201, or at positions corresponding thereto, of the amino acid sequence set forth in SEQ ID NO:2. Of these, a form wherein any one or more of positions 107, 192 and 201 has a hydrophobic amino acid residue is preferred. Examples of such amino acid mutation by hydrophobic amino acid residues include those which result in the protein having one of the below amino acid residues:

(1) hydrophobic amino acid residues at positions 107 and 201, or positions corresponding thereto;
(2) hydrophobic amino acid residues at positions 192 and 201, or positions corresponding thereto;
(3) a hydrophobic amino acid residue at position 192, or a position corresponding thereto; and
(4) a hydrophobic amino acid residue at position 171, or a position corresponding thereto.

Examples of hydrophobic amino acid residues include glycine, valine, alanine, leucine, isoleucine, methionine, tryptophan and proline. These may be used singly or as combinations of two or more. Preferred hydrophobic amino acid residues are proline, leucine, methionine, alanine and valine. In (1) above, it is especially preferable for position 107, or a position corresponding thereto, to be proline, and for position 201, or a position corresponding thereto, to be alanine. In (2) above, it is especially preferable for position 192, or a position corresponding thereto, to be leucine, and for position 201, or a position corresponding thereto, to be alanine. In (3) above, it is especially preferable for position 192, or a position corresponding thereto, to be leucine. In (4) above, it is especially preferable for position 171, or a position corresponding thereto, to be methionine.

The amino acid sequence of the inventive protein may, more specifically, have any one amino acid modification selected from among K105E, Q107P, G126S, S152G, R171M, S192L and V201A in the amino acid sequence set forth in SEQ ID NO:2, or an amino acid modification corresponding thereto. In one preferred embodiment, the amino acid sequence of the inventive protein has at least one amino acid modification selected from among Q107P, S192L and V201A. In other preferred embodiment, the amino acid sequence of the inventive protein has at least amino acid modifications Q107P, G126S and V201A, or has at least amino acid modifications S152G, S192L and V201A.

The amino acid mutation may be introduced by various techniques. For example, use may be made of the method of modifying the genetic information such as DNA encoding the amino acid sequence set forth in SEQ ID NO:2 or a homologous sequence. Known techniques such as the Kunkel method or the gapped duplex method, or methods in general accordance therewith, may be employed to introduce the changes in the DNA, modify the genetic information and obtain the inventive protein. For example, modifications may be introduced into the DNA by using a mutagenesis kit that employs site-specific mutagenesis (e.g., Mutan-K and Mutan-G, both available from Takara). Alternatively, gene mutagenesis or the construction of a chimeric gene may be carried out by a technique such as error-prone PCR or DNA shuffling. Error-prone PCR and DNA shuffling are known techniques in the field of the present teachings. For example, reference may be made to Chen, K. and Arnold, F. H.: *Proc. Natl. Acad. Sci. U.S.A.* 90:5618-5622 (1993) concerning error-prone PCR. With regard to molecular evolution engineering technique such as DNA shuffling and cassette PCR, reference may be made to, for example, Kurtzman, A. L., Govindarajan, S., Vahle, K., Jones, J. T., Heinrichs, V., Patten, P. A.: "Advances in directed protein evolution by recursive genetic recombination: Applications to therapeutic proteins," *Curr. Opinion Biotechnol.* 12, 361-370 (2001), and Okuta, A., Ohnishi, A. and Harayama, S.: PCR isolation of catechol 2,3-dioxygenase gene fragments from environmental samples and their assembly into functional genes," *Gene* 212, 221-228 (1998). Of these, it is preferable to employ a non-cellular protein synthesis system which utilizes a molecular evolution technique involving the introduction of random mutations such as by error-prone PCR. The non-cellular protein synthesis system applied for error-prone PCR may be a protein synthesis system which is publicly known or has been disclosed in Japanese Patent Application Publication Nos. 2006-61080 and 2003-116590 filed by the present patent applicant. Active enzymes can easily be obtained by using these non-cellular protein synthesis systems described by the patent applicant. Hence, error-prone PCR in which such a protein synthesis system has been applied may be advantageously used as the technique for acquiring the protein of the present teachings.

Of the inventive proteins, those proteins which have an amino acid sequence with at least 75% homology to the amino acid sequence set forth in SEQ ID NO:2 and those proteins which have an amino acid sequence with one or more amino acid modifications in the amino acid sequence in SEQ ID NO:2 may originate from the genus *hanerochaete*. The fact that endoglucanases from *Phanerochaete chrysosporium* and other *Phanerochaete* spp. exhibit a high endoglucanase activity under acidic conditions has previously been entirely unknown, and was first discovered by the inventors. By using such endoglucanases to decompose cellulose under acidic conditions, it will become possible to efficiently decompose cellulose under more acidic conditions than in the past. The phrase "proteins originating from the genus *Phanerochaete*" refers to proteins which are produced by microorganisms classified as belonging to the genus *Phanerochaete* (which microorganisms may be wild strains or variant strains), or to proteins which are obtained by a genetic engineering technique using genes coding for proteins produced by such microorganisms. Therefore, recombinant proteins produced by a transformant containing an introduced gene that codes for a protein and has been acquired from the genus *Phanerochaete* (or a modified gene thereof) also may be regarded here as "proteins originating from the genus *Phanerochaete*."

Examples of organisms belonging to the genus *Phanerochaete* are listed in the table below. *Phanerochaete chrysosporium* refers herein to the teleomorph of *Sporotrichum pruinosum*.

TABLE 1

GENUS *PHANEROCHAETE*

*Phanerochaete affinis*
*Phanerochaete allantospora*
*Phanerochaete arizonica*
*Phanerochaete australis*
*Phanerochaete avellanea*
*Phanerochaete brunnea*
*Phanerochaete burtii*
*Phanerochaete carnosa*
*Phanerochaete chrysorhiza*
*Phanerochaete chrysosporium*
*Phanerochaete chrysosporium* RP-78
*Phanerochaete crassa*
*Phanerochaete ericina*
*Phanerochaete flava*
*Phanerochaete flavidoalba*
*Phanerochaete hiulca*
*Phanerochaete laevis*
*Phanerochaete magnoliae*
*Phanerochaete pseudomagnoliae*
*Phanerochaete rimosa*
*Phanerochaete sanguinea*
*Phanerochaete sordida*
*Phanerochaete stereoides*
*Phanerochaete subceracea*
*Phanerochaete tuberculata*
*Phanerochaete velutina*
*Phanerochaete velutina* var. *alnea*
*Phanerochaete* sp. DIS 267c
*Phanerochaete* sp. GEL 2547
*Phanerochaete* sp. KUC3031
*Phanerochaete* sp. KUC8073
*Phanerochaete* sp. olrim353
*Phanerochaete* sp. Tm1-1
*Phanerochaete* sp. Y6

Genus *Phanerochaete*

Apart from being obtained by a genetic engineering technique with a non-cellular protein synthesis system such as that described above, the inventive protein may be obtained by a genetic engineering technique that involves transforming a suitable host cell with DNA coding for the inventive protein and inducing the transformant to produce the protein of the present teachings. The production of genetically engineered protein using a transformant may be carried out in general accordance with a method described in, for example, *Molecular Cloning*, 3rd or *Current Protocols in Molecular Biology*.

In cases where the inventive protein is a protein produced by the genus *Phanerochaete*, this protein may be obtained by culturing a genus *Phanerochaete* organism such as *Phanerochaete chrysosporium* on a medium, collecting the culture supernatant, isolating genus *Phanerochaete* endoglucanase from the culture supernatant, and purification. Isolation and purification may be carried out using known protein isolation and purification techniques. Nor is it always necessary to isolate and purify the genus *Phanerochaete* endoglucanase from the culture supernatant. It is also possible to use the culture supernatant directly as the genus *Phanerochaete* endoglucanase. Nor is it always necessary to isolate and purify the genus *Phanerochaete* endoglucanase from the culture supernatant. It is also possible to use the culture supernatant directly as the genus *Phanerochaete* endoglucanase.

The protein of the present teachings is exemplified by proteins having the amino acid sequences set forth in SEQ ID NOS: 4 to 8. The proteins having these amino acid sequences all exhibit a desirable endoglucanase activity under acidic conditions. These are all modified proteins obtained by introducing amino acid modifications into the amino acid sequence in SEQ ID NO:2. In these amino acid sequences, the amino acid mutations (the sites thereof and the substituted amino acid residues) to the amino acid sequence set forth in SEQ ID NO:2 are as shown below. The protein of the present teachings preferably includes one of the amino acid sequences set forth in SEQ ID NOS: 4 to 8, or includes one of these amino acid sequences.

```
SEQ ID NO: 4:      Q107P, G126S, V201A

SEQ ID NO: 5:      S152G, S192L, V201A

SEQ ID NO: 6:      S192L

SEQ ID NO: 7:      K105E

SEQ ID NO: 8:      R171M
```

Of the above, from the standpoint of the degree of improvement in endoglucanase activity under acidic conditions, a protein having the amino acid sequence set forth in SEQ ID NO:4 or SEQ ID NO:5 is preferred.

Endoglucanase Activity

The protein of the present teachings may also exhibit endoglucanase activity that functions even under acidic conditions. Endoglucanase is an endocellulase (EC 3.2.1.4) which hydrolyzes, by an endo action (i.e., at the interior of the molecular chain), the polymer cellulose obtained by the high polymerization of glucose with β-1,4-glucosidic linkages (β-1,4 linkages), to produce cello-oligosaccharides, cellobiose and glucose. Other names for endoglucanase include carboxymethylcellulase, endo-1,4-β-glucanase and endocellulase.

Cellulose exists in nature as a major component of plant cell walls, and is the most commonly produced polysaccharide on Earth. In plant cell walls, cellulose forms crystalline cellulose regions and amorphous cellulose regions. The crystalline cellulose regions form strong crystalline structures by intermolecular hydrogen bonds and the like, and require extremely harsh conditions for synthetic decomposition down to monosaccharides such as glucose. In nature, cellulose is decomposed by microorganisms such as filamentous fungi, and decomposition to glucose by the synergistic action of several kinds of cellulase is known. Moreover, cellulase is a general appellation for enzymes that act to hydrolyze cellulose down to glucose. Types of cellulase include also glucan 1,4-β-glucosidase (EC 3.2.1.74), cellulose 1,4-β cellobiosidase (EC 3.2.1.91) and β-glucosidase (EC 3.2.1.21).

"Acidic conditions" may refer to any pH from pH 2 to 4. Any pH from pH 2.5 to 4 is preferred. "Any pH from pH 2 to 4" means that the protein should have an improved endoglucanase activity at any pH within this pH range, but need not exhibit an improved endoglucanase activity at another pH level within this pH range or outside of this pH range. However, it is acceptable for the protein to exhibit improved endoglucanase activity even outside of this pH range.

"Acidic conditions" more preferably refers to a pH range from pH 2 to 3. That is, a protein which exhibits an improved endoglucanase activity in at least the entire range of pH 2 to 3 is preferred. The presence or absence of endoglucanase activity outside of this pH range is not particularly of concern here. "Acidic conditions" may be set to the entire pH range of pH 2 to 2.5 or the entire pH range of pH 2.5 to 3.

"Exhibiting improved endoglucanase activity" refers, in one aspect, to exhibiting a higher endoglucanase activity than endoglucanase from *Trichoderma reesei* under such acidic conditions. Endoglucanase from *Trichoderma reesei* is an endoglucanase which has is in common use. If the protein is one which exhibits a higher activity under acidic conditions than this endoglucanase, it will be able to saccharify cellulose more efficiently under acidic conditions than the prior art. The acidic conditions in this aspect may be set to any pH from 2 to 4, and preferably to any pH from 2.5 to 4. Alternatively, the acidic conditions may be set as the entire range from pH 2 to 3, the entire range from pH 2 to 2.5, or the entire range from pH 2.5 to 3.

The endoglucanase originating from *Trichoderma reesei* which is used as the basis for comparing endoglucanase activity is exemplified by *Trichoderma reesei* EGII (e.g., GenBank Accession No.: M19373) and *Trichoderma reesei* EGIII (e.g., GenBank Accession No.: AB003694). Of these, it is more preferable for the endoglucanase activity to be improved relative to that of *Trichoderma reesei* EGII.

"Exhibiting improved endoglucanase activity" refers, in another aspect, to exhibiting, under acidic conditions, an endoglucanase activity equal to or higher than that of endoglucanase having the amino acid sequence set forth in SEQ ID NO:2. Endoglucanase having the amino acid sequence set forth in SEQ ID NO:2 exhibits, under acidic conditions, an endoglucanase activity which is more improved than that of conventional endoglucanases such as endoglucanase from *Trichoderma reesei*. Therefore, by having, under acidic conditions, an endoglucanase activity which is equal to or higher than that of endoglucanase having the amino acid sequence set forth in SEQ ID NO:2, the protein of the present teachings can decompose cellulose more efficiently under acidic conditions than in the prior art. The acidic conditions in this aspect may be set to any pH of from 2 to 4, and preferably to any pH from 2.5 to 4. Alternatively, the acidic conditions may be set as the entire range from pH 2 to 3, the entire range from pH 2 to 2.5, or the entire range from pH 2.5 to 3.

Assays to determine whether the endoglucanase activity is improved or not, i.e., assays of the endoglucanase activity, while not subject to any particular limitation, may be carried out using a method that involves reacting the protein with a substrate such as carboxymethyl cellulose (CMC) and measuring the amount of reducing sugar, etc. that arises from decomposition of the substrate. In assays to determine the relative activity with other endoglucanases, the endoglucanase activity of the endoglucanase which is used as the basis for comparing relative activities is preferably carried out under the same conditions (preferably in a simultaneous assay) as the protein being tested.

Examples of the substrate used in assaying the endoglucanase activity include crystalline celluloses such as Avicel (trade name), and amorphous celluloses such as phosphoric acid-swollen Avicel. Water-soluble celluloses that may be used include carboxymethyl cellulose (CMC). Alternatively, the substrate may be β-glucan having both β-1,4 linkages and β-1,3 linkages, such as barley β-Glucan (Sigma Chemical Co., St. Louis, Mo.). The endoglucanase activity in the present teachings is preferably measured using CMC as the substrate. In cases where, for example, the endoglucanase activity is assayed through the cellulose decomposing activity under the cooperative action of a combination of several cellulases, use may be made of a crystalline cellulose or a phosphoric acid-swollen cellulose.

The temperature conditions in reacting the inventive protein with a substrate such as CMC, while not subject to any particular limitation, is preferably any temperature in a range of from 20° C. to 60° C. From the standpoint of the optimal temperature of general endoglucanases, a temperature of about 50° C. is preferred. As described subsequently in the specification, a temperature of about 50° C. is preferred also when the endoglucanase activity of this protein is measured after it has been displayed at the surface of yeast cells. This is because, in addition to being close to the optimal temperature for endoglucanase, there is a need to suppress utilization of the products of cellulose saccharification by the yeast. On the other hand, in assaying the endoglucanase activities of proteins for display at the surface of yeast cells, reaction at from 25° C. to 35° C., or about 30° C., is preferred. This is because endoglucanases exhibiting a high activity at temperatures in which the yeast can survive are preferred. The reaction time, while not subject to any particular limitation, may be set to anywhere from several hours to ten plus hours. The reaction time is preferably set as appropriate for the reaction temperature and the type of substrate, etc. to be used.

There are many methods for quantifying the amount of reducing sugar that forms as a result of the enzyme reaction. Examples include the Somogyi method, the Tauber-Kleiner method, the Hanes method (titration method), the Park-Johnson method, the 3,5-dinitrosalicylic acid (DNS) method and the TZ method (*Journal of Biochemical Methods* 11, 109-115 (1985)). Of these, preferred use may be made of the Somogyi-Nelson method, which employs copper ion reduction with a sugar (*Seibutsukagaku Jikkenhō* 1: Kangentō no Teiryōhō [Experimental methods in biochemistry 1: Methods for the quantitative determination of reducing sugars], $2^{nd}$ Ed., by S. Fukui (Japan Scientific Societies Press, 1990)). In an exemplary protocol according the Somogyi-Nelson method, first an enzyme reaction solution is heat-treated at 100° C. for 10 minutes to stop the reaction, an amount of Somogyi copper solution (available from Wako Pure Chemical Industries, etc.) equal to the amount of the reaction solution is added to the reaction solution and mixed therewith, and the mixture is heat-treated at 100° C. for 10 minutes then rapidly cooled. After cooling, an equal amount of Nelson's reagent (available from Wako Pure Chemical Industries, etc.) is added and the reduced copper precipitate is dissolved, effecting coloration, then left at rest for 30 minutes, following which the absorbance at 660 nm is measured. The amount of reducing sugar is calculated from the measured value using glucose as the standard sugar.

Measurement of the endoglucanase activity can be carried out by supplying the test protein having potential as the present teachings in an assay region composed of a solid-phase body containing a cellulose such as carboxymethyl cellulose, decomposing the cellulose in the solid-phase body within this region, and assaying the endoglucanase activity from the size of the region within the solid-phase body where the cellulose has decomposed and disappeared (referred to as the "halo": the region within the solid-phase body that has become lighter in color or colorless due to biomass decomposition). The size of the halo corresponds to the amount of cellulose decomposition due to the endoglucanase activity.

A halo based on cellulose disappearance in the solid-phase body generally forms as an area that is more transparent than its surroundings, and can be directly confirmed visually or in some other manner. At the time of halo detection, the halo can be clearly detected by dyeing the cellulose with a dye such as Congo Red. Alternatively, when a dye-linked cellulose (e.g., Cellulose Azure, available from Sigma) is used as the biomass, the dye diffuses into the solid-phase body with decomposition of the cellulose, enabling the cellulose decomposing activity to be readily detected. Similarly, by employing a fluorescent dye-linked cellulose as the biomass, a halo can easily be detected. Also, in cases where acid-treated cellulose or the like is used as the biomass, a distinct halo forms due to cellulose decomposition, enabling the cellulose decomposition activity to be easily detected. Carboxymethyl cellulose (CMC) may be used to detect the halo. Alternatively, the reducing sugar which forms as a result of cellulose decomposition may be detected by the DNS method or the Somogyi-Nelson method using CMC or the like as the substrate.

With regard to the decomposition of cellulose, in cases where endoglucanase activity alone does not exhibit a sufficient cellulose decomposing activity, the endoglucanase activity may be assayed by utilizing the cellulose decomposing activity arising from the synergistic effects of concomitant use with cellobiohydralase or the like.

The solid-phase body for halo formation is exemplified by a biomass-supporting gel or film. The material making up the gel or film is not subject to any particular limitation; advantageous use may be made of a natural or artificial polymeric material. Preferred use may be made of agarose (agar) as such a polymeric material. The solid-phase body may be obtained by, for example, suspending or dissolving cellulose that has been purified to some degree as the biomass in an agarose solution, followed by solidification under specific conditions. Alternatively, a powder obtained by drying and pulverizing unpurified biomass may be suspended in an agarose solution, then solidified to give the solid-phase body. No particular limitation is imposed on the morphology of the solid-phase body and the amount of cellulose contained in the solid-phase body, other than the morphology and the amount of cellulose be such as to enable detection of the endoglucanase activity.

When an assay is carried out using such a solid-phase body, the endoglucanase activity may be measured using the inventive protein by itself, or may be measured using cells such as yeast cells in which the inventive protein has been displayed at the cell surface. Display of the protein at the cell surface is described later in this specification.

Assays of the endoglucanase activity may be carried out by suitable combinations of the above-mentioned techniques. For example, the following methods may be used. Improvements in the endoglucanase activity may be detected with any of these methods. The reaction product detecting techniques in each the methods below serve only as examples of the techniques that may be used.

(1) A solution containing a given amount of protein (e.g., about 1 μL) as the test specimen is added to 500 μL of a solution containing 0.5% of a substrate such as CMC and 1% lactic acid, each of which has been adjusted to set the pH at a given level (e.g., the above-described acidic conditions), and the reaction is effected at 30° C. for about 16 hours.

Following the reaction, the amount of reducing sugar can be quantitatively determined by the TZ method (*Journal of Biochemical and Biophysical Methods* 11, 109-115 (1985)).

(2) A solution containing a given amount of protein (e.g., about 1 μL) as the test specimen is added dropwise onto a 1% agar medium containing 0.1% of a substrate such as CMC and 1% lactic acid respective, each of which has been adjusted to set the pH at a given level (e.g., the above-described acidic conditions), and the reaction is effected at 30° C. for 16 to 18 hours.

Following the reaction, the size of the halo that has formed can be measured.

(3) A given amount of protein as the test specimen is added to a substrate solution prepared with a sodium acetate buffer solution to a given pH (e.g., containing 0.5% CMC or β-glucan as the substrate and containing also 1% lactic acid), and the reaction is effected at 50° C. for about 4 hours.

The β-glucan reducing sugar ends that have formed as a result of the reaction are quantitatively measured by, for example, the Somogyi-Nelson method.

Endoglucanase Activity When Protein Is Displayed at Surface of Yeast Cells

When the protein of the present teachings is displayed at the surface of yeast cells, it has a tendency to be stabilized under acidic conditions. The inventors have found that, surprisingly, when the inventive protein is displayed at the surface of yeast cells, there is a tendency for relative improvement in the endoglucanase activity under acidic conditions. That is, the protein of the present teachings tends to have a high activity in a region of about pH 5 that is more weakly acidic than a region of about pH 3, but when the protein is displayed at the surface of yeast cells, it tends to exhibit a higher endoglucanase activity within a lower pH region than the weakly acidic region at about pH 5 (typically, any pH from pH 2 to 4, preferably any pH from pH 2.5 to 4, and more preferably the entire range from pH 2 to 3, the entire range from pH 2 to 2.5 or the entire range from pH 2.5 to 3). Such a tendency is found in proteins having the amino acid sequence set forth in SEQ ID NO:2 and also in variants thereof. Accordingly, this appears to be a property common to proteins of the present teachings.

The protein of the present teachings is thus suitable for use in the decomposition and saccharification of cellulose under acidic conditions. The inventive protein is also useful for display at the surface of yeast cells. That is, when the inventive protein has been displayed at the surface of yeast cells, the cells can be cultured while being induced to produce this protein, in addition to which the protein thus produced has the endoglucanase activity that is stabilized under the acidic conditions. As a result, during reaction for an extended period of time, there is less need for the further addition of endoglucanase and the surface displaying yeast can be repeatedly used.

When the protein has been displayed at the surface of yeast cells, its endoglucanase activity may be assayed using the already described method of assaying the endoglucanase activity of the inventive protein.

The present teachings provide a method of enhancing the acid resistance of the inventive protein by displaying the protein at the surface of yeast cells. That is, a method of enhancing the activity of the inventive protein under acidic conditions by displaying the protein at the surface of yeast cells is also provided. Here, "protein activity under acidic conditions" refers to the inherent activity (e.g., enzymatic activity) of the inventive protein. "Enhancing the protein activity" means to suppress decline in protein activity (e.g., enzymatic activity) and to maintain or improve such activity, even under acidic conditions, by displaying the protein at the surface of yeast cells. The word 'acid' or 'acidic' in such terms as "acidic conditions" and "acid-resistant" used in this embodiment is synonymous with the earlier defined "acidic conditions." In this embodiment, the protein displayed at the surface of yeast cells is preferably a cellulase such as endoglucanase, and more preferably the earlier described protein of the present teachings.

Use of Protein Having Endoglucanase Activity

The present teachings provide a method of producing cellulose decomposition products by decomposing cellulose with the inventive protein.

With the inventive method of producing cellulose decomposition products, cellulose can be efficiently decomposed even under acidic conditions, thus facilitating (by reducing or avoiding the need for neutralizing operations) easier use of product obtained by pretreating cellulose-containing biomass with acid.

The cellulose is exemplified by polymers obtained by the polymerization of glucose with β-1,4-glucosidic linkages, and derivatives thereof. The degree of glucose polymerization is not subject to any particular limitation. Derivatives include those obtained by carboxymethylation, aldehyde conversion, or esterification. Alternatively, "cellulose" may refer to a partial degradation product of cellulose, such as cello-oligosaccharide or cellobiose. Or "cellulose" may refer to β-glucoside (a glycoside), lignocellulose, which is a complex of cellulose with lignin and/or hemicellulose, or may refer to a complex of cellulose with pectin. The cellulose may be crystalline cellulose or amorphous cellulose. Moreover, the cellulose may be of natural origin or may be one that has been artificially synthesized. Nor is there any particular limitation on the source of the cellulose. That is, the cellulose may be of plant origin, fungal origin, or bacterial origin.

Moreover, "cellulose" may refer to a cellulose-containing material which contains any of the foregoing celluloses. Exemplary cellulose-containing materials include natural fiber products such as cotton and linen, reconstituted fiber products such as rayon, cuprammonium rayon, acetate and lyocell; and agricultural waste products such as rice straw, rice hulls and wood chips.

In addition to glucose, the cellulose decomposition product obtained by the method of the present teachings is exemplified by cellobiose and cello-oligosaccharides. In order to efficiently obtain glucose from cellulose, it is preferable to use other types of cellulases, such as β-glucosidase and cellobiosidase, at the same time.

The reaction conditions used in the method of the present teachings may be any conditions that allow the protein of the present teachings to act upon cellulose so as to form cellulose decomposition products. The pH, while not subject to any particular limitation, is preferably 4.5 or less, more preferably from 2 to 4.5, and even more preferably from 2 to 3. Because the inventive protein exhibits an excellent endoglucanase activity even under acidic conditions, it can decompose cellulose under such acidic conditions while suppressing the growth of other types of microorganisms. Moreover, even acid-treated cellulose can be decomposed under conditions in which neutralizing operations for alleviating the degree of acidity thereof is reduced or eliminated entirely. The cellulose decomposition products thus obtained may be used as, for example, the fermentation feedstock for useful substances in much the same way as the conventional glucose.

Polynucleotide Coding for the Inventive Protein

The polynucleotide of the present teachings is a polynucleotide which codes for the protein disclosed in the various above-described embodiments of this specification. Typical examples include polynucleotides coding for the amino acid sequences set forth in the respective SEQ ID NOS: 2, 4, 5, 6, 7 and 8. For example, polynucleotides coding for the amino acid sequence set forth in SEQ ID NO:2 include polynucleotides having the base sequence in SEQ ID NO: 1. Examples include base sequences which hybridize under stringent conditions with a probe composed of all or part of the base sequence in SEQ ID NO: 1, and which code for proteins having an endoglucanase activity. The stringent conditions have already been explained. Additional examples include base sequences which have one or more base deletion, substitution and/or addition with respect to the base sequence set forth in SEQ ID NO: 1, and which code for protein having an endoglucanase activity.

The polynucleotide of the present teachings may be obtained by, for example, chemical synthesis, any of various PCR methods, or the above-described hybridization method. The polynucleotide may be in any suitable form, such as DNA (either double-stranded or single-stranded DNA), RNA, or a DNA/RNA hybrid.

DNA Construct

The DNA construct of the present teachings includes DNA coding for the inventive protein. The DNA construct may take the form of primarily an expression vector intended to transform a suitable host cell. Components of the DNA construct other than the above coding region may be suitably selected according to the method of transformation and the form in which the polynucleotide is retained within the host cell (examples of such forms including a form that is introduced into a chromosome, and a form that is retained outside the chromosomes). The DNA construct may be employed in any of various forms depending on the manner of use. For example, the DNA construct may be used in the form of a DNA fragment, or may be used in a suitable vector form such as a plasmid or cosmid.

Transformant

The transformant of the present teachings may be obtained by transforming a suitable host cell with the above DNA construct. Any of various suitable techniques known to the art may be used for this purpose, including transformation, transfection, conjugation, protoplast fusion, electroporation, lipofection and the lithium acetate method. The cell serving as the host for gene transfer is not subject to any particular limitation. However, taking into account the subsequently described organic acid fermentation, ethanol fermentation and the like, illustrative examples of suitable cells include *Saccharomyces* yeasts such as *Saccharomyces cerevisiae, Schizosaccharomyces* yeasts such as *Schizosaccharomyces pombe, Candida* yeasts such as *Candida shehatae, Pichia* yeasts such as *Pichia stipitis, Hansenula* yeasts, *Trichosporon* yeasts, *Brettanomyces* yeasts, *Pachysolen* yeasts, *Yamadazyma* yeasts, and *Kluveromyces* yeasts such as *Kluveromyces marxianus* and *Kluveromyces lactis*.

The above-described polynucleotide, DNA construct and transformant of the present teachings may be prepared by methods carried out in general accordance with processes described in, for example, *Molecular Cloning, 3$^{rd}$* and *Current Protocols in Molecular Biology*.

Yeast Displaying Endoglucanase at Surface

The inventive yeast displaying endoglucanase at the surface thereof is yeast which retains the protein of the present teachings on the cell surface. By retaining endoglucanase at the surface of yeast cells and decomposing cellulose near the surface of the yeast cells, the yeast is able to rapidly utilize glucose of cellulosic origin.

Because the protein of the present teachings is an extrinsic protein with respect to the yeast, the inventive yeast may serve as one embodiment of the transformant of the present teachings. The manner in which the inventive protein is displayed and retained at the surface of the yeast cells is not subject to any particular limitation. The protein may be retained either directly or indirectly on the surface of the yeast cells.

An example of a method for displaying the protein at the surface of yeast cells involves transforming yeast so that it expresses a fused protein obtained by linking a protein for cell surface display or a secretory protein with the protein of the present teachings. The yeast serving as the host in the surface-displaying yeast is not subject to any particular limitation, although the yeast described above in the "Transformant" section may be advantageously used in the same way here. Moreover, because surface display enables the cellulose to be directly saccharified and utilized, the host of the surface-displaying yeast is preferably a transformant that has been transformed so as to produce a useful substance or a variant. Such transformants, although not subject to any particular limitation, are exemplified by, for lactic acid fermentation, the lactic acid-producing yeasts disclosed in Japanese Patent Application Laid-open Nos. 2003-259878, 2004-187643, 2005-137306, 2006-06271, 2006-20602, 2006-42719, 2006-28318, 2006-296377, 2007-89466 and 2007-175029. However, use is not limited to such transformants as the host for inducing the production of a useful substance in the surface-displaying yeast of the present teachings. The desired useful substance may instead be produced by carrying out some other transformation on the surface-displaying yeast that has been prepared.

In addition to a region coding for the inventive protein, the DNA construct for obtaining the surface-displaying yeast of the present teachings preferably has also a region coding for a protein for cell surface display in the yeast or a region coding for a secretory protein. The protein for cell surface display is exemplified by agglutinating proteins or portions thereof, such as the peptide composed of 320 amino acid residues in the 5' region of the SAG1 gene coding for α-agglutinin, which is a sexual agglutinin. Polypeptides and techniques for displaying the desired protein at the cell surface are disclosed in International Disclosure WO 01/79483, Japanese Patent Application Publication No. 2003-235579, International Disclosures WO 2002/042483 and WO 2003/016525, Japanese Patent Application Publication No. 2006-136223; Fujita et al.: *Appl. Environ. Microbiol.* 70:1207-1212 (2004); Fujita et al.: *Appl. Environ. Microbiol.* 68:5136-5141 (2002)); and Murai et al.: *Appl. Environ. Microbiol.* 64:4857-4861 (1998). By resorting to such methods disclosed in the literature, it is within the ability of those conversant with the art to induce the protein of the present teachings to be displayed at the surface of yeast cells.

When displaying the protein of the present teachings at the surface of cells, by also fusing a secretory protein to the protein for cell surface display, it is sometimes possible to increase the amount of the inventive protein displayed at the cell surface. Illustrative examples of secretory proteins include the secretory signal of the glucoamylase gene of *Rhizopus oryzae*. In some cases, the inventive protein may be displayed at the cell surface by extracellular secretion thereof. In such a case, a DNA construct coding for a fused protein composed of the inventive protein to which the secretory protein has been fused is prepared, and the yeast is transformed by this DNA construct.

The inventive yeast is able to exhibit a relatively good endoglucanase activity under acidic conditions. This is because, as already explained, when the protein of the present teachings is displayed at the surface of yeast cells, there tends to be a relative improvement in the endoglucanase activity under the acidic conditions. Moreover, the yeast of the present teachings is able to exhibit a higher endoglucanase activity than the endoglucanase activity obtained when endoglucanase from *Trichoderma reesei* (which endoglucanase is composed of the amino acid sequence set forth in SEQ ID NO:2) was displayed at the surface of the same yeast cells. Therefore, the yeast of the present teachings may be regarded as being well-suited for cellulose decomposition, saccharification and utilization under acidic conditions (especially from pH 2 to 4).

Other kinds of cellulase, other kinds of cellulose, such as β-1,4-glucan glucosidase, β-glucoxidase and cellobiosidase may also be displayed at the cell surface of the inventive yeast. When doing so, the cellulose may be efficiently saccharified and utilized, particularly in cases where crystalline cellulose is included. Such other kinds of cellulose are known to exist in various types of filamentous fungi and bacteria, including *Trichoderma reesei* and *Phanerochaete chrysosporium*, and may be suitably selected from among these. Other endoglucanases may also be displayed. Methods similar to those for displaying the inventive protein on cell surfaces may be employed for displaying these various types of celluloses at cell surfaces.

Use of Cell Surface Displaying Yeasts

The inventive yeast is well-suited to fermentation involving the decomposition, saccharification and utilization of cellulose under acidic conditions. The manner of fermentation is of no particular concern herein. The type of substance produced by the fermentation in such saccharification and utilization thereof is also of no particular concern. Effective use of the inventive yeast is possible in processes involving the fermentation of a useful substance with yeast. Cellulose can be efficiently utilized even in fermentation under acidic conditions, regardless of the fermentation application. Even in cases where use is made of a cellulosic feedstock from biomass, such as lignocellulose that has been pretreated with acid, it is possible to suppress or avoid having to mitigate the acidity of the feedstock. Moreover, fermentation under acidic conditions enables the growth of other microorganisms to be effectively suppressed.

Examples of fermentation applications include the ethanol fermentation applications inherent to yeasts, and organic acid fermentation applications with yeasts that produce organic acids such as lactic acid. When the yeast of the present teachings is used in the ethanol fermentation application, ethanol may be produced by fermentation involving the direct use of cellulose as the carbon source. When the yeast of the present teachings is used in the organic acid fermentation application, the organic acid may be produced by the direct use of cellulose as the carbon source. Also, when the inventive yeast is used in the organic acid fermentation, even if the pH of the culture medium decreases due to the production of organic acid in the medium, by displaying β-glucosidase and endoglucanase at the surface of the yeasts cells, declines in the activities of these enzymes can be suppressed. As a result, even if the pH of the culture medium decreases on account of the organic acids produced by the organic acid fermentation, the cellulose can continue to be efficiently utilized, thus making it possible to minimize or eliminate the burden of carrying out pH adjusting operations in cellulose saccharification.

In the present specification, "organic acid" refers to organic compounds which exhibit acidity, and are either free acids or their salts. The acidic group in such an "organic acid" is preferably a carboxyl group. Illustrative examples of such "organic acids" include lactic acid, butyric acid, acetic acid, pyruvic acid, succinic acid, formic acid, malic acid, citric acid, malonic acid, propionic acid, ascorbic acid and adipic acid. These "organic acids" may be the stereoisomeric D-form, L-form or DL-form. The "organic acid" is preferably lactic acid, The present teachings provides a method of producing a useful substance with yeast that displays an endoglucanase at a cell surface thereof. The method includes the step of producing the useful substance by culturing, in the presence of cellulose, the yeast of the present teachings which displays endoglucanase on a surface thereof. The cellulose utilized by the yeast in the inventive method of producing a useful substance is synonymous with the cellulose described in the method of producing a cellulose decomposition product. Examples of the cellulose include polymers obtained by polymerizing glucose by means of β-1,4-glucosidic linkages, and derivatives thereof. The degree of glucose polymerization is not subject to any particular limitation. Examples of derivatives include derivatives obtained by carboxymethylation, aldehyde conversion or esterification. Alternatively, the cellulose may be a partial decomposition product, a cello oligosaccharide or a cellobiose. Or the cellulose may be β-glucoside, lignocellulose, which is a complex of cellulose with lignin and/or hemicellulose, or may be a complex of cellulose with pectin. The cellulose may be crystalline cellulose or amorphous cellulose. Moreover, the cellulose may be of natural origin or may be one that has been artificially synthesized. Nor is there any particular limitation on the source of the cellulose. That is, the cellulose may be of plant origin, fungal origin, or bacterial origin.

"In the presence of cellulose" is a condition that is satisfied by the presence of cellulose in the culture medium. Examples of the form of cellulose include, in addition to the above celluloses, natural fiber products such as cotton and linen, reconstituted fiber products such as rayon, cuprammonium rayon, acetate and lyocell; and agricultural waste products such as rice straw, rice hulls and wood chips.

The culture medium used in these embodiments may be any in which the cell surface displaying yeast of the present teachings is capable of utilizing cellulose as the carbon source and is able to grow. The composition of the medium for culturing yeast may be selected as appropriate by one of ordinary skill in the art. The pH of the medium, while not subject to any particular limitation, may be in the range of about pH 4.5 to about 6.5 which is generally used for culturing yeast. From the standpoint of efficiently decomposing cellulose, culturing near the optimal pH for the endoglucanase activity of the inventive protein is preferred. On the other hand, to discourage the growth of other microorganisms, culturing is carried out at preferably pH 4.5 or less, more preferably pH 4 or less, even more preferably pH 3 or less, and still more preferably pH 2.5 or less. The lower the pH, the greater the suppressive effect on the growth of other microorganisms. In particular, at pH 2.5 or below, the growth of other microorganisms can be markedly suppressed. It is preferable to set the pH at about 4.5 to about 6.5 at the start of cultivation, then allow the pH to shift toward the acidic side. When the yeast is an organic acid-producing yeast, organic acids produced by the yeast will lower the pH, causing the above acidic conditions to be attained. Hence, the effect of suppressing the growth of other microorganisms can be achieved even without taking any particular step to acidify the pH. With regard to the culturing temperature and oxygen conditions, any temperature within a range at which the cell surface-displaying yeast is capable of growing is acceptable. The culturing period may be set as appropriate by one of ordinary skill in the art, although continuous culturing for a period of at least 24 hours is preferred.

When the cell surface-displaying yeast of the present teachings is thus cultured in the presence of cellulose, the cellulose is decomposed, yeast growth occurs, and a useful substance such as ethanol or organic acid (when the cell surface-displaying yeast is an organic acid-producing yeast) is produced. With this method, it is possible to efficiently produce useful substances such as ethanol or organic acids from cellulosic biomass as the carbon source without resorting to the use of depletable petroleum resources or food resources.

Screening Method

The inventive method of screening for endoglucanase variants includes the steps of creating a library of test proteins obtained by introducing one or more amino acid modifications into a endoglucanase from *Phanerochaete* spp., or into a variant thereof, and assaying the endoglucanase activities under acidic conditions of the test proteins in the library. With the screening method of the present teachings, by creating a library of novel variants based on endoglucanase from *Phanerochaete* spp. and variants thereof, and assaying the endoglucanase activities under acidic conditions from this library, variants which exhibit excellent endoglucanase activities under acidic conditions can be efficiently obtained.

Preparation of Library

The source protein used for obtaining variants may be any of the various embodiments of the protein disclosed in the present specification. Alternatively, another endoglucanase of from *Phanerochaete* spp. may be used. The endoglucanase from *Phanerochaete* spp. is preferably an endoglucanase from *Phanerochaete chrysosporium*, or a variant thereof. Because the endoglucanase from *Phanerochaete chrysosporium* already exhibits an excellent endoglucanase activity under acidic conditions, screening for endoglucanases of even higher endoglucanase activity can be more efficiently carried out.

The library is composed of natural source proteins found in the natural world and/or variants obtained by introducing new modifications in these naturally occurring proteins (artificial source proteins). The method for obtaining variants is not subject to any particular modification. Molecular evolution technology may be employed as the method for obtaining diverse variants. The test proteins making up the library may have one or more amino acid modifications in the source protein. The number of amino acid modifications is not subject to any particular limitation and may be, for example, from 1 to about 40 modifications, preferably from 1 to about 30 modifications, more preferably from 1 to about 20 modifications, even more preferably from 1 to about 10 modifications, still more preferably from 1 to about 5 modifications, and most preferably from 1 to about 3 modifications. The amino acid modifications may be in the form of amino acid substitutions, deletions or additions, or any combination of two or more of these types of modifications.

The various types of variants may be prepared by the following methods based on molecular evolution technology. First, using error-prone PCR or the like, a modified DNA library is constructed from the DNA of the source protein and, using these various modified DNA molecules, non-cellular protein synthesis is carried out, thereby obtaining a library of variant proteins (variants). These variant proteins are used as at least a portion of the library test proteins in the present screening method. In addition, the non-cellular protein synthesis system which is used may be a protein synthesis system known to the art or one described in Japanese Patent Application Laid-open Nos. 2006-61080 and 2003-116590 filed by the present applicant. By taking the test proteins screened as useful from the library thus constructed, using these test proteins as novel source proteins to construct a new library, and carrying out further screening, it is possible to screen for proteins having an even more useful endoglucanase activity.

At least a portion of the test proteins may be from microorganisms (typically yeasts) which display the test proteins at the cell exterior (especially the cell surface). The endoglucanases from *Phanerochaete* spp., and variants thereof, are stabilized when displayed at the surface of yeast cells, enabling a high endoglucanase activity to be exhibited. For this reason, when the intention is to assay the endoglucanase activity at the time of cell surface display, the library may be constructed by using yeasts which display the test proteins at the cell surface, either together with the test proteins by themselves or in place of the test proteins by themselves.

Measuring the Endoglucanase Activity

One or more method from among the various methods known to the art may be used to measure the endoglucanase activity of the test proteins under acidic conditions. For example, any of the already described methods of measuring the endoglucanase activity of the inventive protein may be suitably selected and used.

For efficient screening or primary screening, it is desirable to detect the halo that forms in accordance with the amount of cellulose decomposition (amount of cellulose disappearance) when cellulose decomposes under the action of the test protein in a solid-phase body containing endoglucanase. This method enables the endoglucanase activity to be easily detected and compared based on the size of the halo.

The form of the cellulose-containing solid-phase body used for assaying the endoglucanase activity is not subject to any particular limitation. For example, to simultaneously measure a plurality of test proteins, a plate-like form on which sufficient assay regions can be formed is preferred. When test protein-containing liquids or the like are furnished as spots arrayed on such a plate-like solid phase body, if a certain test protein has endoglucanase activity, a halo centered on that spot will form.

Assays of the endoglucanase activity are preferably carried out at least under acidic conditions. The acidic conditions employed during such assays are the same as the earlier defined acidic conditions for the inventive protein. That is, in the broadest sense, "acidic conditions" herein refers to any pH in a range of pH 2 to 4. When assaying the endoglucanase activity, aside from the pH, various reaction conditions under which cellulose decomposition can occur are conferred depending on the actions of the test protein. Specifically, individual conditions (e.g., temperature, moisture content, salt concentration, time) at which the target protein will function as an endoglucanase are conferred. Such conditions may readily be obtained by one of ordinary skill in the art.

Measurement of the endoglucanase activity may be carried out under conditions other than the above-described acidic conditions. For example, an assay of the endoglucanase activity under pH conditions ranging from the mildly acidic (pH 5 and above) to the neutral may be carried out in combination with the above assay under acidic conditions. In this way, a pH profile that includes the optimal pH is obtained for the endoglucanase activity of the test protein, enabling more precise and effective screening.

Aside from the test proteins, it is also possible to combine endoglucanase and other types of cellulases and evaluate their endoglucanase activities in terms of their ability to decomposition cellulose through synergistic effects thereof. Combining various types of cellulases is effective for the decomposition or saccharification and utilization of cellulose. It is possible in this way to easily screen for endoglucanases which are suitable for use in combinations of a plurality of cellulases.

Screening based on such synergistic effects may be carried out in place of assays of the endoglucanase activities of individual test proteins, or may be carried out in combination with assays of the endoglucanase activities of individual test proteins.

Moreover, screening based on synergistic effects may be carried out even in cases where combined use of the sort mentioned above is not intended. For example, such use may be carried out in cases where, owing to the type of cellulose and other factors, the cellulose is not sufficiently decomposed by the test protein alone. Moreover, in screening based on synergistic effects, combination with a type of cellulase other than an endoglucanase is effective.

Assays of the endoglucanase activity may be carried out in a state where the protein has been displayed at the surface of microbial cells such as yeast cells. In this way, screening based on the endoglucanase activity at the time of cell surface display is possible. The inventors have found that the inventive protein, when it has been displayed at the surface of yeast cells, for example, is stabilized and exhibits a high endoglucanase activity. Moreover, the usage condition in which endoglucanase is displayed on the surface of yeast cells or the like is one of the most effective configuration in fermenting and producing useful substances via the saccharification of cellulose. Therefore, the screening of test proteins in a cell surface-displayed form is extremely effective. Screening involving the use of such configuration may be carried out alternatively in place of assays of the endoglucanase activities of test proteins by themselves, or may be carried out in combination with the aforesaid assays of the endoglucanase activities of test proteins by themselves.

EXAMPLES

The present teachings is described more fully in the following examples, which are illustrative and should not be construed as limiting the present teachings. The gene recombinations described below were carried out in accordance with *Molecular Cloning. A Laboratory Manual*, by T. Maniatis, et al. (Cold Spring Harbor Laboratory).

Example 1

Cloning of Endoglucanase Gene from *Phanerochaete chrysosporium*:

Because the *P. chrysosporium* gene has a high GC content, amplifying the PCR product was expected to be difficult. It was thus decided to use TaKaRa LA Taq with GC Buffer (Takara Shuzo), which has been optimized for GC-rich templates. The resulting PCR amplification product was cloned in the PCR2.1-TOPO vector using the TOPO TA Cloning Kit (Invitrogen).

Example 2

Gene Recombination

Plasmid DNA was introduced into *Escherichia coli* using the Z-Component *E. coli* Transformation Kit (Zymo Research) or ECOS Competent *E. coli* DH5α (Nippon Gene). QIAprep Spin Miniprep Kit (50) (Qiagen) was used for plasmid extraction from *E. coli*. Purification of the gene fragments was carried out by electrophoresis in a 1% agarose gel, followed by recovery and purification from the gel using the Zymoclean Gel DNA Recovery Kit (Zymo Research). The LigaFast Rapid DNA Ligation System (Promega) was used for the ligation reaction. Restriction enzymes produced by Takara Shuzo were used.

Example 3

Construction of *P. chrysosporium* cDNA Library

*P. chrysosporium* (ATCC64314) cells were inoculated into 50 mL of modified Vogel's medium 9 (0.01 M dimethyl succinate buffer (pH 4.5), 0.23 g/L $NH_4H_2PO_4$, 0.068 g/L veratryl alcohol, 0.2% (w/v) Avicel (microcrystalline cellulose: Avicel PH-101, Asahi Kasei)) within a 500 mL Erlenmeyer flask, and static cultured at 30° C. for four days. The cells that had grown were collected by centrifugal separation, and rapidly cooled with liquid nitrogen. The frozen cells (wet weight, 120 mg) were placed in a mortar and mechanically disrupted for about 10 minutes with a pestle while maintaining the frozen state by pouring in liquid nitrogen. The total RNA was extracted from the disrupted cells using a RNeasy Plant Mini Kit (Qiagen). When DNase treatment was not carried out at the time of RNA extraction, genomic DNA admixture occurred, resulting in the amplification of intron-containing genomic DNA in the next PCR reaction. This problem was resolved by using total RNA eluted from the column following on-column DNase treatment (an optional protocol). Using the reverse transcriptase from a TaqMan Reverse Transcription Reagents kit (Applied Biosystems), cDNA was synthesized from the resulting total RNA as the template.

Example 4

Subcloning of Pccel12A Gene

The secretory signal sequence of Pccel Pccel12A was predicted using the PSORT II Prediction program, and a DNA sequence coding for the mature protein excluding the 22 amino acids at the N-terminus was PCR amplified. The PCR primers used had the following sequences.

```
Sac-Pccel12A-F (SEQ ID NO: 9):
CCGCGGagatcacaggacagtacgactgcattcctgc

Xho-Pccel12A-R (SEQ ID NO: 10):
CTCGAGccaacgttgactgcgactgcgaaactctctg
```

(Here, portions in capital letters indicate, respectively, the SacII and XhoI recognition sequences, and underlined portions indicate homologous sequences in the Pccel12A gene. The two bases therebetween are insertion sequences for aligning the reading frames.)

Using the synthesized cDNA as the template, a Pccel12A gene fragment (0.64 kb) was amplified, and subcloned in the PCR2.1-TOPO vector. Of the clones obtained, full-length base sequences for three clones were found, when sequenced, to be sequences homologous with Pccel12A (AY682744). However, in all three clones, 8 amino acids absent in AY682744 were discovered to have been inserted, in addition to which the 10 amino acid sequence immediately following the inserted sequence had been substituted (see the comparison in FIG. 1 between the cloned Pccel12A and the database sequence). Because these inserted and substituted sequences were common to the three clones, it was concluded that this is a sequence specific to the ATCC64314 strain used in this procedure, and a decision was made to use the sequence as is. In addition, Pccel 12A (AY682744) was produced based on the cDNA thus obtained.

Example 5

Editing of Pccel12A Gene Sequence

The plan had been to cut away the cloned Pccel12A gene with SacII-XhoI and insert it into an integration vector. However, because the XhoI sequence was contained within the above insertion sequence, the scheme shown in FIG. 2 was used to remove the XhoI sequence without altering the amino acid sequence.

Two DNA fragments from which the XhoI sequence had been removed with KOD plus DNA polymerase were amplified using two primer sets (Sac-Pccel12A-F with Pccel12A+200R, Pccel12A+171F with Xho-Pccel12A-R), and purified by agarose gel electrophoresis. The DNA sequences of the primers uses were as follows.

composed of 0.2 μL of Pyrobest DNA polymerase (Takara Shuzo), 5 μL of 10x reaction buffer, 4 μL of 25 mM dNTP, 0.25 μL of 100 pmol/μL primer F, 0.25 μL of 100 pmol/μL primer R and 20 ng of template DNA, to which sterilized and distilled water was added to a volume of 50 μL. The PCR reactions included 5 minutes of reaction at 94° C., followed by 30 reaction cycles of 30 seconds at 94° C., 30 seconds at 60° C. and 2 minutes at 72° C. each, then followed by 7 minutes of reaction at 72° C. The resulting PCR amplified product was purified using a GFXPCR DNA and Gel Band Purification Kit (Amersham Bioscience) according to the method described in the instructions. After purification, the end sequences were cleaved with the restriction enzymes NdeI and XhoI, ligation reactions were carried out using pET23b (Novagen) similarly cleaved with NdeI and XhoI and using the DNA Ligation Kit "Mighty Mix" (Takara Shuzo), and the resulting plasmids were introduced into *E. coli* DH5α. The respective plasmid DNAs were extracted from the resulting transformed *E. coli* and subjected to base sequence analysis, from which it was confirmed that each EG gene had been correctly subcloned.

TABLE 2

| | F primer | R primer |
|---|---|---|
| Pccel 12A | AAACATATggCACAgACTATCACAggACA (SEQ ID NO: 13) | AAACTCgAgTCAAACgTTgACTgCgACTgCgA (SEQ ID NO: 14) |
| TrEg II | AAACATATgCAgCAgACTgTCTggggCCAgT (SEQ ID NO: 15) | AAACTCgAgCTACTTTCTTgCgAgACACgAgCT (SEQ ID NO: 16) |
| TrEg III | AAACATATgCAAACCAgCTgTgACCAgTg (SEQ ID NO: 17) | AAACTCgAgTTAgTTgATAgATgCggTCCAggA (SEQ ID NO: 18) |

Pccel12A + 200R (SEQ ID NO: 11):
gagctacgcgaacctagagcacaacaccgc

Pccel12A + 171F (SEQ ID NO: 12):
gcggtgttgtgctctaggttcgcgtagctc (By changing c to a and a to t in each of the sequences in the underlined portions, the XhoI sequence was removed without altering the amino acid sequence.)

With the two DNA fragments as the templates and using the primers Sac-Pccel12A-F and Xho-Pccel12A-R, overlap PCR was carried out with KOD plus DNA polymerase, thereby synthesizing full-length Pccel12A. The amplified fragments obtained were subcloned in the PCR-BLUNT II TOPO vector using the Zero BLUNT TOPO PCR Cloning Kit, and the sequences were determined with a DNA sequencer, whereupon it was confirmed that the XhoI sequence at the interior was removed as intended.

Example 6

Subcloning the Endoglucanase Gene in a Plasmid (pET23b):

The following four genes were used as endoglucanase genes: the Pccel 12A ATCC64314 gene from *P. chrysosporium* that was newly obtained in Example 1, Pccel 12 A AY682744, and Tr EGII (Accession No. M19373) and Tr EGIII (Accession No. AB 003694) from *T. reesei*. Using the primers shown in Table 2 (SEQ ID NOS: 13 to 18), in which an NdeI restriction enzyme site was added to the 5' end of the mature protoin portion cDNA of the respective genes and an XhoI restriction enzyme site was added to the 3' end, the DNA fragments were amplified by PCR. The reaction solution was

Example 7

Homology Search in Pc-cel 12 (ATCC64314)

Figure 3:
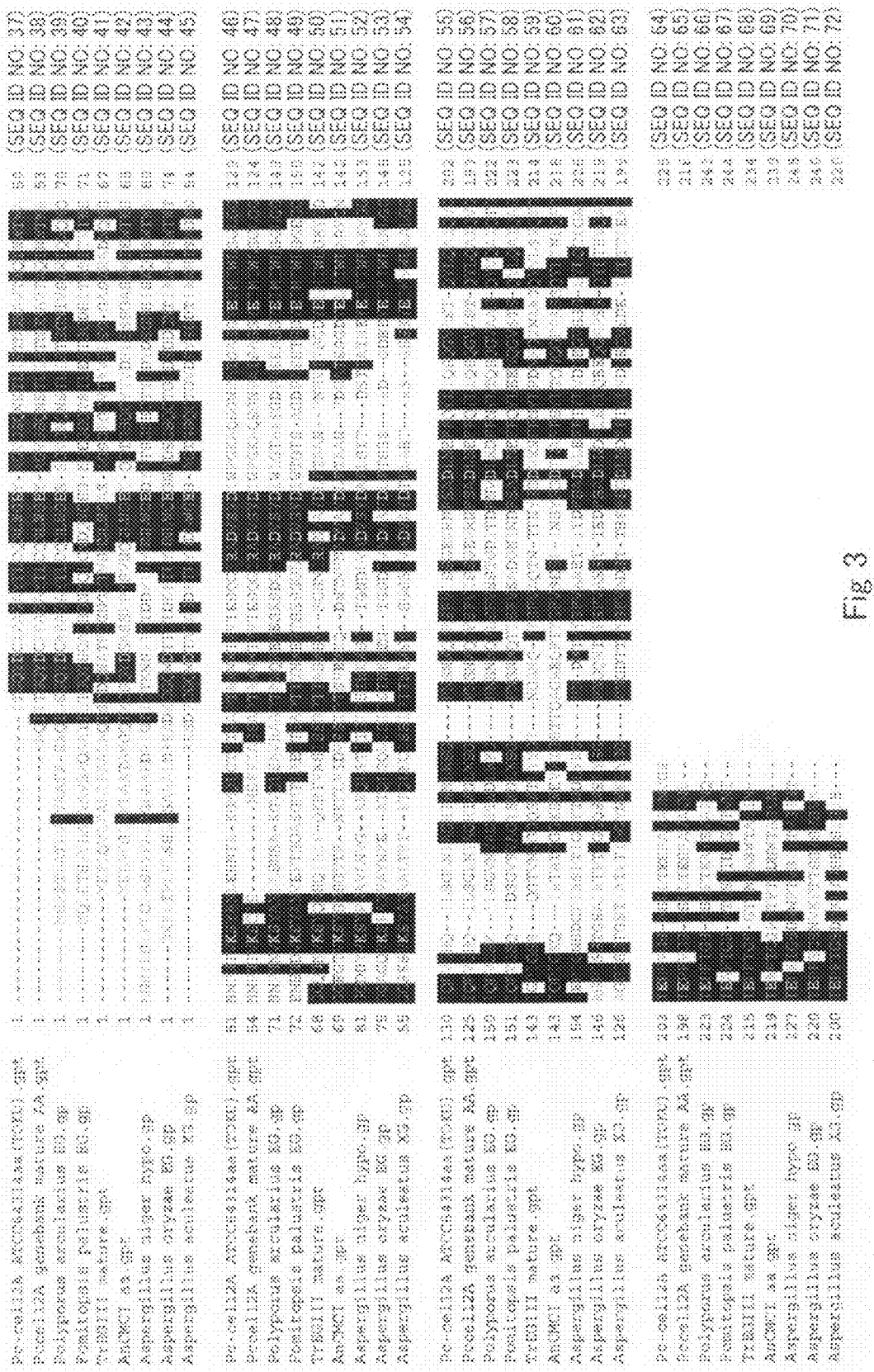
FIG. 3 shows the results of amino acid alignments between protein from the Pccel 12A ATCC64314 obtained and other endoglucanases.

Based on the results of a BLAST search of Pccel 12A (Pc-cel12A ATCC64314aa(TOKU).gpt), the protein having the highest homology was the protein encoded by AY682744 (Pccel12A genebank mature AA.gpt), which had a homology of 92%. The protein having the next highest homology (70%) was dbj BAD98315.1 from *Polyporus arcularius* EG. Next, dbj BAF49602.1 from *Fomitopsis palustris* EG had a homology of 60%. FIG. 3 shows the alignment results.

As shown in FIG. 3, the homology with EGIII (Tr EGIII) from *T. reesei* was 37%, the homology with AnCMCI (Accession No. CAA03652) and *Aspergillus nigar* hypo (Accession No. XP_001390433) was 42%, the homology with *Aspergillus orizae* EG (Accession No. BAE58022) was 42%, and the homology with *Aspergillus aculeatus* XG (Accession No. AAO20340) was 43%.

The amino acid sequence (SEQ ID NO:2, Pccel 12A ATCC64314aa(TOKU)) of the endoglucanase obtained in this example differed completely, in the surrounding portion (18 amino acid residues (SEQ ID NO:3)) in FIG. 3, from the amino acid sequence of the already known Pccel 12A from *Phanerochaete chrysosporium* (Accession No. AY 682744). With regard to homologous proteins other than this known amino acid sequence, a comparison of the surrounding portions thereof showed good homology with homologous proteins such as those of *Polyporus arcularius* EG and *Fomitopsis palustris* EG. As for the amino acid sequence known as Pccel 12A, the activity of the cloned protein is unknown. Based on the above, the protein obtained here was found to be a first Family 12A type endoglucanase cloned from *Phanero-*

*chaete chrysosporium*. Compared with the Tr EGIII and AnC-MCI, for which the activity of the cloned protein has already been investigated, the amino acid sequence homology was only about 40%, which appeared to indicate that this was a different kind of protein.

Example 8

Amplification of Non-Cellular Protein Synthesis Template DNA of Endoglucanase Gene DNA fragments employed for non-cellular protein synthesis were amplified using as the template the expression vector pET23b inserted with the respective endoglucanase genes. That is, using the respective plasmids created in Example 6 as the templates, sequences from the F1 primer (ATCTCGATC-CCGCGAAATTAATACGA) (SEQ ID NO: 19) to the R1 primer (TCCGGATATA GTTCCTCCTT TCAG) (SEQ ID NO:20) were amplified by PCR. The target band was cut away and ethanol precipitated following agarose gel electrophoresis, then used as the template for the transcription/translation reaction. The PCR reaction solution was composed of 0.5 μL LA Taq (Takara Shuzo), 5 μL 10× reaction buffer, 4 μL 2.5 mM dNTP mix, 4 μL 25 mM $MgCl_2$, 0.5 μL 100 pmol/μL primer F, 0.5 μL 100 pmol/μL primer R, and 50 ng template DNA, to which sterilized and distilled water was added to a volume of 50 μL. The PCR reactions included 5 minutes of reaction at 94° C., followed by 30 reaction cycles of 30 seconds at 94° C., 30 seconds at 60° C. and 2 minutes at 72° C. each, then followed by 7 minutes of reaction at 72° C. The amplified DNA fragments all had on the 5' side a T7 promoter sequence (AATACGACTCACTATA; SEQ ID NO:21) and a ribosome binding site (AAGGAG). Translation begins from ATG at the NdeI site, a cDNA sequence corresponding to the respective endoglucanase mature proteins continues thereafter, and there is an XhoI site after the termination codon. In addition, the DNA has been designed so as to have a T7 termination sequence (CTAGCATAACCCCTTGGGGC-CTCTAAACGGGTCTTGAGGGGTTTTTTG) (SEQ ID NO:22) on the 3' side. The base sequences of the amplified regions (Pccel 12A ATCC64314, Tr EGII, Tr EGIII, and Pccel 12A AY682744) (SEQ ID NOS: 23, 25, 27 and 29) are shown in FIGS. 4 to 7.

Example 9

Non-Cellular Synthesis of Respective Cellulase Proteins and Measurement of Their Activities Two microliters of the respective PCR products of Pccel 12A ATCC64314, Pc-cel 12A AY682744, Tr EGII and Tr EGIII bonded downstream from the T7 promoter sequence as the template was added to 8 μL of a non-cellular protein synthesis reaction solution of a specific composition (20 mg/mL of *E. coli* s30 extraction, 56.4 mM Tris-acetate (pH 7.4), 1.2 mM ATP, 1.2 mM ATP, 1 mM GTP, 1 mM CTP, 1 mM UTP, 40 mM creatine phosphate (pH 7.4), 0.7 mM 20-amino acid mix, 4.1% (w/w) polyethylene glycol 6000, 35 μg/mL folinic acid, 0.2 mg/mL *E. coli* tRNA, 36 mM ammonium acetate, 0.15 mg/mL creatine kinase, 10 mM magnesium acetate, 100 mM potassium acetate, 10 μg/mL rifampicillin, 7.7 μg/mL T7 RNA polymerase), and a transcription-translation coupling reaction was carried out.

One microliter of each of the above synthesis products and 1 μL of each of the synthesis products obtained in control wells were added to 500 μL of a 0.5% CMC, 1% lactic acid solution adjusted to, respectively, pH 2.0, pH 2.5, pH 3.0, pH 4.0, pH 5.0, pH 6.0 or pH 7.0, and reacted at 30° C. for 16 hours. Following reaction, the amount of reducing sugar was quantitatively determined by the TZ method (*Journal of Biochemical and Biophysical Methods*, 11 (1985)). Next, the relative activity, based on a value of 100% for the amount of reducing sugar at the pH level where the activity was highest, was determined for each protein. The results are shown in FIG. 8.

Figure 8:
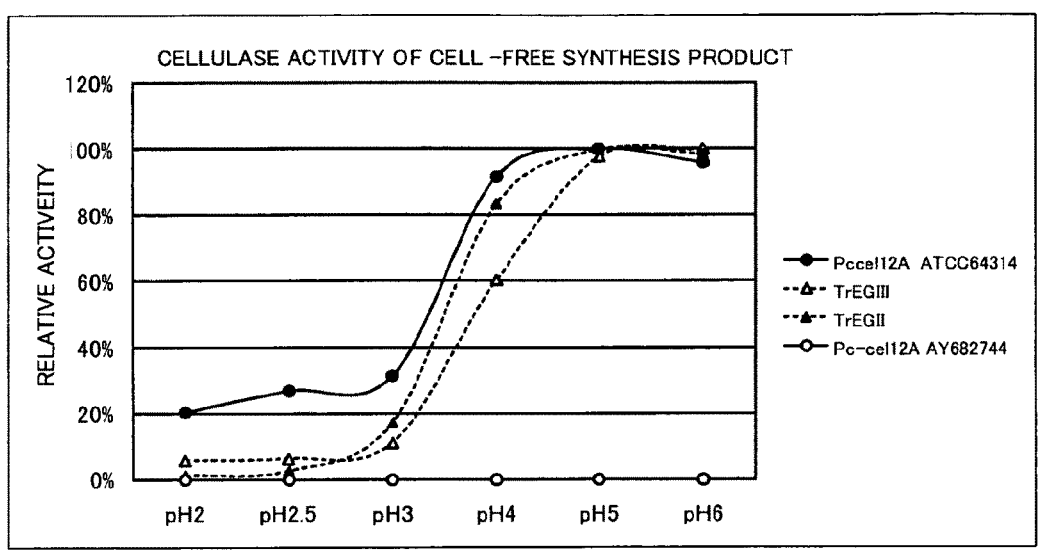
FIG. 8 shows the relative activities based on the amount of reducing sugar at various pH levels for the products of cell-free protein synthesis.

As shown in FIG. 8, Pccel 12A ATCC64314 exhibited a high acid resistance compared with Tr EGII and Tr EGIII. Pc-cel 12A AY682744 was not observed to form reducing sugars at any of the pH levels.

Example 10

In addition, each of the synthesis products obtained in Example 9 was deposited dropwise on top of a 1% agar medium containing 0.1% CMC and 1% lactic acid, adjusted to, respectively, pH 2.0, pH 2.5, pH 3.0, pH 4.0 or pH 5.0, and reacted at 30° C. for a period of from 16 to 18 hours. Following the reaction, staining solution (1% Congo Red, 1 M Tris-HCl (pH 9.0)) was deposited dropwise onto the agar, and a staining reaction was carried out for 30 minutes. Next, the staining solution was removed, and 1 M NaCl were deposited dropwise thereon, thereby decolorizing the endoglucanase reacted areas. The decolorizing reaction was carried out until halos formed. An image of the plate on which halos had formed was taken with a digital camera, following which the image was digitized using image processing software and black-and-white inversion was carried out. The halo areas in the resulting image were digitized by densitometer analysis (NIH Image 1.6). The densitometer reading for Pccel 12A ATCC64314 at pH 2.0 was set to an arbitrary value of 1, relative to which the densitometer readings for each halo were calculated, thereby determining the relative activities. The results are shown in FIG. 9.

Figure 9:
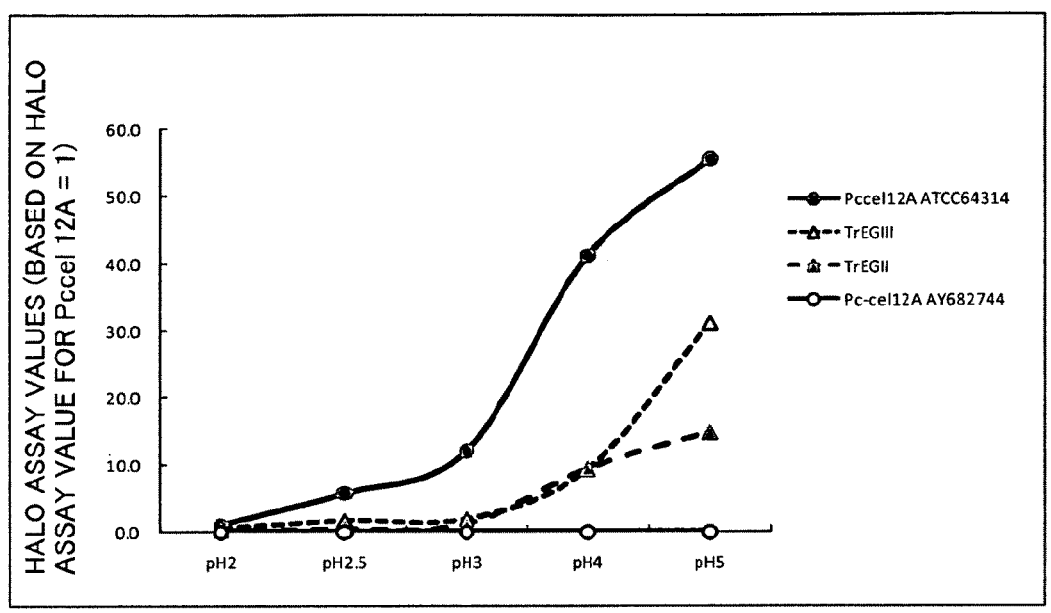
FIG. 9 shows relative activities based on halo assays at various pH levels for the products of cell-free protein synthesis.

As shown in FIG. 9, Pccel 12A ATCC64314 showed the highest activity throughout the entire range of pH 2 to 5. On the other band, Pc-cel 12A AY682744 did not form any halos whatsoever. From the above, it was apparent that the protein encoded by Pc-cel 12A AY62744 has no cellulase activity. At the same time it became apparent that the protein encoded by Pccel 12A ATCC64314 obtained here was a novel cellulase which has a high endoglucanase activity and a high acid stability compared with known cellulase proteins. Moreover, in comparing the amino acid sequences, because the homology with the protein having the highest degree of identity thereto, *Polyporus arcularius* endoglucanase (dbj BAD98315.1), was 70%, in terms of the amino acid sequence as well, this was clearly an endoglucanase new to the literature.

Example 11

Construction of Variant DNA Library for Pccel 12A ATCC64314 Gene:

Using as the template the DNA obtained by inserting Pccel 12A ATCC64314 into the expression vector pET23b, the amplification of DNA fragments for use in non-cellular protein synthesis was carried out. That is, using the plasmid prepared in Example 6 as the template, a variant DNA library in which an average of 0.5 modification per 100 bases (error rate, 0.5%) had been randomly introduced was created by amplifying the sequence from the F1 primer (ATCTCGATC-CCGCGAAATTAATACGA) (SEQ ID NO:19) to the R1 primer (TCCGGATATAGTTCCTCCTTTCAG) (SEQ ID NO:20) by error-proof PCR (10 mM Tris-HCl (pH 9.0), 50 mM KCl, 0.1% TRITON X-100, 5 to 10 mM $MgCl_2$, 0.5 to 2.0 mM $MnCl_2$, 0.2 mM dATP, 0.2 mM dGTP, 1 mM dCTP, 1 mM dTTP, 1 to 100 ng/μL MnP, 0.3 μM primer, 25 mU/μL Promega Taq DNA polymerase).

Example 12

Non-Cellular Synthesis of Variant Proteins from Variant Protein Library of Pccel 12A ATCC64314 Gene The wells of the variant protein library constructed in Example 10 were diluted to an average of 2 molecules/well, after which LA Taq polymerase was used to carry out RCR reactions including reaction at 94° C. for 2 minutes, followed by 65 reaction cycles of 10 seconds at 96° C., 5 seconds at (Tm-5)° C. and 1 minute at 72° C. each, then followed by 7 minutes of reaction at 72° C. Using 2 μL of the respective PCR products as the templates, 8 μL of a non-cellular protein synthesis reaction solution of a specific composition (20 mg/mL E. coli s30 extract, 56.4 mM Tris-acetate (pH 7.4), 1.2 mM ATP, 1.2 mM ATP, 1 mM GTP, 1 mM CTP, 1 mM UTP, 40 mM creatine phosphate (pH 7.4), 0.7 mM 20 amino acid mix, 4.1% (w/w) polyethylene glycol 6000, 35 μg/mL folinic acid, 0.2 mg/mL E. coli tRNA, 36 mM ammonium acetate, 0.15 mg/mL creatine kinase, 10 mM magnesium acetate, 100 mM potassium acetate, 10μ/mL rifampicillin, 7.7 μg/mL T7 RNA polymerase) was added, and a transcription-translation coupling reaction was carried out, thereby constructing a library of variant proteins.

Example 13

Screening (1) for High-Activity Variant Proteins from the Pccel 12A ATCC64314 Gene One microliter of the respective synthesis products obtained in the respective wells in Example 11 were added dropwise onto a 0.1% carboxymethyl cellulose (CMC) and 1% lactic acid-containing 1% agar media adjusted to, respectively, pH 2.0 or 2.5, and reacted at 30° C. for a period of 16 to 18 hours. Following the reaction, a staining solution (1% Congo Red, 1 M Tris-HCl (pH 9.0)) was deposited in a dropwise manner on the agar, and the staining reaction was carried out for 30 minutes. The staining solution was then removed, and 1 M NaCl was deposited dropwise. The relative activity was determined from the size of the halos that formed, based on which the endoglucanase activity was assayed (primary screening). Determinations of relative activity based on the halo size were carried out in the same way as in Example 10.

The endoglucanase activities for 9,216 samples prepared in Example 12 were assayed, from which Variant Proteins 3, 4, 5, 19 and 93 were obtained as high-activity variant proteins.

Example 14

Screening (2) for High-Activity Variant Proteins from the Pccel 12A ATCC64314 Gene The variant proteins obtained in Example 12 were added dropwise onto 0.1% CMC, 1% lactic acid-containing 1% agar media adjusted to, respectively, pH 2.0, 2.5, 3.0, 4.0 or 5.0, the relative activities were determined from the sizes of the halos in the same manner as in Example 12, and the endoglucanase activities were assayed (secondary screening). At the same time, non-cellular protein synthesis was carried out for Pccel 12 A ATCC6431, Tr EGII and Tr EGII as well, and the endoglucanase activities were assayed. The results are shown in FIGS. 10 and 11.

Figure 10:
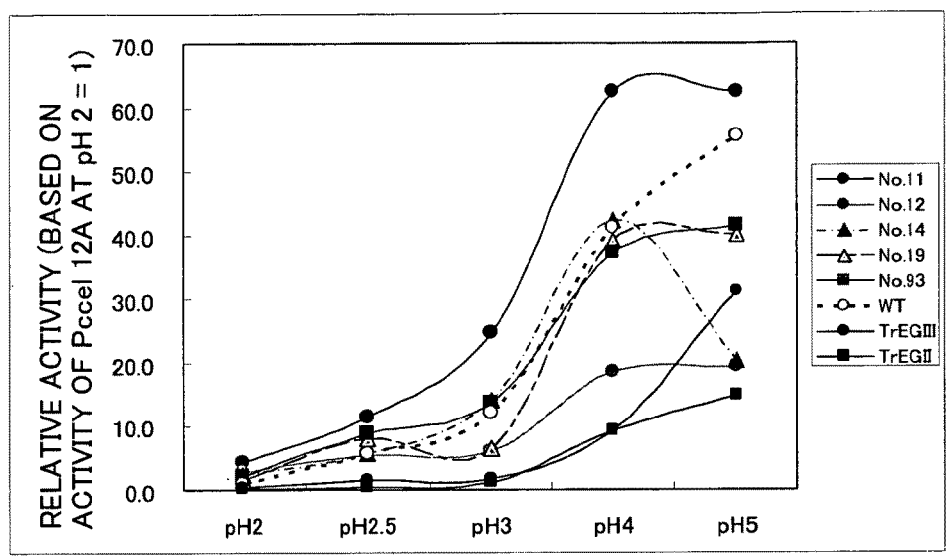
FIG. 10 is a graph showing the results of secondary screening by halo assays on primary screened variants.

As shown in FIGS. 10 and 11, compared with prior to modification (Pccel 12A ATCC64314), the relative activities of the respective endoglucanases rose for each of the variant proteins. That is, compared with Pccel 12A ATCC64314 prior to modification, these variants clearly showed a rise in relative activity at pH 4 and below, more so at pH 3 and below, and even more so at pH 2.5 and below. It can be seen that Variant Protein 11 rose 4.4-fold at pH 2.0, 2-fold at pH 2.5, 2-fold at pH 3.0, and 1.5-fold at pH 4.0. Variant Protein 12 rose 2.8-fold at pH 2.0, and Variant Protein 14 rose 2.3-fold at pH 2.0. Variant Protein 19 rose 1.4-fold at pH 2.0. Variant Protein 93 rose 2.2-fold at pH 2.0, and rose 1.6-fold at pH 2.5.

As is apparent from FIGS. 1 and 2, compared with EGII and EGIII from Trichoderma reesei, these variant proteins have high relative activities at pH 4 and below, more so at pH 3 and below, and even more so at pH 2.5 and below.

The amino acid sequences of Variant Proteins 11, 12, 14, 19 and 93 were determined, revealing the sequences shown in SEQ ID NOS: 4 to 8. The number of modifications in the respective variant proteins are shown in FIG. 12.

Example 15

Figure 13:
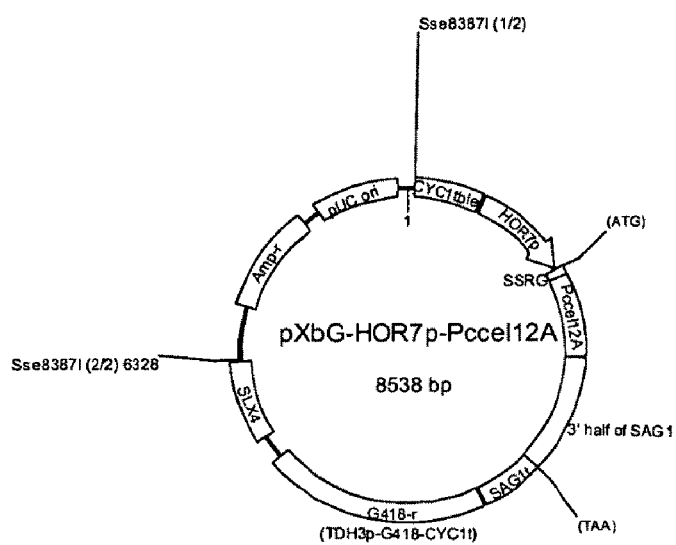
FIG. 13 shows the structure of a chromosome integration vector used for displaying Variant 11 at the surface of yeast cells.

Display of Endoglucanase from Phanerochaete chrysosporium and Variants Thereof on Yeast Surface In this example, a plasmid for displaying Pccel 12A ATCC64314 on the surface of yeast cells was constructed and used to transform the yeast, and the Pccel 12A ATCC64314 endoglucanase activity at the yeast surface was assayed. The plasmid for surface display was constructed as follows. A plasmid was constructed by the ligation of DNA coding for the subcloned Pccel 12A ATCC64314 fragment or the Variant Protein 11 gene fragment obtained in Example 1 downstream from the DNA coding for the HOR7 promoter of S. cerevisiae, and by providing even further downstream the 3' side of the SAG 1 gene of S. cerevisiae and DNA coding for the SAG1 terminator. The constructed plasmid DNA (pXbG-HOR7p-Pccel 12A) is shown in FIG. 13.

The DNA obtained by cleaving the constructed plasmid DNA with the restriction enzyme Sse 83871 was integrated into the bleomycin-resistant gene region of the BGL strain (the yeast T165 strain (transformed so as to express L-lactic acid synthetase), mentioned in Japanese Patent Application No. 2002-362891, which displays on the surface thereof a β-glucosidase gene from Phanerochaete chrysosporium), thereby creating the Pccel 12A strain and the Pccel 12A-M11 strain which display, respectively, Pccel 12A ATCC64314 and the Variant Protein 11 thereof at cell surfaces. The strains in which the genes had been introduced were selected by G418.

Figure 14:
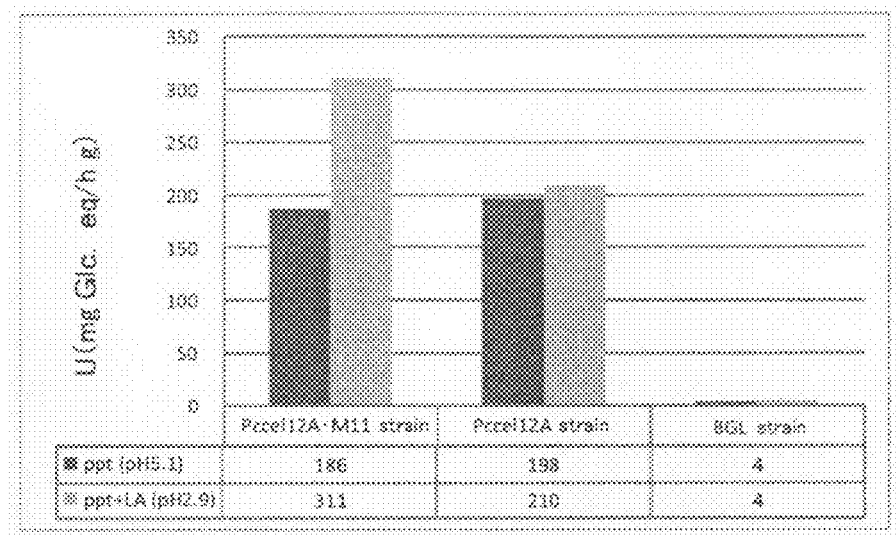
FIG. 14 shows the results of measurements of the cellulase activity in the surface-displaying yeasts that were created.

The Pccel 12A strain and Pccel 12A-M 11 strain thus created were cultured for 2 days on a YPD medium. Following recovery of the yeast cells from the culture broth by centrifugal separation, the cells were washed three times with sterilized water. The cells were then added to a Substrate Solution 1 (0.5% β-glucan, 1% lactic acid, 25 mM sodium acetate, pH 2.9) or a Substrate Solution 2 (0.5% β-glucan, 25 mM sodium acetate, pH 5.1) to OD 10. Following cell addition, the enzyme reaction was carried out at 50° C., and the cellulase activities (,-glucosidase and endoglucanase activities) were measured by using the Somogyi-Nelson method to determine the amount of β-glucan reducing sugar ends that had formed 4 hours later as a result of reaction. The BGL strain was similarly cultured, and the cellulase activities measured. The results are shown in FIG. 14. In FIG. 14, 1 U signifies one unit, which is defined as the formation of 1 mg of reducing sugar (glucose equivalent) per gram of cells per hour of reaction. The β-glucan used in this example was barley β-glucan (Sigma Chemical Co.; St. Louis, Mo.), which is a soluble straight-chain polysaccharide composed on average of 1,200 glucose units. Of the bonds between glucose units, 70% are β(1-4) bonds and 30% are β(1-3) bonds.

As shown in FIG. 14, when Substrate Solution 1 (pH 2.9) was used, the Pccel 12A-M11 strain exhibited a higher activity than the Pccel 12A strain. Also, it was apparent that the Pccel 12A-M11 strain exhibited a higher activity when Substrate Solution 1 (pH 2.9) was used than when Substrate Solution 2 (pH 5.1) was used. Specifically, with the Pccel 12A strain, the activity at pH 2.9 was 94% of the activity at pH 5.1; with the Pccel 12A M11 strain, the activity at pH 2.9 was 148% of the activity at pH 5.1. In addition, the Pccel 12A protein synthesized by the non-cellular synthesis method had an activity at pH 3.0 which was 31% of the activity at pH 5.0, and the Pccel 12A M11 protein synthesized by the non-cellular synthesis method had an activity at pH 3.0 which was 44% of the activity at pH 5.0 (see FIG. 15). That is, the variant protein M11 displayed at the surface of yeast cells shows a tendency to differ from the endoglucanase activity pH profile for the variant protein M11 by itself that is shown in Example 13 and in the subsequently described Example 16. Also, the Pccel 12A strain had substantially the same cellulase activities in both Substrate Solution 1 and Substrate Solution 2. From the above, it became apparent that variant protein M11, by being displayed at the surface of yeast cells, is further stabilized under acidic conditions and exhibits a high endoglucanase activity, and that it exhibits a high cellulase activity by cooperating with β-glucosidase. Such a modification in the pH profile was likewise observed in the Pccel 12A strain. These findings suggest that the modification in the pH profile when displayed at the surface of yeast cells, namely the improvement in acid resistance, is a characteristic common to Pccel 12A and variants thereof. Proteins displayed at the surface of yeast cells were all found to have a higher acid resistance than proteins synthesized by a non-cellular synthesis method.

Example 16

Cellulase Activity of Modified Enzyme

Two microliters of, as templates, the respective PCR products obtained by bonding the genes for Pccel 12A, Pccel 12A variant 11, *Trichoderma reesei* EGII or *Trichoderma reesei* EGIII downstream of the T7 promoter sequence were added to 8 μL of a non-cellular protein synthesis reaction solution of a specific composition (20 mg/mL *E. coli* s30 extract, 56.4 mM Tris-acetate (pH 7.4), 1.2 mM ATP, 1.2 mM ATP, 1 mM GTP, 1 mM CTP, 1 mM UTP, 40 mM creatine phosphate (pH 7.4), 0.7 mM 20-amino acid mix, 4.1% (w/w) polyethylene glycol 6000, 35 μg/mL folinic acid, 0.2 mg/mL *E. coli* tRNA, 36 mM ammonium acetate, 0.15 mg/mL creatine kinase, 10 mM magnesium acetate, 100 mM potassium acetate, 10 g/mL rifampicillin, 7.7 μg/mL T7 RNA polymerase), and a transcription-translation coupling reaction was carried out, thereby synthesizing various proteins. One microliter of each of the synthesis products was added to 500 μL of a 0.5% CMC, 1% lactic acid solution adjusted to, respectively, pH 2.0, 2.5, 3.0, 4.0, 5.0, 6.0 or 7.0, and reacted at 30° C. for 16 hours. Following reaction, the amount of reducing sugar was quantitatively determined by the TZ method (*Journal of Biochemical and Biophysical Methods*, 11 (1985), 109-115). The results are shown in FIG. 15.

Figure 15:
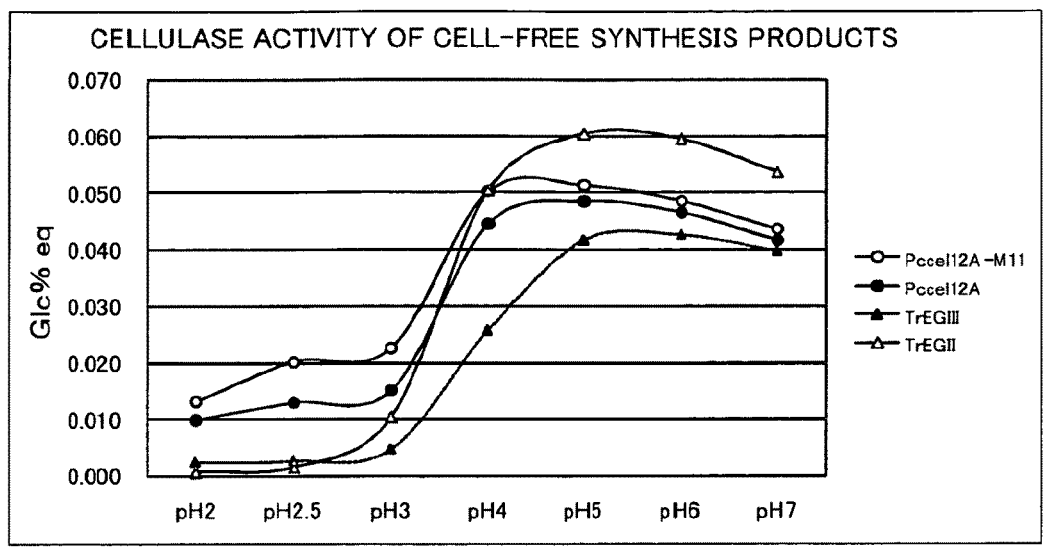
FIG. 15 shows the results of measurements by the TZ method of the endoglucanase activities of various proteins synthesized in cell-free synthesis systems.

As shown in FIG. 15, as with the results of the halo assays in Example 14, Pccel 12A Variant 11 exhibited a higher endoglucanase activity than Pccel 12A over the entire pH range of 2 to 7. Pccel 12A Variant 11 exhibited a high endoglucanase activity particularly at pH levels of from 2 to 4, more particularly at pH levels of 3 and under, and most particularly at pH levels of 2.5 and under.

From above Examples 13 to 16, variants of endoglucanase from *Phanerochaete chrysosporium*, particularly Variant 11, were found to have higher endoglucanase activities than Pccel 12A and endoglucanase from *Trichoderma reesei*. It was also found that Pccel 12A variants, when displayed at the surface of yeast cells, were stabilized to a greater degree under acidic conditions, exhibited higher endoglucanase activities under acidic conditions, and also exhibited higher cellulase activities in cooperation with other cellulases such as β-glucosidase.

Finally, from the results of analysis on Variant 11, etc., it was confirmed that, inter alia, positions 107, 126 and 201 in SEQ ID NO:2 contribute to enhancements in endoglucanase activity. Of these, substitutions or arrangements to hydrophobic amino acid residues at positions 107 and 201, such as Q107P and V201A, appear to be major factors.

The entire contents of all patents and reference documents cited in this specification are incorporated herein by reference.

Sequence Listing

[Text in Sequence Listing]

SEQ ID NOS: 4 to 8: Variant proteins of endoglucanase from *Phanerochaete chrysosporiun*

SEQ ID NOS: 9 to 20: Synthesis Primers

[Sequence Listing]

What is claimed is:

1. An isolated protein selected from the group consisting of:
   (a) a protein having the amino acid sequence of SEQ ID NO:2;
   (b) a protein having the amino acid sequence of SEQ ID NO:2, except for a hydrophobic amino acid residue at positions 105, 171, 192 and 201, wherein the protein has endoglucanase activity; and
   (c) a protein having an amino acid sequence with at least 95% sequence identity to the amino acid sequence of SEQ ID NO:2, wherein the protein has endoglucanase activity.

2. The isolated protein of claim 1, wherein the endoglucanase activity is increased compared to endoglucanase activity from *Trichoderma reesei* at any pH from pH 2 to 4.

3. The isolated protein of claim 1, wherein the endoglucanase activity of the protein in (b) or (c) is increased compared to endoglucanase activity from *Trichoderma reesei* at any pH from pH 2 to 3.

4. The isolated protein of claim 2, wherein the endoglucanase from *Trichoderma reesei* has the amino acid sequence set forth in SEQ ID NO:7 or SEQ ID NO:8.

5. The isolated protein of claim 1, wherein the endoglucanase activity of the protein in (b) or (c) is equal to or increased compared to the activity of an endoglucanase having the amino acid sequence set forth in SEQ ID NO:2 at any pH from pH 2 to 4.

6. The isolated protein of claim 1, wherein the endoglucanase activity of the protein in (b) or (c) is equal to or increased compared to the activity of an endoglucanase having the amino acid of SEQ ID NO:2 at any pH from pH 2 to 3.

7. The isolated protein of claim 1, having hydrophobic amino acid residues in positions 105 or 201 of the amino acid sequence set forth in SEQ ID NO:2; and positions 192 and 201 of the amino acid sequence of SEQ ID NO:2.

8. The isolated protein of claim 1, wherein the amino acid sequence of the protein in (b) has at least one amino acid modification selected from the group consisting of K105E, Q107P, G126S, S152G, R171 M, S192L and V201A in the amino acid sequence of SEQ ID NO:2.

9. The isolated protein of claim 8, wherein the amino acid sequence of the protein in (b) has at least one amino acid modification selected from the group consisting of Q107P, S192L and V201A.

10. The isolated protein of claim 8, wherein the amino acid sequence of the protein in (b) has at least amino acid modifications Q 107P, G 126S and V201A.

11. The isolated protein of claim 8, wherein the amino acid sequence of the protein in (b) has at least amino acid modifications S152G, S 192L and V201A.

12. The isolated protein of claim 1, which is an endoglucanase obtained from *Phanerochaet*.

13. An isolated protein comprising the amino acid sequence of SEQ ID NO: 3, wherein said protein has endoclucanase activity.

* * * * *

UNITED STATES PATENT AND TRADEMARK OFFICE
CERTIFICATE OF CORRECTION

| | | |
|---|---|---|
| PATENT NO. | : 7,960,511 B2 | Page 1 of 1 |
| APPLICATION NO. | : 12/385505 | |
| DATED | : June 14, 2011 | |
| INVENTOR(S) | : Nobuhiko Muramoto et al. | |

It is certified that error appears in the above-identified patent and that said Letters Patent is hereby corrected as shown below:

On the Title page,

Please insert Item --[30] Foreign Application Priority Data, Apr. 10, 2008 (JP) 2008-102744--

Signed and Sealed this
Thirteenth Day of September, 2011

David J. Kappos
*Director of the United States Patent and Trademark Office*

```
SEQUENCE LISTING

<160> NUMBER OF SEQ ID NOS: 72

<210> SEQ ID NO 1
<211> LENGTH: 672
<212> TYPE: DNA
<213> ORGANISM: Phanerochaete chrysosporium
<220> FEATURE:
<221> NAME/KEY: CDS
<222> LOCATION: (1)..(672)

<400> SEQUENCE: 1 atc aca gga cag tac gac tgc att cct gcg gga gcg tac acg ctt tgt        48
Ile Thr Gly Gln Tyr Asp Cys Ile Pro Ala Gly Ala Tyr Thr Leu Cys
1               5                   10                  15 caa aac ctc tgg ggc gaa tac gct gga gtt ggc tcg cag aac tcg act        96
```

```
                -continued

Gln Asn Leu Trp Gly Glu Tyr Ala Gly Val Gly Ser Gln Asn Ser Thr
             20                  25                  30 ctg atc agt aca aat ggc aac gcg gtg act tgg cag acc aac tgg aca        144
Leu Ile Ser Thr Asn Gly Asn Ala Val Thr Trp Gln Thr Asn Trp Thr
             35                  40                  45 tgg gcc aac aat ccc aac acc gta aag agc tac gcg aac cta gag cac        192
Trp Ala Asn Asn Pro Asn Thr Val Lys Ser Tyr Ala Asn Leu Glu His
 50                  55                  60 aac acc gcg aag ggc atg cag ctc ggg acc atc acg agc gcg ccg acc        240
Asn Thr Ala Lys Gly Met Gln Leu Gly Thr Ile Thr Ser Ala Pro Thr
 65                  70                  75                  80 gcg tgg aac tgg acc tac gtt acc gaa tct cag ggc atc cgc gcc gac        288
Ala Trp Asn Trp Thr Tyr Val Thr Glu Ser Gln Gly Ile Arg Ala Asp
                 85                  90                  95 gtc tcc tat gac atc tgg ttc ggc aag gcc cag tcc ggc aac cca gcg        336
Val Ser Tyr Asp Ile Trp Phe Gly Lys Ala Gln Ser Gly Asn Pro Ala
                100                 105                 110 acg tct gcc tct tcc tat gag atc atg atc tgg ctg tcc ggc ctc ggc        384
Thr Ser Ala Ser Ser Tyr Glu Ile Met Ile Trp Leu Ser Gly Leu Gly
            115                 120                 125 ggt atc cag cct gtc ggc cac cag att ctc agc ggc ctc aac atc gct        432
Gly Ile Gln Pro Val Gly His Gln Ile Leu Ser Gly Leu Asn Ile Ala
        130                 135                 140 gga cac acc tgg aac ctc tgg agc ggc ccg aac tca aac tgg cag gtc        480
Gly His Thr Trp Asn Leu Trp Ser Gly Pro Asn Ser Asn Trp Gln Val
145                 150                 155                 160 ttc tcg ttc gtc atc tcc tcc ggc gaa gtg agg aac ttc agc gcg gac        528
Phe Ser Phe Val Ile Ser Ser Gly Glu Val Arg Asn Phe Ser Ala Asp
                165                 170                 175 ctt aac gag ttc ttc cag tat ctc atc cag agc cag ggc gtg gcc tcg        576
Leu Asn Glu Phe Phe Gln Tyr Leu Ile Gln Ser Gln Gly Val Ala Ser
            180                 185                 190 acc cag tac ctc caa gct att caa gtc ggc acc gaa cca ttc gtc ggc        624
Thr Gln Tyr Leu Gln Ala Ile Gln Val Gly Thr Glu Pro Phe Val Gly
        195                 200                 205 tct gca agc ctg ctg aca gag agt ttc gca gtc gca gtc aac gtt tga        672
Ser Ala Ser Leu Leu Thr Glu Ser Phe Ala Val Ala Val Asn Val
        210                 215                 220

<210> SEQ ID NO 2
<211> LENGTH: 223
<212> TYPE: PRT
<213> ORGANISM: Phanerochaete chrysosporium

<400> SEQUENCE: 2

Ile Thr Gly Gln Tyr Asp Cys Ile Pro Ala Gly Ala Tyr Thr Leu Cys
 1               5                  10                  15

Gln Asn Leu Trp Gly Glu Tyr Ala Gly Val Gly Ser Gln Asn Ser Thr
             20                  25                  30

Leu Ile Ser Thr Asn Gly Asn Ala Val Thr Trp Gln Thr Asn Trp Thr
             35                  40                  45

Trp Ala Asn Asn Pro Asn Thr Val Lys Ser Tyr Ala Asn Leu Glu His
 50                  55                  60

Asn Thr Ala Lys Gly Met Gln Leu Gly Thr Ile Thr Ser Ala Pro Thr
 65                  70                  75                  80

Ala Trp Asn Trp Thr Tyr Val Thr Glu Ser Gln Gly Ile Arg Ala Asp
                 85                  90                  95

Val Ser Tyr Asp Ile Trp Phe Gly Lys Ala Gln Ser Gly Asn Pro Ala
                100                 105                 110
```

```
Thr Ser Ala Ser Ser Tyr Glu Ile Met Ile Trp Leu Ser Gly Leu Gly
        115                 120                 125

Gly Ile Gln Pro Val Gly His Gln Ile Leu Ser Gly Leu Asn Ile Ala
    130                 135                 140

Gly His Thr Trp Asn Leu Trp Ser Gly Pro Asn Ser Asn Trp Gln Val
145                 150                 155                 160

Phe Ser Phe Val Ile Ser Ser Gly Glu Val Arg Asn Phe Ser Ala Asp
                165                 170                 175

Leu Asn Glu Phe Phe Gln Tyr Leu Ile Gln Ser Gln Gly Val Ala Ser
                180                 185                 190

Thr Gln Tyr Leu Gln Ala Ile Gln Val Gly Thr Glu Pro Phe Val Gly
        195                 200                 205

Ser Ala Ser Leu Leu Thr Glu Ser Phe Ala Val Ala Val Asn Val
        210                 215                 220
```

<210> SEQ ID NO 3
<211> LENGTH: 18
<212> TYPE: PRT
<213> ORGANISM: Phanerochaete chrysosporium

<400> SEQUENCE: 3

```
Tyr Ala Asn Leu Glu His Asn Thr Ala Lys Gly Met Gln Leu Gly Thr
1               5                   10                  15

Ile Thr
```

<210> SEQ ID NO 4
<211> LENGTH: 223
<212> TYPE: PRT
<213> ORGANISM: Artificial
<220> FEATURE:
<223> OTHER INFORMATION: Mutant protein based on endglucanase derived
      from Phanerochaete chrysosporium

<400> SEQUENCE: 4

```
Ile Thr Gly Gln Tyr Asp Cys Ile Pro Ala Gly Ala Tyr Thr Leu Cys
1               5                   10                  15

Gln Asn Leu Trp Gly Glu Tyr Ala Gly Val Gly Ser Gln Asn Ser Thr
            20                  25                  30

Leu Ile Ser Thr Asn Gly Asn Ala Val Thr Trp Gln Thr Asn Trp Thr
        35                  40                  45

Trp Ala Asn Asn Pro Asn Thr Val Lys Ser Tyr Ala Asn Leu Glu His
    50                  55                  60

Asn Thr Ala Lys Gly Met Gln Leu Gly Thr Ile Thr Ser Ala Pro Thr
65                  70                  75                  80

Ala Trp Asn Trp Thr Tyr Val Thr Glu Ser Gln Gly Ile Arg Ala Asp
                85                  90                  95

Val Ser Tyr Asp Ile Trp Phe Gly Lys Ala Pro Ser Gly Asn Pro Ala
            100                 105                 110

Thr Ser Ala Ser Ser Tyr Glu Ile Met Ile Trp Leu Ser Ser Leu Gly
        115                 120                 125

Gly Ile Gln Pro Val Gly His Gln Ile Leu Ser Gly Leu Asn Ile Ala
    130                 135                 140

Gly His Thr Trp Asn Leu Trp Ser Gly Pro Asn Ser Asn Trp Gln Val
145                 150                 155                 160

Phe Ser Phe Val Ile Ser Ser Gly Glu Val Arg Asn Phe Ser Ala Asp
                165                 170                 175

Leu Asn Glu Phe Phe Gln Tyr Leu Ile Gln Ser Gln Gly Val Ala Ser
                180                 185                 190
```

```
Thr Gln Tyr Leu Gln Ala Ile Gln Ala Gly Thr Glu Pro Phe Val Gly
        195                 200                 205

Ser Ala Ser Leu Leu Thr Glu Ser Phe Ala Val Ala Val Asn Val
    210                 215                 220

<210> SEQ ID NO 5
<211> LENGTH: 223
<212> TYPE: PRT
<213> ORGANISM: Artificial
<220> FEATURE:
<223> OTHER INFORMATION: Mutant Protein based on Endglucanase derived
      from Phanerochaete chrysosporium

<400> SEQUENCE: 5

Ile Thr Gly Gln Tyr Asp Cys Ile Pro Ala Gly Ala Tyr Thr Leu Cys
1               5                   10                  15

Gln Asn Leu Trp Gly Glu Tyr Ala Gly Val Gly Ser Gln Asn Ser Thr
            20                  25                  30

Leu Ile Ser Thr Asn Gly Asn Ala Val Thr Trp Gln Thr Asn Trp Thr
        35                  40                  45

Trp Ala Asn Asn Pro Asn Thr Val Lys Ser Tyr Ala Asn Leu Glu His
    50                  55                  60

Asn Thr Ala Lys Gly Met Gln Leu Gly Thr Ile Thr Ser Ala Pro Thr
65                  70                  75                  80

Ala Trp Asn Trp Thr Tyr Val Thr Glu Ser Gln Gly Ile Arg Ala Asp
                85                  90                  95

Val Ser Tyr Asp Ile Trp Phe Gly Lys Ala Pro Ser Gly Asn Pro Ala
                100                 105                 110

Thr Ser Ala Ser Ser Tyr Glu Ile Met Ile Trp Leu Ser Ser Leu Gly
        115                 120                 125

Gly Ile Gln Pro Val Gly His Gln Ile Leu Ser Gly Leu Asn Ile Ala
    130                 135                 140

Gly His Thr Trp Asn Leu Trp Gly Gly Pro Asn Ser Asn Trp Gln Val
145                 150                 155                 160

Phe Ser Phe Val Ile Ser Ser Gly Glu Val Arg Asn Phe Ser Ala Asp
                165                 170                 175

Leu Asn Glu Phe Phe Gln Tyr Leu Ile Gln Ser Gln Gly Val Ala Leu
            180                 185                 190

Thr Gln Tyr Leu Gln Ala Ile Gln Ala Gly Thr Glu Pro Phe Val Gly
        195                 200                 205

Ser Ala Ser Leu Leu Thr Glu Ser Phe Ala Val Ala Val Asn Val
    210                 215                 220

<210> SEQ ID NO 6
<211> LENGTH: 223
<212> TYPE: PRT
<213> ORGANISM: Artificial
<220> FEATURE:
<223> OTHER INFORMATION: Mutant Protein based on Endglucanase derived
      from Phanerochaete chrysosporium

<400> SEQUENCE: 6

Ile Thr Gly Gln Tyr Asp Cys Ile Pro Ala Gly Ala Tyr Thr Leu Cys
1               5                   10                  15

Gln Asn Leu Trp Gly Glu Tyr Ala Gly Val Gly Ser Gln Asn Ser Thr
            20                  25                  30

Leu Ile Ser Thr Asn Gly Asn Ala Val Thr Trp Gln Thr Asn Trp Thr
        35                  40                  45
```

```
Trp Ala Asn Asn Pro Asn Thr Val Lys Ser Tyr Ala Asn Leu Glu His
    50                  55                  60

Asn Thr Ala Lys Gly Met Gln Leu Gly Thr Ile Thr Ser Ala Pro Thr
65                  70                  75                  80

Ala Trp Asn Trp Thr Tyr Val Thr Glu Ser Gln Gly Ile Arg Ala Asp
                85                  90                  95

Val Ser Tyr Asp Ile Trp Phe Gly Lys Ala Gln Ser Gly Asn Pro Ala
                100                 105                 110

Thr Ser Ala Ser Ser Tyr Glu Ile Met Ile Trp Leu Ser Gly Leu Gly
            115                 120                 125

Gly Ile Gln Pro Val Gly His Gln Ile Leu Ser Gly Leu Asn Ile Ala
        130                 135                 140

Gly His Thr Trp Asn Leu Trp Ser Gly Pro Asn Ser Asn Trp Gln Val
145                 150                 155                 160

Phe Ser Phe Val Ile Ser Ser Gly Glu Val Arg Asn Phe Ser Ala Asp
                165                 170                 175

Leu Asn Glu Phe Phe Gln Tyr Leu Ile Gln Ser Gln Gly Val Ala Leu
            180                 185                 190

Thr Gln Tyr Leu Gln Ala Ile Gln Val Gly Thr Glu Pro Phe Val Gly
        195                 200                 205

Ser Ala Ser Leu Leu Thr Glu Ser Phe Ala Val Ala Val Asn Val
    210                 215                 220

<210> SEQ ID NO 7
<211> LENGTH: 223
<212> TYPE: PRT
<213> ORGANISM: Artificial
<220> FEATURE:
<223> OTHER INFORMATION: Mutant Protein based on Endglucanase derived
      from Phanerochaete chrysosporium

<400> SEQUENCE: 7

Ile Thr Gly Gln Tyr Asp Cys Ile Pro Ala Gly Ala Tyr Thr Leu Cys
1               5                   10                  15

Gln Asn Leu Trp Gly Glu Tyr Ala Gly Val Gly Ser Gln Asn Ser Thr
            20                  25                  30

Leu Ile Ser Thr Asn Gly Asn Ala Val Thr Trp Gln Thr Asn Trp Thr
        35                  40                  45

Trp Ala Asn Asn Pro Asn Thr Val Lys Ser Tyr Ala Asn Leu Glu His
    50                  55                  60

Asn Thr Ala Lys Gly Met Gln Leu Gly Thr Ile Thr Ser Ala Pro Thr
65                  70                  75                  80

Ala Trp Asn Trp Thr Tyr Val Thr Glu Ser Gln Gly Ile Arg Ala Asp
                85                  90                  95

Val Ser Tyr Asp Ile Trp Phe Gly Glu Ala Gln Ser Gly Asn Pro Ala
                100                 105                 110

Thr Ser Ala Ser Ser Tyr Glu Ile Met Ile Trp Leu Ser Gly Leu Gly
            115                 120                 125

Gly Ile Gln Pro Val Gly His Gln Ile Leu Ser Gly Leu Asn Ile Ala
        130                 135                 140

Gly His Thr Trp Asn Leu Trp Ser Gly Pro Asn Ser Asn Trp Gln Val
145                 150                 155                 160

Phe Ser Phe Val Ile Ser Ser Gly Glu Val Arg Asn Phe Ser Ala Asp
                165                 170                 175

Leu Asn Glu Phe Phe Gln Tyr Leu Ile Gln Ser Gln Gly Val Ala Ser
            180                 185                 190
```

```
Thr Gln Tyr Leu Gln Ala Ile Gln Val Gly Thr Glu Pro Phe Val Gly
        195                 200                 205

Ser Ala Ser Leu Leu Thr Glu Ser Phe Ala Val Ala Val Asn Val
    210                 215                 220

<210> SEQ ID NO 8
<211> LENGTH: 223
<212> TYPE: PRT
<213> ORGANISM: Artificial
<220> FEATURE:
<223> OTHER INFORMATION: Mutant Protein based on Endglucanase derived
      from Phanerochaete chrysosporium

<400> SEQUENCE: 8

Ile Thr Gly Gln Tyr Asp Cys Ile Pro Ala Gly Ala Tyr Thr Leu Cys
1               5                   10                  15

Gln Asn Leu Trp Gly Glu Tyr Ala Val Gly Ser Gln Asn Ser Thr
            20                  25                  30

Leu Ile Ser Thr Asn Gly Asn Ala Val Thr Trp Gln Thr Asn Trp Thr
            35                  40                  45

Trp Ala Asn Asn Pro Asn Thr Val Lys Ser Tyr Ala Asn Leu Glu His
50                  55                  60

Asn Thr Ala Lys Gly Met Gln Leu Gly Thr Ile Thr Ser Ala Pro Thr
65                  70                  75                  80

Ala Trp Asn Trp Thr Tyr Val Thr Glu Ser Gln Gly Ile Arg Ala Asp
                85                  90                  95

Val Ser Tyr Asp Ile Trp Phe Gly Lys Ala Gln Ser Gly Asn Pro Ala
                100                 105                 110

Thr Ser Ala Ser Ser Tyr Glu Ile Met Ile Trp Leu Ser Gly Leu Gly
            115                 120                 125

Gly Ile Gln Pro Val Gly His Gln Ile Leu Ser Gly Leu Asn Ile Ala
    130                 135                 140

Gly His Thr Trp Asn Leu Trp Ser Gly Pro Asn Ser Asn Trp Gln Val
145                 150                 155                 160

Phe Ser Phe Val Ile Ser Ser Gly Glu Val Met Asn Phe Ser Ala Asp
                165                 170                 175

Leu Asn Glu Phe Phe Gln Tyr Leu Ile Gln Ser Gln Gly Val Ala Ser
            180                 185                 190

Thr Gln Tyr Leu Gln Ala Ile Gln Val Gly Thr Glu Pro Phe Val Gly
        195                 200                 205

Ser Ala Ser Leu Leu Thr Glu Ser Phe Ala Val Ala Val Asn Val
    210                 215                 220

<210> SEQ ID NO 9
<211> LENGTH: 37
<212> TYPE: DNA
<213> ORGANISM: Artificial
<220> FEATURE:
<223> OTHER INFORMATION: primer

<400> SEQUENCE: 9
ccgcggagat cacaggacag tacgactgca ttcctgc                     37

<210> SEQ ID NO 10
<211> LENGTH: 37
<212> TYPE: DNA
<213> ORGANISM: Artificial
<220> FEATURE:
<223> OTHER INFORMATION: primer

<400> SEQUENCE: 10
```

```
ctcgagccaa cgttgactgc gactgcgaaa ctctctg                                37
```

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11

```
gagctacgcg aacctagagc acaacaccgc                                        30
```

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12

```
gcggtgttgt gctctaggtt cgcgtagctc                                        30
```

<210> SEQ ID NO 13
<211> LENGTH: 29
<212> TYPE: DNA
<213> ORGANISM: Artificial
<220> FEATURE:
<223> OTHER INFORMATION: primer

<400> SEQUENCE: 13

```
aaacatatgg cacagactat cacaggaca                                         29
```

<210> SEQ ID NO 14
<211> LENGTH: 32
<212> TYPE: DNA
<213> ORGANISM: Artificial
<220> FEATURE:
<223> OTHER INFORMATION: primer

<400> SEQUENCE: 14

```
aaactcgagt caaacgttga ctgcgactgc ga                                     32
```

<210> SEQ ID NO 15
<211> LENGTH: 31
<212> TYPE: DNA
<213> ORGANISM: Artificial
<220> FEATURE:
<223> OTHER INFORMATION: primer

<400> SEQUENCE: 15

```
aaacatatgc agcagactgt ctggggccag t                                      31
```

<210> SEQ ID NO 16
<211> LENGTH: 33
<212> TYPE: DNA
<213> ORGANISM: Artificial
<220> FEATURE:
<223> OTHER INFORMATION: primer

<400> SEQUENCE: 16

```
aaactcgagc tactttcttg cgagacacga gct                                    33
```

<210> SEQ ID NO 17
<211> LENGTH: 29
<212> TYPE: DNA
<213> ORGANISM: Artificial

```
<220> FEATURE:
<223> OTHER INFORMATION: primer

<400> SEQUENCE: 17
aaacatatgc aaaccagctg tgaccagtg                                          29

<210> SEQ ID NO 18
<211> LENGTH: 33
<212> TYPE: DNA
<213> ORGANISM: Artificial
<220> FEATURE:
<223> OTHER INFORMATION: primer

<400> SEQUENCE: 18
aaactcgagt tagttgatag atgcggtcca gga                                     33

<210> SEQ ID NO 19
<211> LENGTH: 26
<212> TYPE: DNA
<213> ORGANISM: Artificial
<220> FEATURE:
<223> OTHER INFORMATION: primer

<400> SEQUENCE: 19
atctcgatcc cgcgaaatta atacga                                             26

<210> SEQ ID NO 20
<211> LENGTH: 24
<212> TYPE: DNA
<213> ORGANISM: Artificial
<220> FEATURE:
<223> OTHER INFORMATION: primer

<400> SEQUENCE: 20
tccggatata gttcctcctt tcag                                               24

<210> SEQ ID NO 21
<211> LENGTH: 16
<212> TYPE: DNA
<213> ORGANISM: Bacteriophage T7

<400> SEQUENCE: 21
aatacgactc actata                                                        16

<210> SEQ ID NO 22
<211> LENGTH: 48
<212> TYPE: DNA
<213> ORGANISM: Bacteriophage T7

<400> SEQUENCE: 22
ctagcataac cccttggggc ctctaaacgg gtcttgaggg gttttttg                     48

<210> SEQ ID NO 23
<211> LENGTH: 922
<212> TYPE: DNA
<213> ORGANISM: Artificial
<220> FEATURE:
<223> OTHER INFORMATION: template DNA
<220> FEATURE:
<221> NAME/KEY: CDS
<222> LOCATION: (99)..(782)

<400> SEQUENCE: 23
atctcgatcc cgcgaaatta atacgactca ctatagggag accacaacgg tttccctcta        60
gaaataattt tgtttaactt taagaaggag atatacat atg gca cag act atc aca       116
                                          Met Ala Gln Thr Ile Thr
```

```
gga cag tac gac tgc att cct gcg gga gcg tac acg ctt tgt caa aac      164
Gly Gln Tyr Asp Cys Ile Pro Ala Gly Ala Tyr Thr Leu Cys Gln Asn
             10                  15                  20 ctc tgg ggc gaa tac gct gga gtt ggc tcg cag aac tcg act ctg atc      212
Leu Trp Gly Glu Tyr Ala Gly Val Gly Ser Gln Asn Ser Thr Leu Ile
         25                  30                  35 agt aca aat ggc aac gcc gtg act tgg cag acc aac tgg aca tgg gcc      260
Ser Thr Asn Gly Asn Ala Val Thr Trp Gln Thr Asn Trp Thr Trp Ala
     40                  45                  50 aac aat ccc aac acc gta aag agc tac gcg aac cta gag cac aac acc      308
Asn Asn Pro Asn Thr Val Lys Ser Tyr Ala Asn Leu Glu His Asn Thr
 55                  60                  65                  70 gcg aag ggc atg cag ctc ggg acc atc acg agc gcg ccg acc gcg tgg      356
Ala Lys Gly Met Gln Leu Gly Thr Ile Thr Ser Ala Pro Thr Ala Trp
                 75                  80                  85 aac tgg acc tac gtt acc gaa tct cag ggc atc cgc gcc gac gtc tcc      404
Asn Trp Thr Tyr Val Thr Glu Ser Gln Gly Ile Arg Ala Asp Val Ser
             90                  95                 100 tat gac atc tgg ttc ggc aag gcc cag tcc ggc aac cca gcg acg tct      452
Tyr Asp Ile Trp Phe Gly Lys Ala Gln Ser Gly Asn Pro Ala Thr Ser
         105                 110                 115 gcc tct tcc tat gag atc atg atc tgg ctg tcc ggc ctc ggt ggt atc      500
Ala Ser Ser Tyr Glu Ile Met Ile Trp Leu Ser Gly Leu Gly Gly Ile
     120                 125                 130 cag cct gtc ggc cac cag att ctc agc ggc ctc aac atc gct gga cac      548
Gln Pro Val Gly His Gln Ile Leu Ser Gly Leu Asn Ile Ala Gly His
135                 140                 145                 150 acc tgg aac ctc tgg agc ggc ccg aac tca aac tgg cag gtc ttc tcg      596
Thr Trp Asn Leu Trp Ser Gly Pro Asn Ser Asn Trp Gln Val Phe Ser
                 155                 160                 165 ttc gtc atc tcc tcc ggc gaa gtg agg aac ttc agc gcg gac ctt aac      644
Phe Val Ile Ser Ser Gly Glu Val Arg Asn Phe Ser Ala Asp Leu Asn
             170                 175                 180 gag ttc ttc cag tat ctc atc cag agc cag ggc gtg gcc tcg acc cag      692
Glu Phe Phe Gln Tyr Leu Ile Gln Ser Gln Gly Val Ala Ser Thr Gln
         185                 190                 195 tac ctc caa gct att caa gtc ggc acc gaa cca ttc gtc ggc tct gca      740
Tyr Leu Gln Ala Ile Gln Val Gly Thr Glu Pro Phe Val Gly Ser Ala
     200                 205                 210 agc ctg ctg aca gag agt ttc gca gtc gca gtc aac gtt tga              782
Ser Leu Leu Thr Glu Ser Phe Ala Val Ala Val Asn Val
215                 220                 225 ctcgagatcc ggctgctaac aaagcccgaa aggaagctga gttggctgct gccaccgctg      842
agcaataact agcataaccc cttggggcct ctaaacgggt cttgaggggt ttttgctga       902 aaggaggaac tatatccgga                                                  922

<210> SEQ ID NO 24
<211> LENGTH: 227
<212> TYPE: PRT
<213> ORGANISM: Artificial
<220> FEATURE:
<223> OTHER INFORMATION: Synthetic Construct

<400> SEQUENCE: 24

Met Ala Gln Thr Ile Thr Gly Gln Tyr Asp Cys Ile Pro Ala Gly Ala
1               5                   10                  15

Tyr Thr Leu Cys Gln Asn Leu Trp Gly Glu Tyr Ala Gly Val Gly Ser
            20                  25                  30
```

-continued

```
Gln Asn Ser Thr Leu Ile Ser Thr Asn Gly Asn Ala Val Thr Trp Gln
     35                  40                  45
Thr Asn Trp Thr Trp Ala Asn Asn Pro Asn Thr Val Lys Ser Tyr Ala
 50                  55                  60
Asn Leu Glu His Asn Thr Ala Lys Gly Met Gln Leu Gly Thr Ile Thr
 65                  70                  75                  80
Ser Ala Pro Thr Ala Trp Asn Trp Thr Tyr Val Thr Glu Ser Gln Gly
                 85                  90                  95
Ile Arg Ala Asp Val Ser Tyr Asp Ile Trp Phe Gly Lys Ala Gln Ser
            100                 105                 110
Gly Asn Pro Ala Thr Ser Ala Ser Ser Tyr Glu Ile Met Ile Trp Leu
        115                 120                 125
Ser Gly Leu Gly Gly Ile Gln Pro Val Gly His Gln Ile Leu Ser Gly
    130                 135                 140
Leu Asn Ile Ala Gly His Thr Trp Asn Leu Trp Ser Gly Pro Asn Ser
145                 150                 155                 160
Asn Trp Gln Val Phe Ser Phe Val Ile Ser Ser Gly Glu Val Arg Asn
                165                 170                 175
Phe Ser Ala Asp Leu Asn Glu Phe Phe Gln Tyr Leu Ile Gln Ser Gln
            180                 185                 190
Gly Val Ala Ser Thr Gln Tyr Leu Gln Ala Ile Gln Val Gly Thr Glu
        195                 200                 205
Pro Phe Val Gly Ser Ala Ser Leu Leu Thr Glu Ser Phe Ala Val Ala
    210                 215                 220
Val Asn Val
225

<210> SEQ ID NO 25
<211> LENGTH: 1435
<212> TYPE: DNA
<213> ORGANISM: Artificial
<220> FEATURE:
<223> OTHER INFORMATION: template DNA
<220> FEATURE:
<221> NAME/KEY: CDS
<222> LOCATION: (99)..(1295)

<400> SEQUENCE: 25
atctcgatcc cgcgaaatta atacgactca ctatagggag accacaacgg tttccctcta      60
gaaataattt tgtttaactt taagaaggag atatacat atg cag cag act gtc tgg     116
                                          Met Gln Gln Thr Val Trp
                                            1               5 ggc cag tgt gga ggt att ggt tgg agc gga cct acg aat tgt gct cct       164
Gly Gln Cys Gly Gly Ile Gly Trp Ser Gly Pro Thr Asn Cys Ala Pro
            10                  15                  20 ggc tca gct tgt tcg acc ctc aat cct tat tat gcg caa tgt att ccg       212
Gly Ser Ala Cys Ser Thr Leu Asn Pro Tyr Tyr Ala Gln Cys Ile Pro
         25                  30                  35 gga gcc act act atc acc act tcg acc cgg cca cca tcc ggt cca acc       260
Gly Ala Thr Thr Ile Thr Thr Ser Thr Arg Pro Pro Ser Gly Pro Thr
     40                  45                  50 acc acc acc agg gct acc tca aca agc tca tca act cca ccc acg agc       308
Thr Thr Thr Arg Ala Thr Ser Thr Ser Ser Ser Thr Pro Pro Thr Ser
 55                  60                  65                  70 tct ggg gtc cga ttt gcc ggc gtt aac atc gcg ggt ttt gac ttt ggc       356
Ser Gly Val Arg Phe Ala Gly Val Asn Ile Ala Gly Phe Asp Phe Gly
                 75                  80                  85 tgt acc aca gat ggc act tgc gtt acc tcg aag gtt tat cct ccg ttg       404
Cys Thr Thr Asp Gly Thr Cys Val Thr Ser Lys Val Tyr Pro Pro Leu
```

```
                    90              95              100
aag aac ttc acc ggc tca aac aac tac ccc gat ggc atc ggc cag atg        452
Lys Asn Phe Thr Gly Ser Asn Asn Tyr Pro Asp Gly Ile Gly Gln Met
            105                 110                 115 cag cac ttc gtc aac gac gac ggg atg act att ttc cgc tta cct gtc        500
Gln His Phe Val Asn Asp Asp Gly Met Thr Ile Phe Arg Leu Pro Val
    120                 125                 130 gga tgg cag tac ctc gtc aac aac aat ttg ggc ggc aat ctt gat tcc        548
Gly Trp Gln Tyr Leu Val Asn Asn Asn Leu Gly Gly Asn Leu Asp Ser
135                 140                 145                 150 acg agc att tcc aag tat gat cag ctt gtt cag ggg tgc ctg tct ctg        596
Thr Ser Ile Ser Lys Tyr Asp Gln Leu Val Gln Gly Cys Leu Ser Leu
                155                 160                 165 ggc gca tac tgc atc gtc gac atc cac aat tat gct cga tgg aac ggt        644
Gly Ala Tyr Cys Ile Val Asp Ile His Asn Tyr Ala Arg Trp Asn Gly
            170                 175                 180 ggg atc att ggt cag ggc ggc cct act aat gct caa ttc acg agc ctt        692
Gly Ile Ile Gly Gln Gly Gly Pro Thr Asn Ala Gln Phe Thr Ser Leu
    185                 190                 195 tgg tcg cag ttg gca tca aag tac gca tct cag tcg agg gtg tgg ttc        740
Trp Ser Gln Leu Ala Ser Lys Tyr Ala Ser Gln Ser Arg Val Trp Phe
200                 205                 210 ggc atc atg aat gag ccc cac gac gtg aac atc aac acc tgg gct gcc        788
Gly Ile Met Asn Glu Pro His Asp Val Asn Ile Asn Thr Trp Ala Ala
215                 220                 225                 230 acg gtc caa gag gtt gta acc gca atc cgc aac gct ggt gct acg tcg        836
Thr Val Gln Glu Val Val Thr Ala Ile Arg Asn Ala Gly Ala Thr Ser
                235                 240                 245 caa ttc atc tct ttg cct gga aat gat tgg caa tct gct ggg gct ttc        884
Gln Phe Ile Ser Leu Pro Gly Asn Asp Trp Gln Ser Ala Gly Ala Phe
            250                 255                 260 ata tcc gat ggc agt gca gcc gcc ctg tct caa gtc acg aac ccg gat        932
Ile Ser Asp Gly Ser Ala Ala Ala Leu Ser Gln Val Thr Asn Pro Asp
    265                 270                 275 ggg tca aca acg aat ctg att ttt gac gtg cac aaa tac ttg gac tta        980
Gly Ser Thr Thr Asn Leu Ile Phe Asp Val His Lys Tyr Leu Asp Leu
280                 285                 290 gac aac tcc ggt act cac gcc gaa tgt act aca aat aac att gac ggc       1028
Asp Asn Ser Gly Thr His Ala Glu Cys Thr Thr Asn Asn Ile Asp Gly
295                 300                 305                 310 gcc ttt tct ccg ctt gcc act tgg ctc cga cag aac aat cgc cag gct       1076
Ala Phe Ser Pro Leu Ala Thr Trp Leu Arg Gln Asn Asn Arg Gln Ala
                315                 320                 325 atc ctg aca gaa acc ggt ggt ggc aac gtt cag tcc tgc ata caa gac       1124
Ile Leu Thr Glu Thr Gly Gly Gly Asn Val Gln Ser Cys Ile Gln Asp
            330                 335                 340 atg tgc cag caa atc caa tat ctc aac cag aac tca gat gtc tat ctt       1172
Met Cys Gln Gln Ile Gln Tyr Leu Asn Gln Asn Ser Asp Val Tyr Leu
    345                 350                 355 ggc tat gtt ggt tgg ggt gcc gga tca ttt gat agc acg tat gtc ctg       1220
Gly Tyr Val Gly Trp Gly Ala Gly Ser Phe Asp Ser Thr Tyr Val Leu
360                 365                 370 acg gaa aca ccg act ggc agt ggt aac tca tgg acg gac aca tcc ttg       1268
Thr Glu Thr Pro Thr Gly Ser Gly Asn Ser Trp Thr Asp Thr Ser Leu
375                 380                 385                 390 gtc agc tcg tgt ctc gca aga aag tag ctcgagatcc ggctgctaac             1315
Val Ser Ser Cys Leu Ala Arg Lys
                395 aaagcccgaa aggaagctga gttggctgct gccaccgctg agcaataact agcataaccc    1375
```
cttggggcct ctaaacgggt cttgagggt tttttgctga aggaggaac tatatccgga   1435

<210> SEQ ID NO 26
<211> LENGTH: 398
<212> TYPE: PRT
<213> ORGANISM: Artificial
<220> FEATURE:
<223> OTHER INFORMATION: Synthetic Construct

<400> SEQUENCE: 26

```
Met Gln Gln Thr Val Trp Gly Gln Cys Gly Gly Ile Gly Trp Ser Gly
1               5                   10                  15
Pro Thr Asn Cys Ala Pro Gly Ser Ala Cys Ser Thr Leu Asn Pro Tyr
            20                  25                  30
Tyr Ala Gln Cys Ile Pro Gly Ala Thr Thr Ile Thr Thr Ser Thr Arg
        35                  40                  45
Pro Pro Ser Gly Pro Thr Thr Thr Arg Ala Thr Ser Thr Ser Ser
    50                  55                  60
Ser Thr Pro Pro Thr Ser Ser Gly Val Arg Phe Ala Gly Val Asn Ile
65                  70                  75                  80
Ala Gly Phe Asp Phe Gly Cys Thr Thr Asp Gly Thr Cys Val Thr Ser
                85                  90                  95
Lys Val Tyr Pro Pro Leu Lys Asn Phe Thr Gly Ser Asn Asn Tyr Pro
            100                 105                 110
Asp Gly Ile Gly Gln Met Gln His Phe Val Asn Asp Gly Met Thr
        115                 120                 125
Ile Phe Arg Leu Pro Val Gly Trp Gln Tyr Leu Val Asn Asn Asn Leu
    130                 135                 140
Gly Gly Asn Leu Asp Ser Thr Ser Ile Ser Lys Tyr Asp Gln Leu Val
145                 150                 155                 160
Gln Gly Cys Leu Ser Leu Gly Ala Tyr Cys Ile Val Asp Ile His Asn
                165                 170                 175
Tyr Ala Arg Trp Asn Gly Gly Ile Ile Gly Gln Gly Gly Pro Thr Asn
            180                 185                 190
Ala Gln Phe Thr Ser Leu Trp Ser Gln Leu Ala Ser Lys Tyr Ala Ser
        195                 200                 205
Gln Ser Arg Val Trp Phe Gly Ile Met Asn Glu Pro His Asp Val Asn
    210                 215                 220
Ile Asn Thr Trp Ala Ala Thr Val Gln Glu Val Val Thr Ala Ile Arg
225                 230                 235                 240
Asn Ala Gly Ala Thr Ser Gln Phe Ile Ser Leu Pro Gly Asn Asp Trp
                245                 250                 255
Gln Ser Ala Gly Ala Phe Ile Ser Asp Gly Ser Ala Ala Ala Leu Ser
            260                 265                 270
Gln Val Thr Asn Pro Asp Gly Ser Thr Thr Asn Leu Ile Phe Asp Val
        275                 280                 285
His Lys Tyr Leu Asp Leu Asp Asn Ser Gly Thr His Ala Glu Cys Thr
    290                 295                 300
Thr Asn Asn Ile Asp Gly Ala Phe Ser Pro Leu Ala Thr Trp Leu Arg
305                 310                 315                 320
Gln Asn Asn Arg Gln Ala Ile Leu Thr Glu Thr Gly Gly Gly Asn Val
                325                 330                 335
Gln Ser Cys Ile Gln Asp Met Cys Gln Gln Ile Gln Tyr Leu Asn Gln
            340                 345                 350
Asn Ser Asp Val Tyr Leu Gly Tyr Val Gly Trp Gly Ala Gly Ser Phe
        355                 360                 365
```

```
Asp Ser Thr Tyr Val Leu Thr Glu Thr Pro Thr Gly Ser Gly Asn Ser
    370                 375                 380

Trp Thr Asp Thr Ser Leu Val Ser Ser Cys Leu Ala Arg Lys
385                 390                 395

<210> SEQ ID NO 27
<211> LENGTH: 898
<212> TYPE: DNA
<213> ORGANISM: Artificial
<220> FEATURE:
<223> OTHER INFORMATION: template DNA
<220> FEATURE:
<221> NAME/KEY: CDS
<222> LOCATION: (99)..(758)

<400> SEQUENCE: 27
atctcgatcc cgcgaaatta atacgactca ctataggag accacaacgg tttccctcta        60
gaaataattt tgtttaactt taagaaggag atatacat atg caa acc agc tgt gac      116
                                         Met Gln Thr Ser Cys Asp
                                           1               5 cag tgg gca acc ttc act ggc aac ggc tac aca gtc agc aac aac ctt        164
Gln Trp Ala Thr Phe Thr Gly Asn Gly Tyr Thr Val Ser Asn Asn Leu
             10                  15                  20 tgg gga gca tca gcc ggc tct gga ttt ggc tgc gtg acg gcg gta tcg        212
Trp Gly Ala Ser Ala Gly Ser Gly Phe Gly Cys Val Thr Ala Val Ser
         25                  30                  35 ctc agc ggc ggg gcc tcc tgg cac gca gac tgg cag tgg tcc ggc ggc        260
Leu Ser Gly Gly Ala Ser Trp His Ala Asp Trp Gln Trp Ser Gly Gly
     40                  45                  50 cag aac aac gtc aag tcg tac cag aac tct cag att gcc att ccc cag        308
Gln Asn Asn Val Lys Ser Tyr Gln Asn Ser Gln Ile Ala Ile Pro Gln
 55                  60                  65                  70 aag agg acc gtc aac agc atc agc agc atg ccc acc act gcc agc tgg        356
Lys Arg Thr Val Asn Ser Ile Ser Ser Met Pro Thr Thr Ala Ser Trp
                 75                  80                  85 agc tac agc ggg agc aac atc cgc gct aat gtt gcg tat gac ttg ttc        404
Ser Tyr Ser Gly Ser Asn Ile Arg Ala Asn Val Ala Tyr Asp Leu Phe
             90                  95                 100 acc gca gcc aac ccg aat cat gtc acg tac tcg gga gac tac gaa ctc        452
Thr Ala Ala Asn Pro Asn His Val Thr Tyr Ser Gly Asp Tyr Glu Leu
        105                 110                 115 atg atc tgg ctt ggc aaa tac ggc gat att ggg ccg att ggg tcc tca        500
Met Ile Trp Leu Gly Lys Tyr Gly Asp Ile Gly Pro Ile Gly Ser Ser
    120                 125                 130 cag gga aca gtc aac gtc ggt ggc cag agc tgg acg ctc tac tat ggc        548
Gln Gly Thr Val Asn Val Gly Gly Gln Ser Trp Thr Leu Tyr Tyr Gly
135                 140                 145                 150 tac aac gga gcc atg caa gtc tat tcc ttt gtg gcc cag acc aac act        596
Tyr Asn Gly Ala Met Gln Val Tyr Ser Phe Val Ala Gln Thr Asn Thr
                155                 160                 165 acc aac tac agc gga gat gtc aag aac ttc ttc aat tat ctc cga gac        644
Thr Asn Tyr Ser Gly Asp Val Lys Asn Phe Phe Asn Tyr Leu Arg Asp
            170                 175                 180 aat aaa gga tac aac gct gca ggc caa tat gtt ctt agc tac caa ttt        692
Asn Lys Gly Tyr Asn Ala Ala Gly Gln Tyr Val Leu Ser Tyr Gln Phe
        185                 190                 195 ggt acc gag ccc ttc acg ggc agt gga act ctg aac gtc gca tcc tgg        740
Gly Thr Glu Pro Phe Thr Gly Ser Gly Thr Leu Asn Val Ala Ser Trp
    200                 205                 210 acc gca tct atc aac taa ctcgagatcc ggctgctaac aaagcccgaa                788
Thr Ala Ser Ile Asn
```

-continued

```
215 aggaagctga gttggctgct gccaccgctg agcaataact agcataaccc cttggggcct      848 ctaaacgggt cttgagggt tttttgctga aggaggaac tatatccgga                  898
```

```
<210> SEQ ID NO 28
<211> LENGTH: 219
<212> TYPE: PRT
<213> ORGANISM: Artificial
<220> FEATURE:
<223> OTHER INFORMATION: Synthetic Construct

<400> SEQUENCE: 28
```

```
Met Gln Thr Ser Cys Asp Gln Trp Ala Thr Phe Thr Gly Asn Gly Tyr
1               5                   10                  15

Thr Val Ser Asn Asn Leu Trp Gly Ala Ser Ala Gly Ser Gly Phe Gly
            20                  25                  30

Cys Val Thr Ala Val Ser Leu Ser Gly Gly Ala Ser Trp His Ala Asp
        35                  40                  45

Trp Gln Trp Ser Gly Gly Gln Asn Asn Val Lys Ser Tyr Gln Asn Ser
    50                  55                  60

Gln Ile Ala Ile Pro Gln Lys Arg Thr Val Asn Ser Ile Ser Ser Met
65                  70                  75                  80

Pro Thr Thr Ala Ser Trp Ser Tyr Ser Gly Ser Asn Ile Arg Ala Asn
                85                  90                  95

Val Ala Tyr Asp Leu Phe Thr Ala Ala Asn Pro Asn His Val Thr Tyr
            100                 105                 110

Ser Gly Asp Tyr Glu Leu Met Ile Trp Leu Gly Lys Tyr Gly Asp Ile
        115                 120                 125

Gly Pro Ile Gly Ser Ser Gln Gly Thr Val Asn Val Gly Gly Gln Ser
    130                 135                 140

Trp Thr Leu Tyr Tyr Gly Tyr Asn Gly Ala Met Gln Val Tyr Ser Phe
145                 150                 155                 160

Val Ala Gln Thr Asn Thr Thr Asn Tyr Ser Gly Asp Val Lys Asn Phe
                165                 170                 175

Phe Asn Tyr Leu Arg Asp Asn Lys Gly Tyr Asn Ala Ala Gly Gln Tyr
            180                 185                 190

Val Leu Ser Tyr Gln Phe Gly Thr Glu Pro Phe Thr Gly Ser Gly Thr
        195                 200                 205

Leu Asn Val Ala Ser Trp Thr Ala Ser Ile Asn
    210                 215
```

```
<210> SEQ ID NO 29
<211> LENGTH: 898
<212> TYPE: DNA
<213> ORGANISM: Artificial
<220> FEATURE:
<223> OTHER INFORMATION: template DNA
<220> FEATURE:
<221> NAME/KEY: CDS
<222> LOCATION: (99)..(758)

<400> SEQUENCE: 29
```

```
atctcgatcc cgcgaaatta atacgactca ctataggag accacaacgg tttccctcta      60
gaaataattt tgtttaactt taagaaggag atatacat atg gca cag act atc aca    116
                                            Met Ala Gln Thr Ile Thr
                                            1               5 cag tgg gca acc ttc act ggc aac ggc tac aca gtc agc aac aac ctt      164
Gln Trp Ala Thr Phe Thr Gly Asn Gly Tyr Thr Val Ser Asn Asn Leu
        10                  15                  20
```

-continued

| | | |
|---|---|---|
| tgg gga gca tca gcc ggc tct gga ttt ggc tgc gtg acg gcg gta tcg<br>Trp Gly Ala Ser Ala Gly Ser Gly Phe Gly Cys Val Thr Ala Val Ser<br>              25                        30                           35 | | 212 |
| ctc agc ggc ggg gcc tcc tgg cac gca gac tgg cag tgg tcc ggc ggc<br>Leu Ser Gly Gly Ala Ser Trp His Ala Asp Trp Gln Trp Ser Gly Gly<br>  40                              45                        50 | | 260 |
| cag aac aac gtc aag tcg tac cag aac tct cag att gcc att ccc cag<br>Gln Asn Asn Val Lys Ser Tyr Gln Asn Ser Gln Ile Ala Ile Pro Gln<br>55                         60                            65                        70 | | 308 |
| aag agg acc gtc aac agc atc agc agc atg ccc acc act gcc agc tgg<br>Lys Arg Thr Val Asn Ser Ile Ser Ser Met Pro Thr Thr Ala Ser Trp<br>              75                        80                            85 | | 356 |
| agc tac agc ggg agc aac atc cgc gct aat gtt gcg tat gac ttg ttc<br>Ser Tyr Ser Gly Ser Asn Ile Arg Ala Asn Val Ala Tyr Asp Leu Phe<br>                     90                            95                        100 | | 404 |
| acc gca gcc aac ccg aat cat gtc acg tac tcg gga gac tac gaa ctc<br>Thr Ala Ala Asn Pro Asn His Val Thr Tyr Ser Gly Asp Tyr Glu Leu<br>              105                        110                        115 | | 452 |
| atg atc tgg ctt ggc aaa tac ggc gat att ggg ccg att ggg tcc tca<br>Met Ile Trp Leu Gly Lys Tyr Gly Asp Ile Gly Pro Ile Gly Ser Ser<br>120                         125                            130 | | 500 |
| cag gga aca gtc aac gtc ggt ggc cag agc tgg acg ctc tac tat ggc<br>Gln Gly Thr Val Asn Val Gly Gly Gln Ser Trp Thr Leu Tyr Tyr Gly<br>135                         140                         145                        150 | | 548 |
| tac aac gga gcc atg caa gtc tat tcc ttt gtg gcc cag acc aac act<br>Tyr Asn Gly Ala Met Gln Val Tyr Ser Phe Val Ala Gln Thr Asn Thr<br>                    155                        160                        165 | | 596 |
| acc aac tac agc gga gat gtc aag aac ttc ttc aat tat ctc cga gac<br>Thr Asn Tyr Ser Gly Asp Val Lys Asn Phe Phe Asn Tyr Leu Arg Asp<br>              170                        175                        180 | | 644 |
| aat aaa gga tac aac gct gca ggc caa tat gtt ctt agc tac caa ttt<br>Asn Lys Gly Tyr Asn Ala Ala Gly Gln Tyr Val Leu Ser Tyr Gln Phe<br>185                         190                         195 | | 692 |
| ggt acc gag ccc ttc acg ggc agt gga act ctg aac gtc gca tcc tgg<br>Gly Thr Glu Pro Phe Thr Gly Ser Gly Thr Leu Asn Val Ala Ser Trp<br>200                         205                         210 | | 740 |
| acc gca tct atc aac taa ctcgagatcc ggctgctaac aaagcccgaa<br>Thr Ala Ser Ile Asn<br>215 | | 788 |
| aggaagctga gttggctgct gccaccgctg agcaataact agcataaccc cttggggcct | | 848 |
| ctaaacgggt cttgaggggt ttttgctga aggaggaac tatatccgga | | 898 |

<210> SEQ ID NO 30
<211> LENGTH: 219
<212> TYPE: PRT
<213> ORGANISM: Artificial
<220> FEATURE:
<223> OTHER INFORMATION: Synthetic Construct
<400> SEQUENCE: 30

Met Ala Gln Thr Ile Thr Gln Trp Ala Thr Phe Thr Gly Asn Gly Tyr
1               5                  10                  15

Thr Val Ser Asn Asn Leu Trp Gly Ala Ser Ala Gly Ser Gly Phe Gly
             20                  25                  30

Cys Val Thr Ala Val Ser Leu Ser Gly Gly Ala Ser Trp His Ala Asp
          35                  40                  45

Trp Gln Trp Ser Gly Gly Gln Asn Asn Val Lys Ser Tyr Gln Asn Ser
    50                       55                  60

Gln Ile Ala Ile Pro Gln Lys Arg Thr Val Asn Ser Ile Ser Ser Met

```
                65                  70                  75                  80
Pro Thr Thr Ala Ser Trp Ser Tyr Ser Gly Ser Asn Ile Arg Ala Asn
                    85                  90                  95

Val Ala Tyr Asp Leu Phe Thr Ala Asn Pro Asn His Val Thr Tyr
                100                 105                 110

Ser Gly Asp Tyr Glu Leu Met Ile Trp Leu Gly Lys Tyr Gly Asp Ile
                115                 120                 125

Gly Pro Ile Gly Ser Ser Gln Gly Thr Val Asn Val Gly Gly Gln Ser
        130                 135                 140

Trp Thr Leu Tyr Tyr Gly Tyr Asn Gly Ala Met Gln Val Tyr Ser Phe
145                 150                 155                 160

Val Ala Gln Thr Asn Thr Thr Asn Tyr Ser Gly Asp Val Lys Asn Phe
                165                 170                 175

Phe Asn Tyr Leu Arg Asp Asn Lys Gly Tyr Asn Ala Ala Gly Gln Tyr
                180                 185                 190

Val Leu Ser Tyr Gln Phe Gly Thr Glu Pro Phe Thr Gly Ser Gly Thr
            195                 200                 205

Leu Asn Val Ala Ser Trp Thr Ala Ser Ile Asn
        210                 215

<210> SEQ ID NO 31
<211> LENGTH: 60
<212> TYPE: PRT
<213> ORGANISM: Artificial Sequence
<220> FEATURE:
<223> OTHER INFORMATION: Synthetic Construct

<400> SEQUENCE: 31

Met Phe Lys Ala Leu Leu Ala Val Gly Phe Ala Ile Ala Leu Thr Phe
1               5                   10                  15

Ala Ser Ala Ala Gln Thr Ile Thr Gly Gln Tyr Asp Cys Ile Pro Ala
                20                  25                  30

Gly Ala Tyr Thr Leu Cys Gln Asn Leu Trp Gly Glu Tyr Ala Gly Val
            35                  40                  45

Gly Ser Gln Asn Ser Thr Leu Ile Ser Thr Asn Gly
        50                  55                  60

<210> SEQ ID NO 32
<211> LENGTH: 52
<212> TYPE: PRT
<213> ORGANISM: Artificial Sequence
<220> FEATURE:
<223> OTHER INFORMATION: Synthetic Construct

<400> SEQUENCE: 32

Asn Ala Val Thr Trp Gln Thr Asn Trp Thr Trp Ala Asn Asn Pro Asn
1               5                   10                  15

Thr Val Lys Ser Cys Ala Ser His Ser Phe Gln Ile Ala Ser Ser Ala
                20                  25                  30

Pro Thr Ala Trp Asn Trp Thr Tyr Val Thr Glu Ser Gln Gly Ile Arg
            35                  40                  45

Ala Asp Val Ser
        50

<210> SEQ ID NO 33
<211> LENGTH: 18
<212> TYPE: PRT
<213> ORGANISM: Artificial Sequence
<220> FEATURE:
<223> OTHER INFORMATION: Synthetic Construct
```

<400> SEQUENCE: 33

Tyr Ala Asn Leu Glu His Asn Thr Ala Lys Gly Met Gln Leu Gly Thr
1               5                   10                  15

Ile Thr

<210> SEQ ID NO 34
<211> LENGTH: 60
<212> TYPE: PRT
<213> ORGANISM: Artificial Sequence
<220> FEATURE:
<223> OTHER INFORMATION: Synthetic Construct

<400> SEQUENCE: 34

Tyr Asp Ile Trp Phe Gly Lys Ala Gln Ser Gly Asn Pro Ala Thr Ser
1               5                   10                  15

Ala Ser Ser Tyr Glu Ile Met Ile Trp Leu Ser Gly Leu Gly Gly Ile
                20                  25                  30

Gln Pro Val Gly His Gln Ile Leu Ser Gly Leu Asn Ile Ala Gly His
            35                  40                  45

Thr Trp Asn Leu Trp Ser Gly Pro Asn Ser Asn Trp
        50                  55                  60

<210> SEQ ID NO 35
<211> LENGTH: 60
<212> TYPE: PRT
<213> ORGANISM: Artificial Sequence
<220> FEATURE:
<223> OTHER INFORMATION: Synthetic Construct

<400> SEQUENCE: 35

Gln Val Phe Ser Phe Val Ile Ser Ser Gly Glu Val Arg Asn Phe Ser
1               5                   10                  15

Ala Asp Leu Asn Glu Phe Phe Gln Tyr Leu Ile Gln Ser Gln Gly Val
                20                  25                  30

Ala Ser Thr Gln Tyr Leu Gln Ala Ile Gln Val Gly Thr Glu Pro Phe
            35                  40                  45

Val Gly Ser Ala Ser Leu Leu Thr Glu Ser Phe Ala
        50                  55                  60

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Val Ala Val Asn Val
1               5

<210> SEQ ID NO 37
<211> LENGTH: 50
<212> TYPE: PRT
<213> ORGANISM: Artificial Sequence
<220> FEATURE:
<223> OTHER INFORMATION: Synthetic Construct

<400> SEQUENCE: 37

Ile Thr Gly Gln Tyr Asp Cys Ile Pro Ala Gly Ala Tyr Thr Leu Cys
1               5                   10                  15

Gln Asn Leu Trp Gly Glu Tyr Ala Gly Val Gly Ser Gln Asn Ser Thr
                20                  25                  30

Leu Ile Ser Thr Asn Gly Asn Ala Val Thr Trp Gln Thr Asn Trp Thr
            35                  40                  45

Trp Ala
    50

<210> SEQ ID NO 38
<211> LENGTH: 53
<212> TYPE: PRT
<213> ORGANISM: Artificial Sequence
<220> FEATURE:
<223> OTHER INFORMATION: Synthetic Construct

<400> SEQUENCE: 38

Ala Gln Thr Ile Thr Gly Gln Tyr Asp Cys Ile Pro Ala Gly Ala Tyr
1               5                   10                  15

Thr Leu Cys Gln Asn Leu Trp Gly Glu Tyr Ala Gly Val Gly Ser Gln
                20                  25                  30

Asn Ser Thr Leu Ile Ser Thr Asn Gly Asn Ala Val Thr Trp Gln Thr
            35                  40                  45

Asn Trp Thr Trp Ala
    50

<210> SEQ ID NO 39
<211> LENGTH: 70
<212> TYPE: PRT
<213> ORGANISM: Polyporus arcularius

<400> SEQUENCE: 39

Met His Phe Ser Thr Leu Ala Thr Leu Val Ala Val Ala Ala Thr Ala
1               5                   10                  15

Ser Ala Gln Thr Leu Ser Gly Gln Tyr Asp Cys Ala Pro Ala Gly Ala
                20                  25                  30

Tyr Thr Leu Cys Gln Asn Leu Trp Gly Glu Ser Ser Gly Val Gly Asn
            35                  40                  45

Gln Asn Ser Thr Leu Ile Ser Thr Ser Gly Asn Thr Val Ser Trp Arg
        50                  55                  60

Thr Gln Trp Gln Trp Gln
65                  70

<210> SEQ ID NO 40
<211> LENGTH: 71
<212> TYPE: PRT
<213> ORGANISM: Fomitopsis palustris

<400> SEQUENCE: 40

Met Gln Leu Arg Thr Ser Phe Val Leu Ala Ala Val Ala Val Ser Ala
1               5                   10                  15

Gln Ala Ala Thr Thr Leu Thr Gly Gln Tyr Ser Cys Ala Thr Ser Gly
                20                  25                  30

Asn Tyr Gln Leu Cys Asn Asp Gln Trp Gly Ser Gly Asn Gly Glu Gly
            35                  40                  45

Ser Gln Thr Ser Thr Leu Glu Ser Thr Ser Gly Asp Ser Ile Thr Trp
        50                  55                  60

Ser Thr Thr Tyr Thr Trp Ser
65                  70

<210> SEQ ID NO 41
<211> LENGTH: 67
<212> TYPE: PRT
<213> ORGANISM: Artificial Sequence

```
<220> FEATURE:
<223> OTHER INFORMATION: Synthetic Construct

<400> SEQUENCE: 41

Met Lys Phe Leu Gln Val Leu Pro Ala Leu Ile Pro Ala Ala Leu Ala
1               5                   10                  15

Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala Ser Trp His Ala Asp Trp
    50                  55                  60

Gln Trp Ser
65

<210> SEQ ID NO 42
<211> LENGTH: 68
<212> TYPE: PRT
<213> ORGANISM: Artificial Sequence
<220> FEATURE:
<223> OTHER INFORMATION: Synthetic Construct

<400> SEQUENCE: 42

Met Lys Leu Pro Val Ser Leu Ala Met Leu Ala Ala Thr Ala Met Gly
1               5                   10                  15

Gln Thr Met Cys Ser Gln Tyr Asp Ser Ala Ser Ser Pro Pro Tyr Ser
            20                  25                  30

Val Asn Gln Asn Leu Trp Gly Glu Tyr Gln Gly Thr Gly Ser Gln Cys
        35                  40                  45

Val Tyr Val Asp Lys Leu Ser Ser Ser Gly Ala Ser Trp His Thr Glu
    50                  55                  60

Trp Thr Trp Ser
65

<210> SEQ ID NO 43
<211> LENGTH: 80
<212> TYPE: PRT
<213> ORGANISM: Aspergillus niger

<400> SEQUENCE: 43

Met Asn Arg Tyr Leu Ser Ile Pro Leu Cys Leu Ala Ser Ala Val Pro
1               5                   10                  15

Ala Leu Ala Gly Leu Ala Ala Arg Asp Pro Ile Gly Thr Ile Cys Thr
            20                  25                  30

Lys Asn Asn Ile Ile Thr Thr Asp Asp Phe Ile Leu Tyr Asn Asn Leu
        35                  40                  45

Trp Gly Glu Asp Tyr Ala Thr Ser Gly Ser Glu Cys Thr Tyr Leu Asp
    50                  55                  60

Tyr Asp Ser Gly Asn Ser Ile Ser Trp Gln Thr Ser Trp Thr Trp Ala
65                  70                  75                  80

<210> SEQ ID NO 44
<211> LENGTH: 74
<212> TYPE: PRT
<213> ORGANISM: Aspergillus oryzae

<400> SEQUENCE: 44

Met Lys Phe Leu Thr Pro Leu Val Leu Ser Ser Leu Ala Ser Ala Ala
1               5                   10                  15

Ala Leu Asn Arg Arg Ala Asp Met Cys Gly Gln Trp Asp Thr Thr Thr
```

```
                    20                  25                  30

Thr Asp Lys Phe Thr Leu Tyr Asn Asn Leu Trp Gly Glu Gly Asn Ala
         35                  40                  45

Asp Ser Gly Ser Gln Cys Thr Gly Leu Asp Ser Asp Asp Gly Asn Thr
     50                  55                  60

Ile Ala Trp His Thr Ser Trp Thr Trp Thr
65                  70

<210> SEQ ID NO 45
<211> LENGTH: 54
<212> TYPE: PRT
<213> ORGANISM: Aspergillus aculeatus

<400> SEQUENCE: 45

Arg Arg Ser Asp Phe Cys Gly Gln Trp Asp Thr Ala Thr Ala Gly Asp
1               5                  10                  15

Phe Thr Leu Tyr Asn Asp Leu Trp Gly Glu Ser Ala Gly Thr Gly Ser
                20                  25                  30

Gln Cys Thr Gly Val Asp Ser Tyr Ser Gly Asp Thr Ile Ala Trp His
         35                  40                  45

Thr Ser Trp Ser Trp Ser
     50

<210> SEQ ID NO 46
<211> LENGTH: 79
<212> TYPE: PRT
<213> ORGANISM: Artificial Sequence
<220> FEATURE:
<223> OTHER INFORMATION: Synthetic Construct

<400> SEQUENCE: 46

Asn Asn Pro Asn Thr Val Lys Ser Tyr Ala Asn Leu Glu His Asn Thr
1               5                  10                  15

Ala Lys Gly Met Gln Leu Gly Thr Ile Thr Ser Ala Pro Thr Ala Trp
                20                  25                  30

Asn Trp Thr Tyr Val Thr Glu Ser Gln Gly Ile Arg Ala Asp Val Ser
         35                  40                  45

Tyr Asp Ile Trp Phe Gly Lys Ala Gln Ser Gly Asn Pro Ala Thr Ser
     50                  55                  60

Ala Ser Ser Tyr Glu Ile Met Ile Trp Leu Ser Gly Leu Gly Gly
65                  70                  75

<210> SEQ ID NO 47
<211> LENGTH: 71
<212> TYPE: PRT
<213> ORGANISM: Artificial Sequence
<220> FEATURE:
<223> OTHER INFORMATION: Synthetic Construct

<400> SEQUENCE: 47

Asn Asn Pro Asn Thr Val Lys Ser Cys Ala Ser His Ser Phe Pro Ile
1               5                  10                  15

Ala Ser Ser Ala Pro Thr Ala Trp Asn Trp Thr Tyr Val Thr Glu Ser
                20                  25                  30

Gln Gly Ile Arg Ala Asp Val Ser Tyr Asp Ile Trp Phe Gly Lys Ala
         35                  40                  45

Gln Ser Gly Asn Pro Ala Thr Ser Ala Ser Ser Tyr Glu Ile Met Ile
     50                  55                  60

Trp Leu Ser Gly Leu Gly Gly
65                  70
```

```
<210> SEQ ID NO 48
<211> LENGTH: 79
<212> TYPE: PRT
<213> ORGANISM: Polyporus arcularius

<400> SEQUENCE: 48

Asn Asn Pro Asn Asn Val Lys Ser Tyr Ala Asn Leu Leu Ser Asn Ser
1               5                   10                  15

Ala Lys Gly Val Gln Leu Ser Ala Val Arg Ala Ala Pro Thr Ala Trp
            20                  25                  30

Gln Trp Glu Tyr Glu Ser Lys Ser Asp Gly Ile Arg Ala Asp Val Ser
        35                  40                  45

Tyr Asp Ile Trp Leu Gly Thr Ala Pro Ser Gly Asp Pro Ala Ser Arg
    50                  55                  60

Ala Ser Ser Tyr Glu Ile Met Ile Trp Leu Ser Gly Leu Gly Gly
65                  70                  75

<210> SEQ ID NO 49
<211> LENGTH: 79
<212> TYPE: PRT
<213> ORGANISM: Fomitopsis palustris

<400> SEQUENCE: 49

Glu Asn Glu Asn Asp Val Lys Ser Tyr Ala Asn Val Glu Pro Thr Ser
1               5                   10                  15

Gly Ala Ser Gly Met Thr Leu Ala Glu Ile Thr Ser Ala Pro Thr Thr
            20                  25                  30

Tyr Asn Trp Glu Tyr Thr Ser Ser Ser Gly Leu Arg Ala Asp Val
        35                  40                  45

Ser Tyr Asp Ile Trp Thr Gly Thr Ser Ala Gly Asp Pro Ala Ser Ser
    50                  55                  60

Thr Ser Asn Tyr Glu Ile Met Ile Trp Leu Ser Gly Glu Gly Gly
65                  70                  75

<210> SEQ ID NO 50
<211> LENGTH: 75
<212> TYPE: PRT
<213> ORGANISM: Artificial Sequence
<220> FEATURE:
<223> OTHER INFORMATION: Synthetic Construct

<400> SEQUENCE: 50

Gly Gly Gln Asn Asn Val Lys Ser Tyr Gln Asn Ser Gln Ile Ala Ile
1               5                   10                  15

Pro Gln Lys Arg Thr Val Asn Ser Ile Ser Ser Met Pro Thr Thr Ala
            20                  25                  30

Ser Trp Ser Tyr Ser Gly Ser Asn Ile Arg Ala Asn Val Ala Tyr Asp
        35                  40                  45

Leu Phe Thr Ala Ala Asn Pro Asn His Val Thr Tyr Ser Gly Asp Tyr
    50                  55                  60

Glu Leu Met Ile Trp Leu Gly Lys Tyr Gly Asp
65                  70                  75

<210> SEQ ID NO 51
<211> LENGTH: 74
<212> TYPE: PRT
<213> ORGANISM: Artificial Sequence
<220> FEATURE:
<223> OTHER INFORMATION: Synthetic Construct
```

-continued

<400> SEQUENCE: 51

Gly Gly Glu Gly Thr Val Lys Ser Tyr Ser Asn Ser Gly Val Thr Phe
1               5                   10                  15

Asn Lys Lys Leu Val Ser Asp Val Ser Ser Ile Pro Thr Ser Val Glu
            20                  25                  30

Trp Lys Gln Asp Asn Thr Asn Val Asn Ala Asp Val Ala Tyr Asp Leu
        35                  40                  45

Phe Thr Ala Ala Asn Val Asp His Ala Thr Ser Ser Gly Asp Tyr Glu
    50                  55                  60

Leu Met Ile Trp Leu Ala Arg Tyr Gly Asn
65                  70

<210> SEQ ID NO 52
<211> LENGTH: 73
<212> TYPE: PRT
<213> ORGANISM: Aspergillus niger

<400> SEQUENCE: 52

Gly Gly Asp Asp Tyr Val Lys Ser Tyr Pro Asn Ala Val Leu Asn Val
1               5                   10                  15

Gly Ala Lys Gln Leu Ser Thr Ile Thr Ser Ile Pro Ser Thr Trp Lys
            20                  25                  30

Trp Ser Tyr Thr Gly Asn Asp Leu Val Ala Asp Val Ser Tyr Asp Ala
        35                  40                  45

Phe Leu Ser Thr Thr Asp Ser Thr Thr Ala Thr His Glu Tyr Glu Ile
    50                  55                  60

Met Ile Trp Leu Ala Ala Tyr Gly Gly
65                  70

<210> SEQ ID NO 53
<211> LENGTH: 71
<212> TYPE: PRT
<213> ORGANISM: Aspergillus oryzae

<400> SEQUENCE: 53

Gly Gly Ala Gly Gln Val Lys Ser Phe Ala Asn Val Ala Tyr Asn Phe
1               5                   10                  15

Glu Ala Thr Gln Leu Ser Gln Leu Ser Ser Ile Pro Ser Thr Trp Lys
            20                  25                  30

Trp Glu Asn Thr Gly Ser Asp Ile Val Ala Asp Val Ala Tyr Asp Leu
        35                  40                  45

Phe Thr Ser Ser Ser Ala Asp Gly Asp Glu Glu Tyr Glu Ile Met Ile
    50                  55                  60

Trp Leu Ala Ala Leu Gly Gly
65                  70

<210> SEQ ID NO 54
<211> LENGTH: 71
<212> TYPE: PRT
<213> ORGANISM: Aspergillus aculeatus

<400> SEQUENCE: 54

Gly Gly Ser Ser Val Lys Ser Tyr Ala Asn Ala Ala Leu Thr Phe
1               5                   10                  15

Thr Pro Thr Gln Leu Asn Cys Ile Ser Ser Ile Pro Thr Thr Trp Lys
            20                  25                  30

Trp Ser Tyr Ser Gly Ser Ser Ile Val Ala Asp Val Ala Tyr Asp Thr
        35                  40                  45

Phe Leu Ala Glu Thr Ala Ser Gly Ser Ser Lys Tyr Glu Ile Met Val
            50                  55                  60

Trp Leu Ala Ala Leu Gly Gly
 65                  70

<210> SEQ ID NO 55
<211> LENGTH: 73
<212> TYPE: PRT
<213> ORGANISM: Artificial Sequence
<220> FEATURE:
<223> OTHER INFORMATION: Synthetic Construct

<400> SEQUENCE: 55

Ile Gln Pro Val Gly His Gln Ile Leu Ser Gly Leu Asn Ile Ala Gly
  1               5                  10                  15

His Thr Trp Asn Leu Trp Ser Gly Pro Asn Ser Asn Trp Gln Val Phe
                 20                  25                  30

Ser Phe Val Ile Ser Ser Gly Glu Val Arg Asn Phe Ser Ala Asp Leu
             35                  40                  45

Asn Glu Phe Phe Gln Tyr Leu Ile Gln Ser Gly Val Ala Ser Thr
         50                  55                  60

Gln Tyr Leu Gln Ala Ile Gln Val Gly
 65                  70

<210> SEQ ID NO 56
<211> LENGTH: 73
<212> TYPE: PRT
<213> ORGANISM: Artificial Sequence
<220> FEATURE:
<223> OTHER INFORMATION: Synthetic Construct

<400> SEQUENCE: 56

Ile Gln Pro Val Gly His Gln Ile Leu Ser Gly Leu Asn Ile Ala Gly
  1               5                  10                  15

His Thr Trp Asn Leu Trp Ser Gly Pro Asn Ser Asn Trp Gln Val Phe
                 20                  25                  30

Ser Phe Val Ile Ser Ser Gly Glu Val Arg Asn Phe Ser Ala Asp Leu
             35                  40                  45

Asn Glu Phe Phe Gln Tyr Leu Ile Gln Ser Gly Val Ala Ser Thr
         50                  55                  60

Gln Tyr Leu Gln Ala Ile Gln Val Gly
 65                  70

<210> SEQ ID NO 57
<211> LENGTH: 73
<212> TYPE: PRT
<213> ORGANISM: Polyporus arcularius

<400> SEQUENCE: 57

Ile Gln Pro Val Gly Ser Lys Ile Leu Ser Gly Val Asn Val Ala Gly
  1               5                  10                  15

His Thr Trp Asp Leu Trp Lys Gly Pro Asn Ser Asn Trp Gln Val Leu
                 20                  25                  30

Ser Phe Val Ser Ser Thr Gly Asp Ile Thr Asp Phe Asn Val Asp Leu
             35                  40                  45

Lys Asp Phe Phe Asn Tyr Leu Thr Gln Ser Gln Gly Val Ala Ala Ser
         50                  55                  60

Gln Tyr Val Gln Ala Ile Gln Thr Gly
 65                  70

```
<210> SEQ ID NO 58
<211> LENGTH: 73
<212> TYPE: PRT
<213> ORGANISM: Fomitopsis palustris

<400> SEQUENCE: 58

Ile Gln Pro Val Gly Ser Gln Ile Asp Ser Gly Val Ser Val Ala Gly
1               5                   10                  15

Tyr Ser Trp Asn Leu Trp Ser Gly Pro Asn Ser Asn Trp Gln Thr Ile
            20                  25                  30

Ser Phe Val Ser Ala Asp Gly Asn Ile Asn Asp Phe Ser Ala Asp Leu
        35                  40                  45

Asn Glu Phe Phe Gln Tyr Leu Glu Glu Asn Gln Gly Val Ser Thr Ser
    50                  55                  60

Gln Val Leu Gln Ala Ile Gln Ala Gly
65                  70

<210> SEQ ID NO 59
<211> LENGTH: 72
<212> TYPE: PRT
<213> ORGANISM: Artificial Sequence
<220> FEATURE:
<223> OTHER INFORMATION: Synthetic Construct

<400> SEQUENCE: 59

Ile Gly Pro Ile Gly Ser Ser Gln Gly Thr Val Asn Val Gly Gly Gln
1               5                   10                  15

Ser Trp Thr Leu Tyr Tyr Gly Tyr Asn Gly Ala Met Gln Val Tyr Ser
            20                  25                  30

Phe Val Ala Gln Thr Asn Thr Thr Asn Tyr Ser Gly Asp Val Lys Asn
        35                  40                  45

Phe Phe Asn Tyr Leu Arg Asp Asn Lys Gly Tyr Asn Ala Ala Gly Gln
    50                  55                  60

Tyr Val Leu Ser Tyr Gln Phe Gly
65                  70

<210> SEQ ID NO 60
<211> LENGTH: 76
<212> TYPE: PRT
<213> ORGANISM: Artificial Sequence
<220> FEATURE:
<223> OTHER INFORMATION: Synthetic Construct

<400> SEQUENCE: 60

Ile Gln Pro Ile Gly Lys Gln Ile Ala Thr Ala Thr Val Gly Gly Lys
1               5                   10                  15

Ser Trp Glu Val Trp Tyr Gly Ser Thr Thr Gln Ala Gly Ala Glu Gln
            20                  25                  30

Arg Thr Tyr Ser Phe Val Ser Glu Ser Pro Ile Asn Ser Tyr Ser Gly
        35                  40                  45

Asp Ile Asn Ala Phe Phe Ser Tyr Leu Thr Gln Asn Gln Gly Phe Pro
    50                  55                  60

Ala Ser Ser Gln Tyr Leu Ile Asn Leu Gln Phe Gly
65                  70                  75

<210> SEQ ID NO 61
<211> LENGTH: 73
<212> TYPE: PRT
<213> ORGANISM: Aspergillus niger

<400> SEQUENCE: 61
```

-continued

```
Ile Glu Pro Ile Gly Asn Ser Asp Gly Pro Ile Ala Ser Pro Thr Ile
1               5                   10                  15

Gly Gly Tyr Thr Trp Asp Leu Tyr Lys Gly Pro Asn Asp Trp Thr Val
            20                  25                  30

Tyr Ser Phe Val Ala Arg Glu Thr Ile Thr Asp Phe Ser Ala Asp Val
        35                  40                  45

Leu Glu Phe Phe Thr Tyr Leu Val Asp Asn Glu Gly Val Ser Ser Ser
    50                  55                  60

Leu Tyr Leu Gln Thr Leu Gly Ala Gly
65                  70

<210> SEQ ID NO 62
<211> LENGTH: 74
<212> TYPE: PRT
<213> ORGANISM: Aspergillus oryzae

<400> SEQUENCE: 62

Ala Gly Pro Ile Ser Ser Thr Gly Ser Ala Ile Ala Thr Pro Thr Val
1               5                   10                  15

Gly Gly Gln Ser Trp Ser Leu Tyr Ser Gly Pro Asn Gly Gln Met Thr
            20                  25                  30

Val Phe Ser Phe Val Ala Ser Ser Thr Thr Glu Asp Phe Ser Ala Asp
        35                  40                  45

Leu Asn Asp Phe Leu Lys Tyr Leu Gln Glu Gln Gly Met Pro Ser
    50                  55                  60

Ser Gln Tyr Leu Thr His Val Gln Ala Gly
65                  70

<210> SEQ ID NO 63
<211> LENGTH: 74
<212> TYPE: PRT
<213> ORGANISM: Aspergillus aculeatus

<400> SEQUENCE: 63

Ala Gly Pro Ile Ser Ser Thr Gly Ser Thr Ile Ala Thr Pro Thr Ile
1               5                   10                  15

Ala Gly Val Asn Trp Lys Leu Tyr Ser Gly Pro Asn Gly Asp Thr Thr
            20                  25                  30

Val Tyr Ser Phe Val Ala Asp Ser Thr Thr Glu Ser Phe Ser Gly Asp
        35                  40                  45

Leu Asn Asp Phe Phe Thr Tyr Leu Val Asp Asn Glu Gly Val Ser Asp
    50                  55                  60

Glu Leu Tyr Leu Thr Thr Leu Glu Ala Gly
65                  70

<210> SEQ ID NO 64
<211> LENGTH: 23
<212> TYPE: PRT
<213> ORGANISM: Artificial Sequence
<220> FEATURE:
<223> OTHER INFORMATION: Synthetic Construct

<400> SEQUENCE: 64

Thr Glu Pro Phe Val Gly Ser Ala Ser Leu Leu Thr Glu Ser Phe Ala
1               5                   10                  15

Val Ala Val Asn Val Gly Ser
            20

<210> SEQ ID NO 65
<211> LENGTH: 21
```

```
<212> TYPE: PRT
<213> ORGANISM: Artificial Sequence
<220> FEATURE:
<223> OTHER INFORMATION: Synthetic Construct

<400> SEQUENCE: 65

Thr Glu Pro Phe Val Gly Ser Ala Ser Leu Leu Thr Glu Ser Phe Ala
1               5                   10                  15

Val Ala Val Asn Val
            20

<210> SEQ ID NO 66
<211> LENGTH: 21
<212> TYPE: PRT
<213> ORGANISM: Polyporus arcularius

<400> SEQUENCE: 66

Thr Glu Pro Phe Thr Gly Ser Ala Ser Leu Phe Thr Lys Ala Tyr Ser
1               5                   10                  15

Val Ala Ile Asn Gln
            20

<210> SEQ ID NO 67
<211> LENGTH: 21
<212> TYPE: PRT
<213> ORGANISM: Fomitopsis palustris

<400> SEQUENCE: 67

Thr Glu Ala Phe Thr Gly Ser Ala Thr Leu Ser Val Thr Asp Tyr Ser
1               5                   10                  15

Val Thr Val Asn Thr
            20

<210> SEQ ID NO 68
<211> LENGTH: 20
<212> TYPE: PRT
<213> ORGANISM: Artificial Sequence
<220> FEATURE:
<223> OTHER INFORMATION: Synthetic Construct

<400> SEQUENCE: 68

Thr Glu Pro Phe Thr Gly Ser Gly Thr Leu Asn Val Ala Ser Trp Thr
1               5                   10                  15

Ala Ser Ile Asn
            20

<210> SEQ ID NO 69
<211> LENGTH: 21
<212> TYPE: PRT
<213> ORGANISM: Artificial Sequence
<220> FEATURE:
<223> OTHER INFORMATION: Synthetic Construct

<400> SEQUENCE: 69

Thr Glu Ala Phe Thr Gly Gly Pro Ala Thr Phe Thr Val Asp Asn Trp
1               5                   10                  15

Thr Ala Ser Val Asn
            20

<210> SEQ ID NO 70
<211> LENGTH: 22
<212> TYPE: PRT
<213> ORGANISM: Aspergillus niger

<400> SEQUENCE: 70
```

```
Thr Glu Pro Lys Thr Gly Ser Asp Ala Trp Phe Thr Val Ser Pro Tyr
1               5                   10                  15

Thr Val Ser Ile Asn Thr
            20

<210> SEQ ID NO 71
<211> LENGTH: 21
<212> TYPE: PRT
<213> ORGANISM: Aspergillus oryzae

<400> SEQUENCE: 71

Thr Glu Pro Phe Ser Gly Ser Asn Val Lys Phe Thr Thr Ser Ser Tyr
1               5                   10                  15

Ser Val Ser Val Ala
            20

<210> SEQ ID NO 72
<211> LENGTH: 21
<212> TYPE: PRT
<213> ORGANISM: Aspergillus aculeatus

<400> SEQUENCE: 72

Thr Glu Pro Phe Thr Gly Ser Asp Ala Lys Leu Thr Val Ser Glu Tyr
1               5                   10                  15

Ser Ile Ser Ile Glu
            20
```